(12) United States Patent
Ziv

(10) Patent No.: US 10,881,308 B2
(45) Date of Patent: Jan. 5, 2021

(54) SYSTEMS AND METHODS FOR IMPROVING HEART-RATE VARIABILITY

(71) Applicant: ZIV HEALTHCARE LTD, Rehovot (IL)

(72) Inventor: Amos Ziv, Rehovot (IL)

(73) Assignee: ZIV HEALTHCARE LTD., Rehovot (IL)

( * ) Notice: Subject to any disclaimer, the term of this patent is extended or adjusted under 35 U.S.C. 154(b) by 469 days.

(21) Appl. No.: 15/551,095

(22) PCT Filed: Feb. 15, 2016

(86) PCT No.: PCT/IL2016/050177
§ 371 (c)(1),
(2) Date: Aug. 15, 2017

(87) PCT Pub. No.: WO2016/128985
PCT Pub. Date: Aug. 18, 2016

(65) Prior Publication Data
US 2018/0028809 A1 Feb. 1, 2018

Related U.S. Application Data

(60) Provisional application No. 62/116,445, filed on Feb. 15, 2015.

(51) Int. Cl.
*A61B 5/024* (2006.01)
*A61N 1/04* (2006.01)
(Continued)

(52) U.S. Cl.
CPC ........ *A61B 5/02405* (2013.01); *A61B 5/0456* (2013.01); *A61B 5/4836* (2013.01);
(Continued)

(58) Field of Classification Search
CPC .............. A61N 1/36031; A61N 1/0456; A61N 1/0492; A61N 1/36014; A61N 1/36114;
(Continued)

(56) References Cited

U.S. PATENT DOCUMENTS 7,321,792 B1 * 1/2008 Min .................... A61H 39/002
128/907
8,417,334 B2 4/2013 Hill et al.
(Continued)

FOREIGN PATENT DOCUMENTS

| CN | 1081382 A | 2/1994 |
|---|---|---|
| CN | 202892665 U | 4/2013 |

(Continued)

OTHER PUBLICATIONS

Zengyong Li et al., "Effects of acupuncture on heart rate variability in normal subjects under fatigue and non-fatigue state", European journal of applied physiology 94, p. 633-640, 2005.
(Continued)

*Primary Examiner* — Catherine M Voorhees
*Assistant Examiner* — Roland Dinga
(74) *Attorney, Agent, or Firm* — The Roy Gross Law Firm, LLC; Roy Gross

(57) ABSTRACT

The present invention discloses neuro-stimulation systems and methods for affecting cardiovascular function, particularly for improving heart rate variability and treating arrhythmia.

21 Claims, 15 Drawing Sheets

(51) Int. Cl.
  *A61B 5/00* (2006.01)
  *A61B 5/0456* (2006.01)
  *A61H 39/00* (2006.01)
  *A61N 1/36* (2006.01)
  *A61B 5/0488* (2006.01)
  *A61B 5/053* (2006.01)
  *A61B 5/0205* (2006.01)
  *A61B 5/021* (2006.01)

(52) U.S. Cl.
  CPC .......... *A61B 5/4854* (2013.01); *A61B 5/7285* (2013.01); *A61H 39/002* (2013.01); *A61N 1/0456* (2013.01); *A61N 1/0492* (2013.01); *A61N 1/36031* (2017.08); *A61N 1/36034* (2017.08); *A61B 5/021* (2013.01); *A61B 5/0205* (2013.01); *A61B 5/02055* (2013.01); *A61B 5/02433* (2013.01); *A61B 5/0488* (2013.01); *A61B 5/0531* (2013.01); *A61B 2562/0219* (2013.01); *A61H 2201/1207* (2013.01); *A61H 2201/5007* (2013.01); *A61H 2201/5084* (2013.01); *A61H 2201/5092* (2013.01); *A61H 2201/5097* (2013.01); *A61H 2205/065* (2013.01); *A61H 2205/106* (2013.01); *A61H 2205/12* (2013.01); *A61H 2230/06* (2013.01); *A61H 2230/065* (2013.01); *A61H 2230/085* (2013.01); *A61H 2230/10* (2013.01); *A61H 2230/105* (2013.01); *A61H 2230/30* (2013.01); *A61H 2230/305* (2013.01); *A61H 2230/50* (2013.01); *A61H 2230/505* (2013.01); *A61H 2230/60* (2013.01); *A61H 2230/605* (2013.01); *A61H 2230/65* (2013.01); *A61H 2230/655* (2013.01); *A61N 1/36114* (2013.01)

(58) Field of Classification Search
  CPC .............. A61N 1/36034; A61N 1/0476; A61B 5/02433; A61B 5/0488; A61B 5/0531; A61B 5/021; A61B 5/02055; A61B 5/02405; A61B 5/4854; A61B 5/7285; A61B 5/4836; A61B 5/0205; A61B 5/04085; A61B 2562/0219; A61H 39/002; A61H 2230/30; A61H 2230/065; A61H 2230/1207; A61H 2230/65; A61H 2230/605; A61H 2230/60; A61H 2230/10; A61H 2230/50; A61H 2230/105; A61H 2230/085; A61H 2230/06; A61H 2230/305; A61H 2230/505; A61H 2230/655; A61H 2201/5007; A61H 2201/5084; A61H 2201/5092; A61H 2201/5097; A61H 2205/065; A61H 2205/106; A61H 2205/12

See application file for complete search history.

(56) References Cited

U.S. PATENT DOCUMENTS

| | | |
|---|---|---|
| 8,571,687 B2 | 10/2013 | Libbus et al. |
| 2003/0233047 A1 | 12/2003 | Lai |
| 2008/0021504 A1 | 1/2008 | McCabe et al. |
| 2009/0326595 A1 | 12/2009 | Brockway et al. |
| 2011/0046687 A1 | 2/2011 | Naschberger |
| 2014/0051906 A1 | 2/2014 | Chen et al. |
| 2014/0214124 A1 | 7/2014 | Greiner et al. |
| 2015/0032178 A1 | 1/2015 | Simon et al. |

FOREIGN PATENT DOCUMENTS

| | | |
|---|---|---|
| CN | 103429197 A | 12/2013 |
| JP | 2010506618 | 4/2008 |

OTHER PUBLICATIONS

International Search Report of PCT/IL2016/050177 Completed Jul. 2015, 2016; dated Jul. 28, 2016 5 Pages.
Written Opinion of PCT/IL2016/050177 Completed Jul. 2015, 2016; dated Jul. 28, 2016 8 Pages.
Chinese Office Action dated Jul. 23, 2020 received in co-pending Chinese app. No. 201680016270.0 1 page.

\* cited by examiner

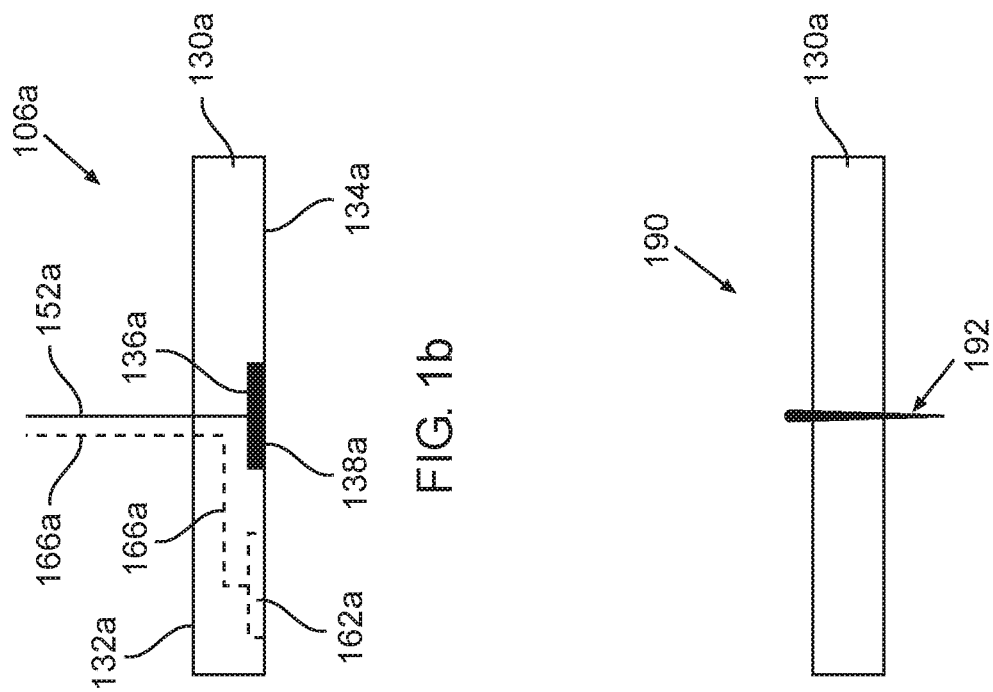
FIG. 1b
FIG. 1c
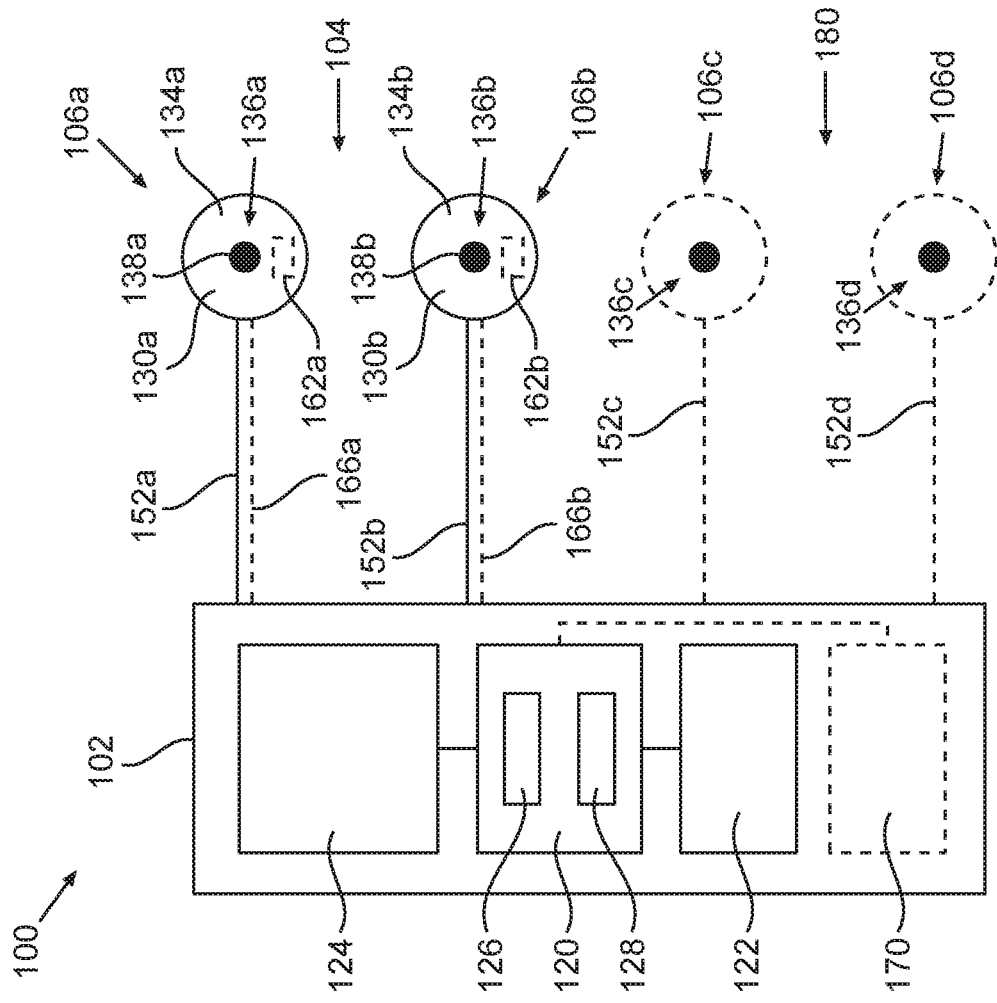
FIG. 1a 30 sec wave 30 sec wave 30 sec wave 30 sec wave

SYSTEMS AND METHODS FOR IMPROVING HEART-RATE VARIABILITY

RELATED APPLICATIONS

This application is a National Phase of PCT Patent Application No. PCT/IL2016/050177 having International filing date of Feb. 15, 2016, which claims the benefit of priority of U.S. Patent Application No. 62/116,445 filed on Feb. 15, 2015. The contents of the above applications are all incorporated by reference as if fully set forth herein in their entirety.

FIELD OF THE INVENTION

The present invention relates to the field of electrical neuro-stimulation, and more particularly, but not exclusively, to electrical neuro-stimulation for modulating cardiovascular functions.

BACKGROUND OF THE INVENTION

Heart-rate variability (HRV) refers to a phenomenon of variation in the time intervals between normal heart beats (i.e. non-arrhythmic heart beats). In a normal healthy state, the time intervals between successive heart beats may vary significantly in response to a change in activity, e.g. getting up from a sitting position, indicating a healthy and flexible interplay between the autonomic nervous system and the cardiovascular system. Higher HRV parameters, such as the standard deviation of the time intervals between successive normal heart beats (i.e. the standard deviation of NN intervals or SDNN), and the square root of the mean of the squares of time intervals between successive normal heart beats (i.e. the root-mean-square of successive differences or rMSSD), indicate better health and wellbeing. Lower HRV parameters may indicate high stress, poor rest or sleep as well as certain pathological conditions. In sports and fitness, higher HRV before a workout was shown to induce better performance in the workout. In cardiology, patients with lower HRV after a myocardial infarct, were shown to have higher incidence of cardiac arrhythmias and increased all-cause mortality rates. The joint taskforce of the European Society of Cardiology and the North American Society of Pacing and Electrophysiology [Eu. Heart Journal. 17, 354-381; 1996 and Circulation Journal 1; 93(5):1043-65] issued a guidelines statement emphasizing the importance of monitoring HRV and outlined the clinical benefits of HRV improvement. Some research reports [Circulation Journal. 102:1239-1244, 2000] showed that HRV measurements from a 2 minute rhythm strip is sufficient for determining increased risk of cardiovascular morbidity and mortality. Others have reported [Journal of Cardiovascular Electrophysiology 25(7):719-24; 2014] the close relations between HRV and cardiac arrhythmias such as atrial fibrillation (AF) and emphasize the importance of monitoring HRV for preventing cardiac arrhythmias.

Neuromodulation, i.e. stimulation of nerves, may be used to treat various conditions, ranging from psychiatric disorders, such as depression, to physiological conditions, such as chronic pain. In particular, neuromodulation of peripheral nerves may modulate the autonomic nervous system. For example, neuromodulation of the median and ulnar nerves in the forearm may enhance parasympathetic activity of the vagus nerve and depress sympathetic activity of the cardiac nerve, and thereby reduce heart rate, regulate heart rhythm, and correct and prevent cardiac arrhythmias. Neuromodulation of the median and ulnar nerves may also induce a neurohormonal response: secretion of endorphins, decrease of stress related hormones, and thereby reduce stress and improve sleep.

U.S. Pat. No. 8,571,687 to Libbus et al. discloses a neurostimulation device, which includes an external neurostimulator worn by a patient using a bracing element that braces a portion of the patient's body. The external neurostimulator delivers neurostimulation to modulate a cardiovascular function of the patient. In one embodiment, the external stimulator delivers the neurostimulation transcutaneously to a stimulation target in the patient's body using surface stimulation electrodes placed on the body approximately over the stimulation target.

US Pat. Application Publication No. 2009/326595 to Brockway et al. discloses a method of providing therapy to a patient to prevent an occurrence of a dangerous cardiac event, in which a cardiac signal sensed over multiple cardiac cycles is received. A risk of impending cardiovascular insult is determined, using the received cardiac signal, by assessing an indicator of proarrhythmogenic substrate and a change in sympathovagal balance. A therapy comprising acupuncture to modulate sympathovagal balance is administered based on the determined risk.

U.S. Pat. No. 8,417,334 to Hill et al. discloses a method and apparatus used to provide therapy to a patient experiencing ventricular dysfunction or heart failure. At least one electrode is located in a region associated with nervous tissue, such as nerve bundles T1-T4, in a patient's body. Electrical stimulation is applied to the at least one electrode to improve the cardiac efficiency of the patient's heart. One or more predetermined physiologic parameters of the patient are monitored, and the electrical stimulation is adjusted based on the one or more predetermined physiologic parameters.

SUMMARY OF THE INVENTION

Aspects of the invention, in some embodiments thereof, relate to electrical neuro-stimulation for modulating cardiovascular functions.

Thus, according to an aspect of some embodiments, there is presented a system for increasing the HRV of a subject. The system comprises a control module and at least one neuro-stimulation unit, functionally associated with the control module and configured to generate an electrical neuro-stimulation comprising stimulation signals. The system further comprises at least two electrodes, configured to be removably attachable onto the skin of the subject. Each electrode is electrically connected to one of the at least one neuro-stimulation unit, and thereby configured to deliver the electrical neuro-stimulation signal to the skin.

The control module is configured to obtain occurrence times of reference points associated with heart beats of the subject. The control module is further configured to controllably determine parameters of the stimulation signal generated by the neuro-stimulation unit. The stimulation parameters are determined such as to synchronize the stimulation signal with the occurrence times.

The system is configured to apply one of the stimulation signals via the first electrode proximately to an acupoint not associated with cardiovascular function, and thereby to increase the HRV of the subject.

According to some embodiments, the acupoint not associated with cardiovascular function is selected from the group consisting of left Sp6 acupoint, right Sp6 acupoint, left Ki6 acupoint, right Ki6 acupoint, left St36 acupoint, right St36 acupoint, left Lv14 acupoint, right Lv14 acupoint, Cv12 acupoint, left St32 acupoint, right St32 acupoint, left Lv3 acupoint, right Lv3 acupoint, left Li4, and right Li4 acupoint.

According to some embodiments, the system is further configured to apply one of the stimulation signals via the second electrode proximately to an acupoint associated with cardiovascular function. According to some embodiments, the acupoint associated with cardiovascular function is selected from the group consisting of the left Ht7 acupoint, right Ht7 acupoint, left Pc6 acupoint, right Pc6 acupoint, left Gb34 acupoint, right Gb34 acupoint, left Ub14 acupoint, right Ub14 acupoint, left Ub15 acupoint, right Ub15 acupoint, left HUA T4 acupoint, right HUA T4 acupoint, left HUA T5 acupoint, right HUA T5 acupoint, and Cv17 acupoint.

According to some embodiments, the control module is further configured to receive a heart activity signal indicative of temporal heart activity of the subject and to identify reference points in the heart activity signal, thereby obtaining the occurrence times of the reference points associated with the heart beats of the subject. According to some embodiments, the heart activity signal is an ECG signal. According to some embodiments, the reference points are indicative of occurrence times of R peaks of heart beats of the subject.

According to some embodiments, the stimulation signal comprises pulses synchronized with the occurrence times of the reference points. According to some embodiments, the pulses have a pulse width smaller than 1 msec and a maximum voltage intensity smaller than 60 V. According to some embodiments, the pulses are biphasic pulses. According to some embodiments, each pulse is delayed relative to a preceding R peak by a time delay between about 100 msec and about 500 msec.

According to some embodiments, the system comprises at least two electrode pairs. According to some embodiments, the at least two electrodes are embedded on patches, the patches being configured to be removably attachable onto the skin.

According to some embodiments, each of the patches has one of the at least one neuro-stimulation unit accommodated therein. For example, patches accommodate stimulation units, respectively. According to some embodiments, each of the patches further accommodates a wireless receiver functionally associated with said neuro-stimulation unit accommodated on said patch. According to some embodiments, the receiver is a transceiver.

According to some embodiments, the at least one neuro-stimulation unit consists of a single neuro-stimulation unit and the electrodes on the patches are wired thereto.

According to some embodiments, the patches further accommodate a sensor functionally associated with the control module and configured to measure at least one physiological parameter of the subject. According to some embodiments, the sensor is selected from the group consisting of an IR sensor for measuring heart-rate, an accelerometer for measuring heart-rate, an impedance meter for measuring skin electrical resistance, a surface EMG sensor for measuring muscle activity and degree of contraction, a blood-pressure sensor, and a thermometer for measuring skin temperature. According to some embodiments, the control module is configured to vary a maximum intensity and/or amplitude of stimulation signals according to a physiological parameter measured by the sensor.

According to an aspect of some embodiments, there is presented a method for increasing the HRV of a subject. The method comprises delivering electrical neuro-stimulation at at least one core acupoint pair by applying an electrical stimulation signal at the acupoints. The core acupoint pair comprises a first acupoint associated with cardiovascular function and a second acupoint not associated with cardiovascular function.

According to some embodiments, the electrical neuro-stimulation is delivered by a first pair of electrodes applying a first electrical stimulation signal at the acupoints. A first electrode of the pair is attached onto the skin of the subject proximately to the first acupoint and the second electrode of the pair is attached onto the skin of the subject proximately to the second acupoint.

According to some embodiments, the electrical neuro-stimulation is delivered by two pairs of electrodes. A first electrode pair is attached onto the skin of the subject proximately to the first acupoint, applying a first electrical stimulation signal at the first acupoint. The second electrode pair is attached onto the skin of the subject proximately to the second acupoint, applying a second electrical stimulation signal at the second acupoint.

According to some embodiments, the first signal applied at the first acupoint and the second signal applied at the second acupoint comprise repetitive pulses at an equal repetition rate, and the pulses of the first signal are substantially simultaneous with the pulses of the second signal.

According to some embodiments, the first signal applied at the first acupoint and the second signal applied at the second acupoint comprise repetitive pulses at an equal repetition rate, and the pulses of the first signal are partially simultaneous with the pulses of the second signal.

According to some embodiments, the first signal and the second signal comprise repetitive pulses at an equal repetition rate, and the pulses of the first signal do not overlap with the pulses of the second signal.

According to some embodiments, the method of claim further comprises delivering electrical neuro-stimulation by a second pair of electrodes applying a second electrical stimulation signal at a second core acupoint pair. A first electrode of the second pair is attached onto the skin of the subject proximately to a first acupoint of the second acupoint pair and the second electrode of the second pair is attached onto the skin of the subject proximately to a second acupoint of the second acupoint pair.

According to some embodiments, the first signal applied at the first core acupoint pair and the second signal applied at the second core acupoint pair comprise repetitive pulses, and the pulses of the first signal are simultaneous with the pulses of the second signal.

According to some embodiments, the first signal applied at the first core acupoint pair and the second signal applied to the second core acupoint pair comprise repetitive pulses, and the pulses of the first signal are partially simultaneous with the pulses of the second signal.

According to some embodiments, the first signal and the second signal comprise repetitive pulses, and the pulses of the first signal do not overlap with the pulses of the second signal.

Certain embodiments of the present invention may include some, all, or none of the above advantages. Further advantages may be readily apparent to those skilled in the art from the figures, descriptions, and claims included herein. Aspects and embodiments of the invention are further described in the specification hereinbelow and in the appended claims.

Unless otherwise defined, all technical and scientific terms used herein have the same meaning as commonly understood by one of ordinary skill in the art to which this invention pertains. In case of conflict, the patent specification, including definitions, governs. As used herein, the indefinite articles "a" and "an" mean "at least one" or "one or more" unless the context clearly dictates otherwise.

Embodiments of methods and/or devices herein may involve performing or completing selected tasks manually, automatically, or a combination thereof. Some embodiments are implemented with the use of components that comprise hardware, software, firmware or combinations thereof. In some embodiments, some components are general-purpose components such as general purpose computers or processors. In some embodiments, some components are dedicated or custom components such as circuits, integrated circuits or software.

For example, in some embodiments, some of an embodiment may be implemented as a plurality of software instructions executed by a data processor, for example which is part of a general-purpose or custom computer. In some embodiments, the data processor or computer may comprise volatile memory for storing instructions and/or data and/or a non-volatile storage, for example a magnetic hard-disk and/or removable media, for storing instructions and/or data. In some embodiments, implementation includes a network connection. In some embodiments, implementation includes a user interface, generally comprising one or more of input devices (e.g., allowing input of commands and/or parameters) and output devices (e.g., allowing reporting parameters of operation and results).

BRIEF DESCRIPTION OF THE FIGURES

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

In the Figures:

FIG. 1a schematically depicts an embodiment of an electrical neuro-stimulation system;

FIG. 1b schematically depicts a cross-sectional side-view of transcutaneous patch of the system of FIG. 1a;

FIG. 1c schematically depicts a cross-sectional side-view of a percutaneous patch according to an alternative embodiment of the system of FIG. 1a;

FIG. 4b schematically depicts a cross-sectional side view of a transcutaneous wireless patch of the system of FIG. 4a;

FIG. 4c schematically depicts a cross-sectional side-view of a percutaneous wireless patch according to an alternative embodiment of the system of FIG. 4a;

DETAILED DESCRIPTION OF SOME EMBODIMENTS

Figure 2A:
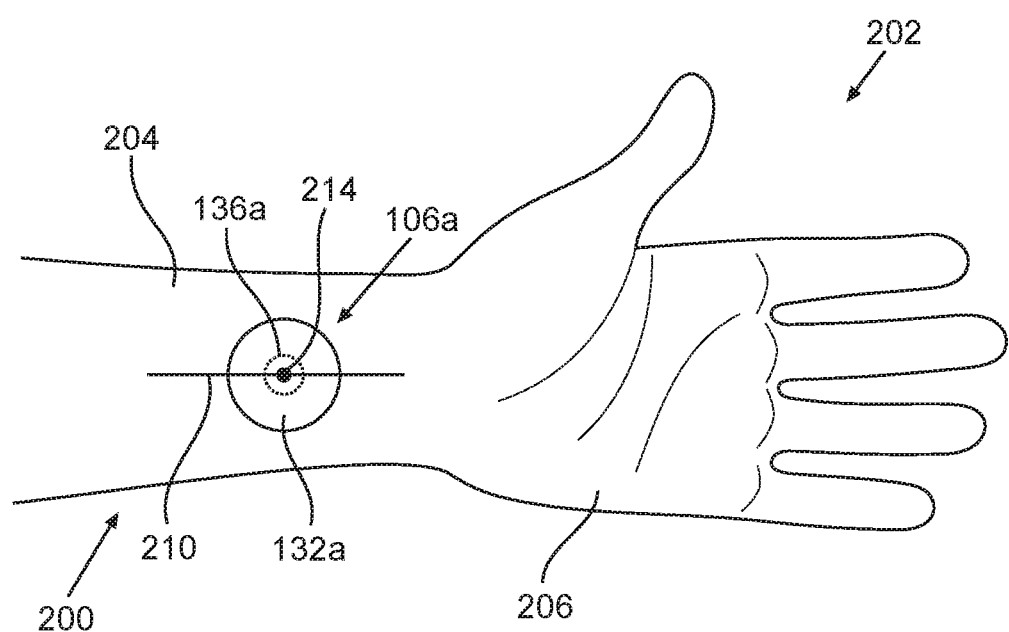
FIG. 2a schematically depicts a placement of the transcutaneous patch of FIG. 1b proximately to an acupoint on a left forearm.

The principles, uses and implementations of the teachings herein may be better understood with reference to the accompanying description and figures. Upon perusal of the description and figures present herein, one skilled in the art is able to implement the teachings herein without undue effort or experimentation. In the figures, like reference numerals refer to like parts throughout.

Definitions

As used herein, "HRV improvement" may refer to an increase in HRV, as elaborated on hereinbelow. HRV improvement may refer to long-term HRV improvement, i.e. a substantial increase in HRV, which is sustained over long periods of time, such as days, weeks, or even months. HRV improvement may also refer to short-term or temporary HRV improvement, wherein a substantial increase in HRV which is sustained for minutes, hours, or even days. Long-term and short-term improvement of HRV may be achieved by applying the systems and methods disclosed herein, as taught hereinbelow.

An acupoint termed "central" is located on a midsagittal plane of a human body (i.e. a plane which divides a human body into a left half thereof and a right half thereof). In a pair of acupoints termed "semi-central" only one of the acupoints is central. In a "central" pair of acupoints, both acupoints are central.

An acupoint termed "left" is located in the left half of a human body. An acupoint termed a "right" is located in the right half of the human body. A pair of acupoints termed "unilateral" are either both left acupoints or both right acupoints. A pair of acupoints termed "bilateral" comprises a left acupoint and a right acupoint.

The term "reciprocal", with reference to two acupoints, or one acupoint being "reciprocal" to another acupoint, refers to bilaterally symmetric acupoints, i.e. the two acupoints being symmetric under reflection about the midsagittal plane. For example, a left Pc6 acupoint and a right Pc6 acupoint are bilaterally symmetric, as are a left Ki6 acupoint and a right Ki6 acupoint. The term "reciprocal", with reference to two pairs of acupoints, or one acupoint pair being "reciprocal" to another pair, refers to a first acupoint in a first pair of the two pairs being reciprocal to a first acupoint in the second of the two pairs, and the second acupoint in the first of the two pairs being reciprocal to the second acupoint in the second acupoint pair.

The term "unilateral", with reference to a positioning of a pair of electrodes, refers to attaching both electrodes onto the same half of the human body, particularly at two acupoints on the same half. In particular, electrodes in a "unilaterally attached" electrode pair are attached onto a unilateral pair of acupoints, respectively.

The term "bilateral", with reference to a positioning of a pair of electrodes, refers to attaching one electrode of the pair onto the left half of the human body, particularly at a left acupoint, and attaching the other electrode of the pair onto the right half of the human body, particularly, at a right acupoint. In particular, electrodes in a "bilaterally attached" electrode pair are attached onto a bilateral pair of acupoints, respectively.

The term "semi-central", with reference to a positioning of a pair of electrodes, refers to attaching one electrode of the pair onto the human body such as to be located on the midsagittal plane, particularly at a central acupoint, and attaching the other electrode of the pair onto either the left half or the right half of the human body, particularly at left acupoint or at a right acupoint. In particular, electrodes in a "semi-centrally attached" electrode pair when attached onto a semi-central pair of acupoints, respectively.

The term "central", with reference to a positioning of a pair of electrodes, refers to attaching the two electrodes of the pair onto the human body such that both are located on the midsagittal plane, particularly at two central acupoints, respectively, In particular, two electrodes are "centrally attached" when attached onto a central pair of acupoints, respectively.

The term "stimulation signal", with reference to electrical neuro-stimulation, refers to a voltage/current signal applied between a pair of electrodes. The term "stimulation parameters", with reference to a stimulation signal, refers to parameters characterizing the stimulation signal, including duration, amplitude, maximum intensity, frequency, and waveform of the stimulation signal, as well as waveforms and inter-pulse time intervals when the stimulation signal comprises a series of pulses. "Stimulation parameters" may also be used to refer to sets of stimulation parameters characterizing different stimulation signals applied between pairs of electrodes parameters characterizing the synchronization of the stimulation signals with respect to one another.

The term "stimulation session goal", with reference to an electrical neuro-stimulation session, refers to an objective of the stimulation session, e.g. improving an efficacy of a physical work out, improving sleep, long-term HRV improvement, treatment of a cardiac arrhythmia by increasing HRV.

The term "stimulation algorithm", with reference to an electrical neuro-stimulation session, refers to a set of instructions for delivering electrical neuro-stimulation. A stimulation algorithm may depend on a respective stimulation session goal. The stimulation algorithm comprises sets of stimulation parameters, each set characterizing a respective stimulation signal corresponding to a respective electrode pair. The stimulation algorithm further comprises the order of application of the stimulation signals, instructions for synchronizing the delivery of the stimulation signals relative to one another or to one or more external signals (e.g. an ECG signal). The stimulation algorithm may also comprise instructions for adjusting the stimulation signals during the stimulation session based on data indicative of values of monitored physiological parameters of the subject.

The term "session data", with reference to an electrical neuro-stimulation session, refers to information regarding the stimulation session, including the stimulation session goal and the associated stimulation algorithm, any adjustments made to stimulation signals during the session, and values of physiological parameters measured before, during, and/or after the stimulation session.

The term "personal data", with reference to electrical neuro-stimulation session/sessions, refers to personal data of a subject, undergoing the stimulation session/sessions, which may be of relevance for determining the stimulation algorithms corresponding to respective stimulation session goals. Personal data may comprise age, gender, medical history, and heart related symptoms, and possibly information regarding the subject's physical activity regimen, smoking habits, diet, and/or the like.

Electrical Neuro-Stimulation System for Improving HRV

A first embodiment of the invention, according to an aspect thereof, is schematically depicted in FIGS. 1a-3e. FIGS. 1a-1b schematically depict a system 100 for delivering electrical neuro-stimulation to a subject (e.g. a person). System 100 comprises a customized controller 102, and a first patch pair 104 including a first patch 106a and a second patch 106b. Controller 102 comprises a control module 120, an electrical neuro-stimulation unit 122, and a user control interface 124. Neuro-stimulation unit 122 and user control interface 124 are functionally associated with control module 120.

Neuro-stimulation unit 122 is configured to deliver electrical neuro-stimulation to a subject, by applying stimulation signals (e.g. voltage signals) between electrodes embedded in/on first patch 106a and second patch 106b, respectively, as elaborated on hereinbelow. Control module 120 controls neuro-stimulation unit 122, i.e. the application of the stimulation signals, as elaborated on hereinbelow. According to some embodiments, control module 120 comprises a processing circuitry 126, a memory circuitry 128, and an internal clock/timer (not shown). According to some embodiments, processing circuitry 126 may comprise a CPU, an application specific integrated circuitry (ASIC), a programmable processing circuitry such as an FPGA, firmware, and/or the like. According to some embodiments, memory circuitry 128 may comprise a volatile memory (e.g. a RAM) and/or a non-volatile memory (e.g. a hard disk, a removable flash drive). According to some embodiments, control module 120 may further comprise at least one analog to digital electrical signal convertor and/or at least one digital to analog electrical signal convertor (all not shown).

Neuro-stimulation unit 122 comprises an electrical signal generator (not shown). According to some embodiments, neuro-stimulation unit 122 may be an analog signal generator, a digital signal generator, a function generator, a waveform generator, and/or the like. Neuro-stimulation unit 122 may further comprise a voltmeter, an ammeter, a resistivity meter, a multi-meter, and/or the like (all not shown). According to some embodiments, control module 120 may include only an elementary electronic circuit (not shown) configured, for example, to instruct neuro-stimulation unit 122 to modify the amplitude, and/or the frequency of a generated stimulation signal, or even just to start, stop, or pause the delivery of electrical neuro-stimulation.

User control interface 124 comprises one or more input devices (not shown) allowing to input information, e.g. personal data of a subject, and commands, e.g. select a stimulation session goal. Commands entered into user control interface 124 are conveyed to control module 120, which is configured to proceed with the implementation thereof. Information entered into user control interface 124 is conveyed to control module 120 and may be stored in memory circuitry 128. User control interface 124 further comprises one or more output devices (not shown) allowing to present data received from control module 120, e.g. sensor-obtained data indicative of values of monitored physiological parameters. According to some embodiments, user control interface 124 comprises a display (not shown). According to some embodiments, the display is a touch screen. According to some embodiments, user control interface 124 may comprise knobs and/or buttons (not shown). According to some embodiments, user control interface 124 may comprise a speaker and/or a microphone, and/or a voice-user interface (not shown). Controller 102 may be powered by a rechargeable battery and/or by an external power source (not shown).

First patch 106a comprises a first patch body 130a, a first patch outer face 132a (shown in FIG. 1b), a first patch inner face 134a, and a first electrode 136a. First electrode 136a is embedded in/on first patch inner face 134a, such that a first electrode external surface 138a is exposed. Second patch 106b comprises a second patch body 130b, a second patch outer face 132b (shown in FIG. 2b), a second patch inner face 134b, and a second electrode 136b. Second electrode 136b is embedded in/on second patch inner face 134b, such that a second electrode external surface 138b is exposed. According to some embodiments, first patch 106a and second patch 106b each consist of one respective electrode, e.g. first electrode 136a and second electrode 136b, respectively.

First patch 106a and second patch 106b are connected via a first conduction cable 152a and via a second conduction cable 152b, respectively, to controller 102 (and thereby electrically connected to neuro-stimulation unit 122). Conduction cables 152a and 152b may be permanently connected to controller 102 and/or permanently connected to first patch 106a and second patch 152b, respectively. Additionally or alternatively, conduction cables 152a and 152b may be configured to detachably connect to controller 102 and/or to first patch 106a and to second patch 152b, respectively, via plug or a socket (both not shown here). When connected to first patch 106a, first conduction cable 152a is electrically associated with first electrode 136a, and likewise, when connected to second patch 106b, second conduction cable 152b is electrically associated with second electrode 136b.

Patches 106a and 106b are configured to be removably attached onto the skin of a subject (e.g. a person) so that dermal contact is established between first electrode 136a and second electrode 136b, respectively, and the subject's skin. As used herein, "dermal contact" between an electrode (or any conductor), and a subject's skin may refer to any direct or indirect (e.g. using a suitable gel) electrically conducting contact between the electrode and the skin. According to some embodiments, such dermal contact may be established via first electrode external surface 138a and via second electrode external surface 138b, respectively. For example, first patch inner face 134a and second patch inner face 134b may be adhesive such as to allow first patch 106a and second patch 106b, respectively, to be removably attached onto the skin. First patch 106a and second patch 106b may be substantially identical or may differ, e.g. in size and shape. The size and shape of the patch bodies may depend on physical characteristics of respective target regions on a subject's body whereunto the patches are configured to be attached, e.g. a thickness of the skin, a proximity of a target acupuncture point (acupoint) and/or a target nerve to the skin's surface, as elaborated on hereinbelow. First patch 106a and second patch 106b may also differ in the number and types of additional components, which they may comprise (i.e. beyond the electrodes), as detailed hereinbelow.

According to some embodiments, each of first patch 106a and second patch 106b may be a wearable item, such as a band, a belt, a glove, a sock, and/or a shirt. The wearable item is configured to be attached onto the skin by being worn about a target body part, such as to establish dermal contact between the electrode embedded therein/thereon (e.g. first electrode 136a or second electrode 136b) and the skin on the target body part, and such that the electrode is positioned proximately to a target acupoint. According to some embodiments, each of first patch 106a and second patch 106b may be an elastic and/or fastenable band, configured to be worn about one or more body parts, such as an arm, a leg, or the torso and the chest.

According to some embodiments, first patch 106a comprises a first sensor 162a, and second patch 106b comprises a second sensor 162b (optional elements, such as sensors 162a and 162b, are depicted in FIGS. 1a and 1b with dashed lines). Each of sensors 162a and 162b may be, for example, an LED sensor for measuring heart-rate, an accelerometer for measuring heart-rate, an impedance meter for measuring skin electrical resistance, an electromyographic (EMG) sensor for measuring muscle activity and degree of contraction, a blood pressure sensor, and/or a thermometer for measuring skin temperature. For example, first sensor 162a may be a heart-rate sensor and a second sensor in first patch 106a may be a muscle contraction sensor. According to some embodiments, first patch 106a and second patch 106b may comprise additional sensors (not shown). The sensors may be electrical, magnetic, mechanical (e.g. measuring pressure), and/or optical (e.g. laser-based). Sensors sufficiently small as to be housed within patches as described hereinabove (e.g. patches 106a and 108a) are known in the art. For example, Samsung's Simband comprises a watchband, in which different sensors are housed, such as a bio-impedance sensor, which obtains the heart-rate by measuring variations in impedance incurred by the pulse wave of blood flow in an artery, and a photoplethysmogram sensor, which detects blood-volume change at the microvascular level by projecting light into a target body region and measuring the change in absorption. [http://www.simband.io/documentation/sensor-module-documentation/simsense/]. Athos provides wearable gear (i.e. shirts and pants) comprising heart-rate sensors and muscle contraction sensors. The muscle contraction sensors are based on EMG technology [https://www.liveathos.com/].

Sensors 162a and 162b are each connected/detachably connected to controller 102 via a first sensor conducting wire 166a and a second sensor conducting wire 166b, and are thereby functionally associated with control module 120 and may thereby be powered. Sensors 162a and 162b are configured to send sensor-obtained data to control module 120.

Controller 102 may further comprise a communication unit 170 for connecting to the internet via an internet connection port (not shown) and/or via wireless transmission in embodiments wherein communication unit 170 is wireless (e.g. comprises a Wi-Fi transceiver (not shown)). Communication unit 170 is functionally associated with control module 120, and may communicatively associate control module 120 with online databases and servers, thereby allowing, for example, to download software updates for software installed in control module 120, to obtain records of a subject's medical history from his healthcare provider, and so on, as further detailed hereinbelow. Substantially similar communication capabilities with the Internet may be incorporated in all the systems described herein.

According to some embodiments, system 100 comprises a second patch pair 180, essentially similar to first patch pair 104, including a third patch 106c and a fourth patch 106d. Similarly to patch pair 104, third patch 106c and fourth patch 106d are connected/detachably connected to controller 102 via a third conduction cable 152c and a fourth conduction cable 152d. According to some embodiments, system 100 may comprise one, two, five, ten, or even twenty or more additional patch pairs, essentially similar to first patch pair 104. According to some embodiments, system 100 comprises an odd number of electrodes. For example, system 100 may comprise only three electrodes: electrodes 136a and 136b and a third electrode 136c embedded in/on third patch 106c.

FIG. 1c shows an embodiment of a percutaneous patch 190. Percutaneous patch 190 differs from first patch 106a in comprising a percutaneous electrode 192 instead of first electrode 136a. The shape and length of percutaneous electrode 192 may depend on the target region whereunto percutaneous patch 190 is configured to be attached, particularly, the proximity of a target acupoint and/or a target nerve to the skin's surface. According to some embodiments, system 100 comprises only percutaneous patches, such as patch 190 or patches essentially similar thereto. According to some embodiments, system 100 may comprise both percutaneous patches and transcutaneous patches, i.e. patches such as patch 106a, which do not include a percutaneous electrode.

Figure 2B:
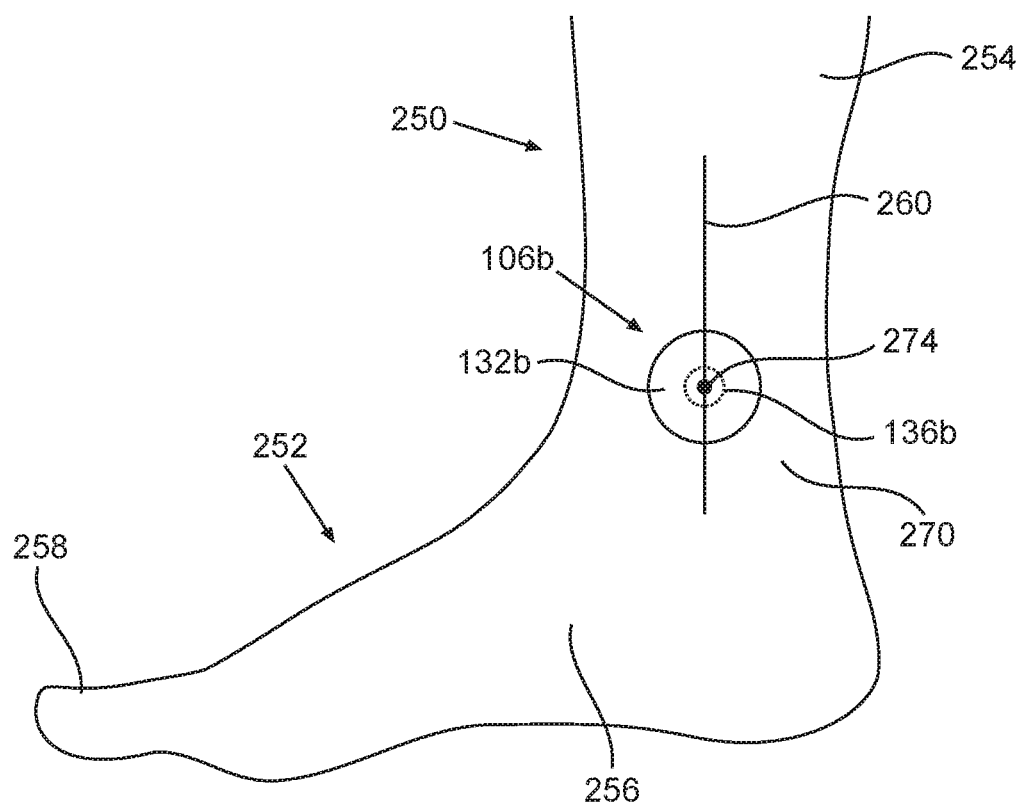
FIG. 2b schematically depicts a placement of the transcutaneous patch of FIG. 1b proximately to an acupoint on a right ankle.

FIGS. 2a and 2b show a possible placement of first patch 106a and second patch 106b on a pair of target regions on a subject's skin, according to some embodiments. FIG. 2a depicts a view of a left forearm distal section 200 and an adjoining left hand 202 of the subject, such that a left forearm ventral side 204 and a left palm 206 are visible. A median nerve 210 extends proximally from hand 202 along forearm distal section 200. First patch 106a is attached onto forearm ventral side 204, such that first electrode 136a (electrode 136a is not visible from first patch outer face 132a side and is therefore surrounded by a dotted line) is positioned proximately to a Pc6 acupoint 214, and consequently proximately to median nerve 210. FIG. 2b depicts a sideview of a right leg distal section 250 and an adjoining right foot 252 of the subject, such that a right leg inner side 254 and a right foot inner side 256, comprising a big toe 258, are visible. An ankle tibial nerve 260 (i.e. ankle branch of the tibial nerve) extends proximally from foot 252 along leg distal section 250. Second patch 106b is attached onto a right ankle inner side 270, such that second electrode 136b is positioned proximately to a right Ki6 acupoint 274, and consequently proximately to right ankle tibial nerve 260.

According to some embodiments, neuro-stimulation unit 122 (in FIG. 1a) is configured to allow for generating a voltage between a pair of electrodes electrically associated therewith. According to some embodiments, neuro-stimulation unit 122 is configured to allow for generating a current passing through a pair of electrodes electrically associated therewith and forming therewith a closed circuit. For example, neuro-stimulation unit 122 allows inducing a current through a conduction path extending through the subject's body between electrodes 136a and 136b when patches 106a and 106b are attached onto the body as shown in FIGS. 2a and 2b, respectively. The placement position of first electrode 136a is selected such as to have the conduction path pass through/near a segment of median nerve 210, proximately to left Pc6 acupoint 214, and thereby electrically stimulate median nerve 210. Similarly, the placement position of second electrode 136b is selected such as to have the conduction path pass through/near a segment of right ankle tibial nerve 260, proximately to right Ki6 acupoint 274, and thereby electrically stimulate right ankle tibial nerve 260.

The electrical resistance between two electrodes attached onto the body may depend on the placement of the electrodes thereon, e.g. on the length and on a trajectory of the conduction path between the electrodes, as well as conditions at the attachment regions, such as whether the skin thereat is wet or dry. The electrical resistivity (i.e. specific electrical resistance) in the human body may vary from one body part to another and may also vary considerably from one subject to another. According to some embodiments, neuro-stimulation unit 122 may be configured to automatically adjust the voltage applied between a pair of electrodes attached onto the body such as to achieve a desired current amplitude and/or maximum intensity. As used herein, "maximum intensity" of a stimulation signal refers to the greater between the highest peak and the absolute value of the lowest trough thereof.

Figure 3A:
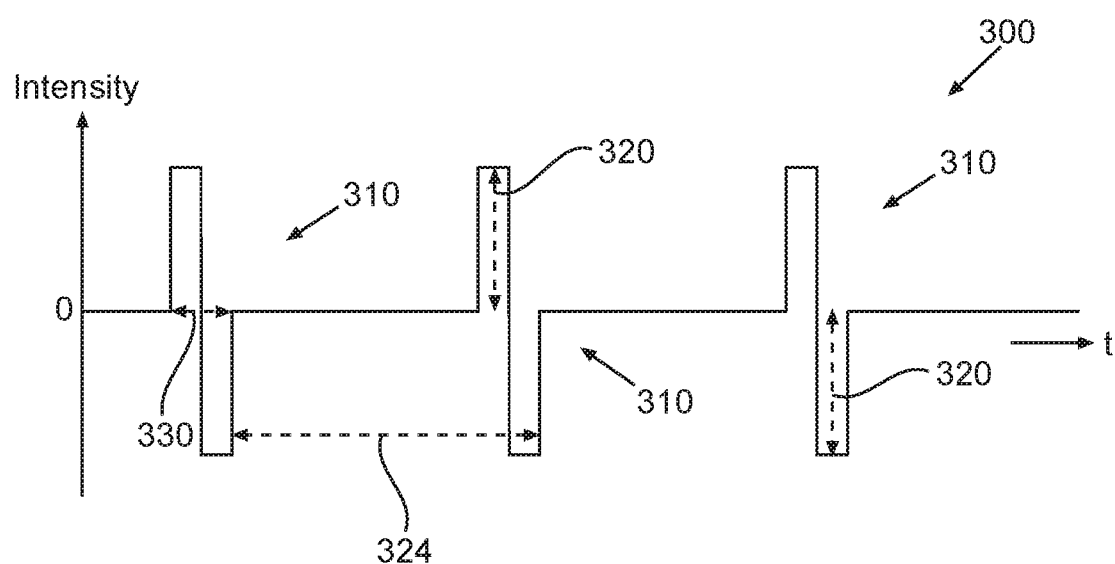
FIG. 3a schematically depicts a stimulation signal.

Making reference to FIG. 3a, according to some embodiments, neuro-stimulation unit 122 is configured to controllably generate an electrical stimulation signal 300 between electrodes 136a and 136b, when the electrodes are attached onto the body, e.g. as in FIGS. 2a and 2b. Stimulation signal 300 comprises a series of stimulation pulses 310. According to some embodiments the stimulation pulses may be biphasic, that is to say that a positive portion of a pulse is followed, substantially immediately, by a negative portion of the pulse According to some embodiments, an area covered by the positive portion is equal to an area covered by the negative portion, thereby preventing/minimizing occurrence of electrolysis (due to the flow of electrical currents through bodily tissue with fluids) when the pulse width is sufficiently narrow, e.g. smaller than 1 msec. According to some embodiments, stimulation pulses 310 are biphasic square wave pulses, i.e. the positive portion and the negative portion are square. According to some embodiments, stimulation pulses 310 are symmetrical biphasic square wave pulses, i.e. the positive portion and the negative portion have the same area and a same width. A pulse amplitude 320 of stimulation pulses 310 may be controllably set to a desired voltage: According to some embodiments, pulse amplitude 320 may be set between 10 to 200 V (Volt), between 60 to 160 V, or even between 100 to 140 V. Additionally or alternatively, a pulse amplitude 320 may be controllably set to a desired current: According to some embodiments, pulse amplitude 320 may be set between 100 μA (micro-Ampere) to 50 mA (milli-Ampere), or between 500 μA to 30 mA, or even between 1 mA to 15 mA. According to some embodiments, a signal frequency of stimulation signal 300, i.e. the reciprocal of an inter-pulse interval 324 between two successive pulses may be controllably set between 0.1 to 200 Hz, or between 0.5 to 30 Hz, or even between 0.5 to 2 Hz. According to some embodiments, a pulse width 330 of each of stimulation pulses 310 may be controllably set between 1 μsec to 50 msec, or between 1 μsec to 2 msec. According to some embodiments, stimulation pulses 310 need not be square waves, and may be, for example, sine-like (e.g. each of the stimulation pulses comprising a single cycle of a sine wave, one half of which is positive, followed by a negative half), or triangular, or saw-tooth waves, etc. According to some embodiments, the stimulation pulses may differ in intensity and/or in waveform. For example, a stimulation signal may comprise a repetition of two square wave pulses, such that a first of the square wave pulses has twice the intensity of the second of the square wave pulses.

According to some embodiments, neuro-stimulation unit 122 is configured to allow for controllably varying stimulation parameters characterizing the stimulation signals, e.g. the duration, amplitude, maximum intensity, frequency, and waveform of the stimulation signals. In particular, neuro-stimulation unit 122 may be configured to allow for controllably generating and modifying stimulation signals, which are continuous, intermittent (applied discontinuously), and which comprise burst pulses (e.g. groups of pulses such that the time intervals between successive groups is comparable to, or significantly longer than, the group duration). Further, neuro-stimulation unit 122 may allow for generating sequences of stimulation pulses, each stimulation pulse in each sequence being applied between electrodes in a different electrode pair. For example, applying a sequence of two stimulation pulses may include applying a first current through a first conduction path comprising first electrode 136a and second electrode 136b, and subsequently applying a second current through a second conduction path comprising third electrode 136c and fourth electrode 136d. The sequence may then be repeated any number of times. As used herein, "series of stimulation pulses" may refer to a group of stimulation pulses making up a stimulation signal. "Sequence of stimulation pulses" or "stimulation sequence" may refer to a group of stimulation pulses applied one after the other by different electrode pairs. "Sequence of stimulation pulses" or "stimulation sequence" may refer also to a number of groups of stimulation pulses (e.g. two, three, four, five, or even ten groups), such stimulation pulses within a group are applied simultaneously, and/or at least partially simultaneously (i.e. such as to partially overlap), and stimulation pulses from different groups are applied one after the other, as elaborated on hereinebelow. Such sequences of stimulation pulses may allow for sequentially delivering electrical neuro-stimulation at different acupoint pairs, as elaborated on hereinbelow and in the Heart-rate variability improvement method section.

Figure 3B:
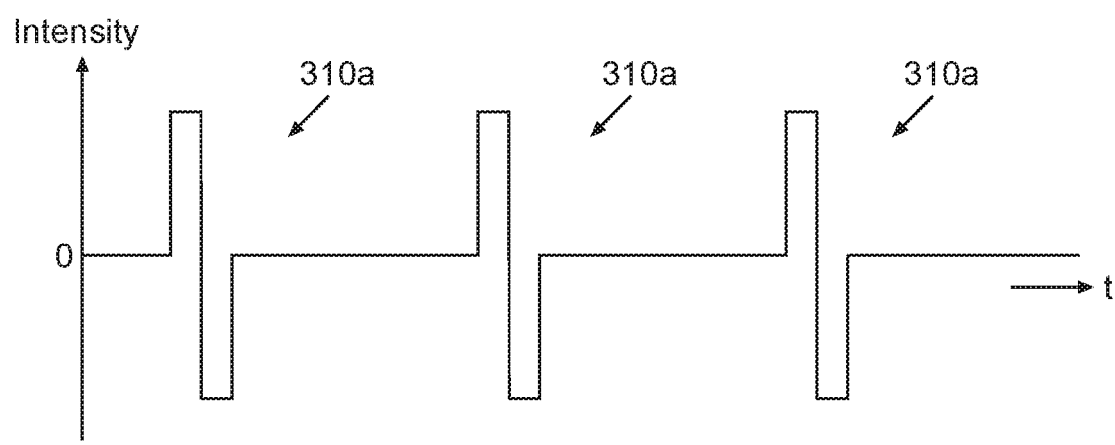
FIG. 3b schematically depicts a pair of temporally shifted stimulation signals.
Figure 3B:
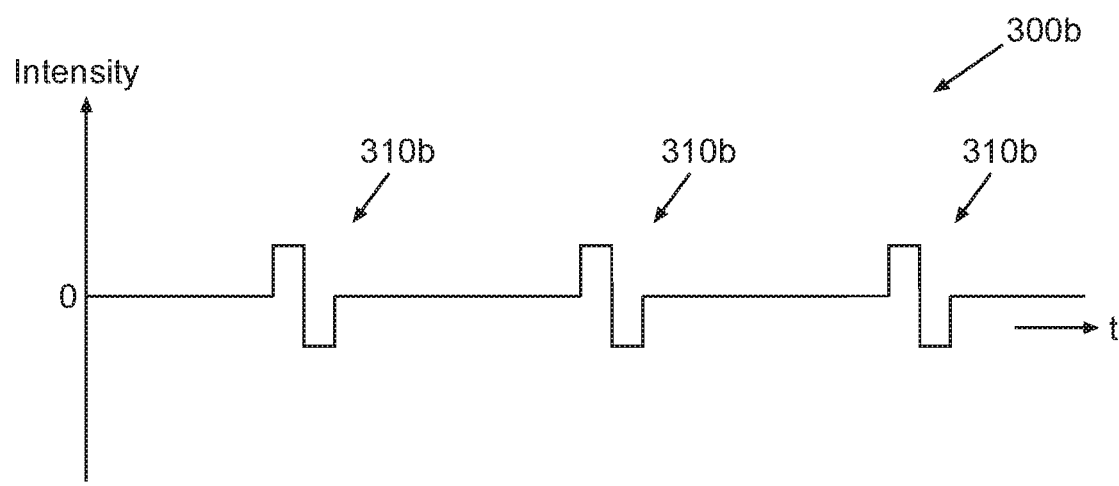

Making reference to FIG. 3b, according to some embodiments, neuro-stimulation unit 122 is configured to generate a first stimulation signal 300a between electrodes of a first electrode pair, and a second stimulation signal 300b between electrodes of a second electrode pair, when the electrodes are attached onto the skin. For example, the first electrode pair may comprise electrodes 136a and 136b, and the second electrode pair may comprise third electrode 136c and fourth electrode 136d. According to some embodiments, first stimulation signal 300a and second stimulation signal 300b are similar to stimulation signal 300, each comprising a series of stimulation pulses 310a and 310b (e.g. square wave, biphasic pulses), respectively. First stimulation signal 300a and second stimulation signal 300b are temporally shifted with respect to one another, such that an onset of each pulse of second stimulation pulses 310b is delayed by 1 μsec to 1 sec or by 10 μsec to 100 msec relative to an onset of a respective pulse of first stimulation pulses 310a. According to some embodiments, stimulation pulses 310a and 310b may differ in amplitude, width, and/or waveform. For example, first stimulation pulses 310a may be sine waves (each stimulation pulse comprising e.g. a single sine wave cycle or a portion thereof or two sine wave cycles, etc.), while second stimulation pulses 310b may be square waves.

Figure 3C:
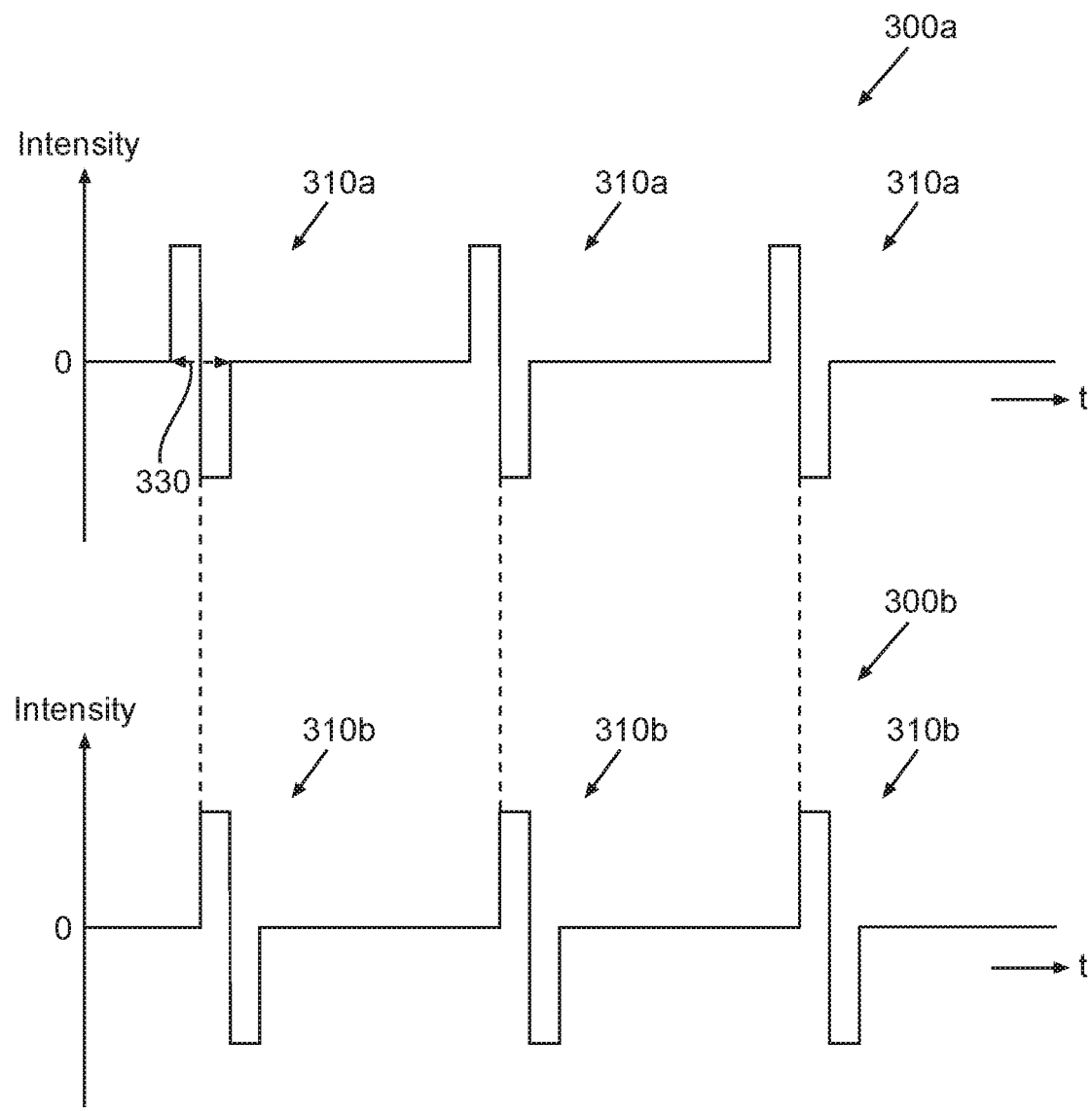
FIG. 3c schematically depicts a pair of partially simultaneous stimulation signals.

According to some embodiments, stimulation pulses 310a and 310b may be partially overlapping. In FIG. 3c each pulse of second stimulation pulses 310b is partially simultaneous with a respective pulse of first stimulation pulses 310a. The onset of each pulse of second stimulation pulses 310b is delayed relative to the onset of a respective pulse of first stimulation pulses 310a by less than a pulse width 330a of first stimulation pulses 310a.

According to some embodiments, neuro-stimulation unit 122 is configured to successively apply n≥3 stimulation pulses between n electrode pairs, one electrode pair after another, i.e. apply an n pulse stimulation sequence. According to some embodiments, neuro-stimulation unit 122 is configured to repeatedly apply the n pulse stimulation sequence, such that the first pulse in each sequence may be delayed, for example, by 1 sec relative to the last pulse in the preceding sequence thereto. According to some embodiments, neuro-stimulation unit 122 is configured to generate n stimulation signals, similar to stimulation signal 300, between n pairs of electrodes, respectively, such that for any m (2≤m≤n) each stimulation pulse of the mth stimulation signal is delayed by 1 μsec to 1 sec or 10 μsec to 100 msec relative to a respective stimulation pulse of the (m−1)th voltage signal. According to some embodiments, the number of pairs n may equal 4, 5, 6, 10, or even 20.

According to some embodiments, a sequence of stimulation pulses may comprise applying some of the stimulation pulses simultaneously and/or at least partially simultaneously. For example, a first stimulation pulse may be applied between a first pair of electrodes, and subsequently a second and third stimulation pulses may be simultaneously or at least partially simultaneously applied between a second and third pair of electrodes, respectively. The sequence may then be repeated. Or, for example, a first pair of stimulation pulses may be simultaneously or at least partially simultaneously applied between a first and a second pair of electrodes, respectively, and subsequently a second pair of stimulation pulses may be simultaneously or at least partially simultaneously applied between the first pair of electrodes and a third pair of electrodes, respectively. The sequence may then be repeated.

According to some embodiments, neuro-stimulation unit 122 may be further configured to repeatedly generate a stimulation cycle, the stimulation cycle comprising a succession of potentially different stimulation sequences. The sequences may differ, for example, in amplitudes and waveforms of the stimulation pulses, as well as in an order that the stimulation pulses are applied between electrodes pairs. Different stimulation sequences in a stimulation cycle may also be applied between different sets of electrodes, i.e. comprising different electrode pairs. For example, a first stimulation sequence comprising two pulses may be applied between a first electrode pair and a second electrode pair, respectively, while a second stimulation sequence comprising two pulses may be applied between a third electrode pair and a fourth electrode pair, respectively. The time delay between a last pulse in a last sequence in a cycle and a first pulse in a first sequence in a successive cycle may be significantly greater than a time delay between successive sequences in a cycle, for example, 1 sec as compared to 1 msec.

It is noted that different electrode pairs need not necessarily be fully distinct, in the sense that two different electrode pairs may share an electrode common to both pairs. For example, a first electrode pair may comprise electrodes 136a and 136b and a second electrode pair may comprise electrode 136a and third electrode 136c. The electrode pairs may be used alternately. Applying a sequence of two stimulation pulses may include inducing a first current through the first conduction path (i.e. comprising first electrode 136a and second electrode 136b), and subsequently inducing a current through another conduction path comprising first electrode 136a and third electrode 136c. The first current may then be applied again, followed by a repeated application of the second current, and so on.

Control module 120 controls neuro-stimulation unit 122 and is configured to send instructions thereto, e.g. to start or stop applying one or more stimulation signals between one or more electrode pairs, respectively, or to adjust the stimulation parameters. According to some embodiments, memory circuitry 128 may store stimulation algorithms corresponding to respective stimulation session goals. Each stimulation algorithm comprises a respective set of stimulation parameters, including the number of electrodes and pairings thereof, the target regions for the placement of the electrodes, as well as stimulation parameters characterizing the stimulation signals corresponding to each of the electrode pairs. According to some embodiments, processing circuitry 126 may comprise loop feedback circuitry (not shown), configured to adjust inputs (e.g. stimulation signals) as a function of outputs (e.g. real-time HRV values). The stimulation algorithms may further comprise instructions for the real-time adjustment of the stimulation signals based on real-time processing of data received from first sensor 162a and/or second sensor 162b (e.g. heart-rate readings, degree of muscle contraction), and/or any other sensor on any other patch, and/or other sensor-obtained data of the subject, e.g. during the application of the stimulation sequence, by a device other than system 100, for example, an ECG monitor. As used herein, "real-time", with reference to data processing, may refer to data processing that is accomplished and generates results, which are possibly used in a decision-making protocol, during that immediate stimulation session. According to some embodiments, real-time data processing and "real-time operations" may be performed within a few seconds after a related input is received, or within less than one second, less than about 0.1 sec, or even less than about 1 msec.

According to some embodiments, session data is saved and stored in memory circuitry 128. Processing circuitry 126 may be installed with machine learning algorithms for analyzing stored session data to adapt the stimulation algorithms to better meet the (objectives of) respective stimulation session goals in future treatments (i.e. stimulation sessions). The machine learning algorithms may be configured for studying the response of monitored physiological parameters, particularly, HRV parameters, to the electrical neuro-stimulation delivered, and for identifying effective sets of stimulation parameters and suggesting improvements thereto, as detailed in the Learning methods for heart-rate variability improvement section hereinbelow.

According to some embodiments, the data received from the sensors is communicated to an online database (via controller 102 internet connection port or Wi-Fi transceiver 170) where it is stored. The data may be further communicated to an associated database computer (installed with customized software) where it is analyzed to determine improved stimulation algorithms for HRV improvement both at the level of the subject and both at the level of a population or subpopulation, as detailed in the Learning methods for heart-rate variability improvement section hereinbelow. According to some embodiments, the real-time data processing is performed on the database computer and adjusted values of the stimulation parameters are communicated back to controller 102.

According to some embodiments, both sensors 162a and 162b are muscle contraction sensors. First sensor 162a is configured to transmit a signal to control module 120 when the detecting that a motor threshold is approached/has been reached in a region near where first electrode 136a is placed. Similarly, second sensor 162b is configured to transmit a signal to control module 120 when detecting that a motor threshold is approached/has been reached in a region near where second electrode 136b is placed. As a safety precaution, on receipt of any of the above-mentioned signals, control module 120 may be configured to instruct neuro-stimulation unit 122 to stop, attenuate, or not further increase the maximum intensity of, the stimulation signal applied between first electrode 136a and second electrode 136b.

According to some embodiments, control module 120 may receive real-time data indicative of temporal heart activity of the subject (e.g. from an external ECG monitor communicatively associated with controller 102). Control module 120 may be configured to process the received data to identify reference points in the data, and respective occurrence times thereof, thereby allowing for synchronizing an onset of each stimulation pulse in a stimulation signal relative to a time of occurrence of a respective reference point. As used herein, two sequences of events may be referred to as being "synchronized" when the time interval between respective events in each of the two sequences is set in advance or determined in real-time according to received real-time data. According to some embodiments, control module 120 may be configured to time the onset of a stimulation pulse such as to occur after the occurrence time of a respective reference point. According to some embodiments, control module 120 may be configured to time the onsets of stimulation pulses in a series of stimulation pulses such as to occur after respective occurrence times of respective reference points. According to some embodiments, control module 120 may be configured to time the onsets of stimulation pulses in a sequence of stimulation pulses such as to occur after respective occurrence times of respective reference points. According to some embodiments, control module 120 may be configured to time the application of intermittent stimulation signals such as to be alternating with the reference points. According to some embodiments, the reference points may be ECG signal R peaks (R peak being the peak of the R wave of the QRS complex characterizing a typical ECG signal) of respective normal heart beats (i.e. non-arrhythmic heart beats). An onset of a stimulation pulse may be configured to be delayed relative to a respective R peak occurrence time. According to some embodiments, the time delay may be fixed, with the onset of the stimulation pulse occurring 100-500 msec or even 200-400 msec after the respective R peak occurrence time. Additionally or alternatively, the time delay may depend on an average of several NN intervals (i.e. the time intervals between successive normal beats), e.g. last five, ten, or even twenty NN intervals, being delayed by a time equal to 10%, 20%, 30%, or even 50% of the average. ("NN interval" refers to the time interval between R peaks of two successive normal beats.)

According to some embodiments, a sequence of pulses may be timed such as to fully occur in a time interval of 400 msec, the time interval beginning 100 msec after a respective R peak occurrence time. According to some embodiments, a cycle of sequences may be timed such as to fully occur in a time interval of 400 msec, the time interval beginning 100 msec after a respective R peak occurrence time. According to some embodiments, each pulse in a sequence is timed such as to fully occur in a time interval of 400 msec, the time interval beginning 100 msec after a respective R peak occurrence time. For example, a first pulse, applied between a electrodes in a first electrode pair, is timed to fully occur in a 400 msec time interval, beginning 100 msec after a first R peak occurrence time, while a second pulse, applied between electrodes in a second electrode pair, is timed to occur in a 400 msec time interval, beginning 100 msec after a second R peak occurrence time, and so on.

Figure 3D:
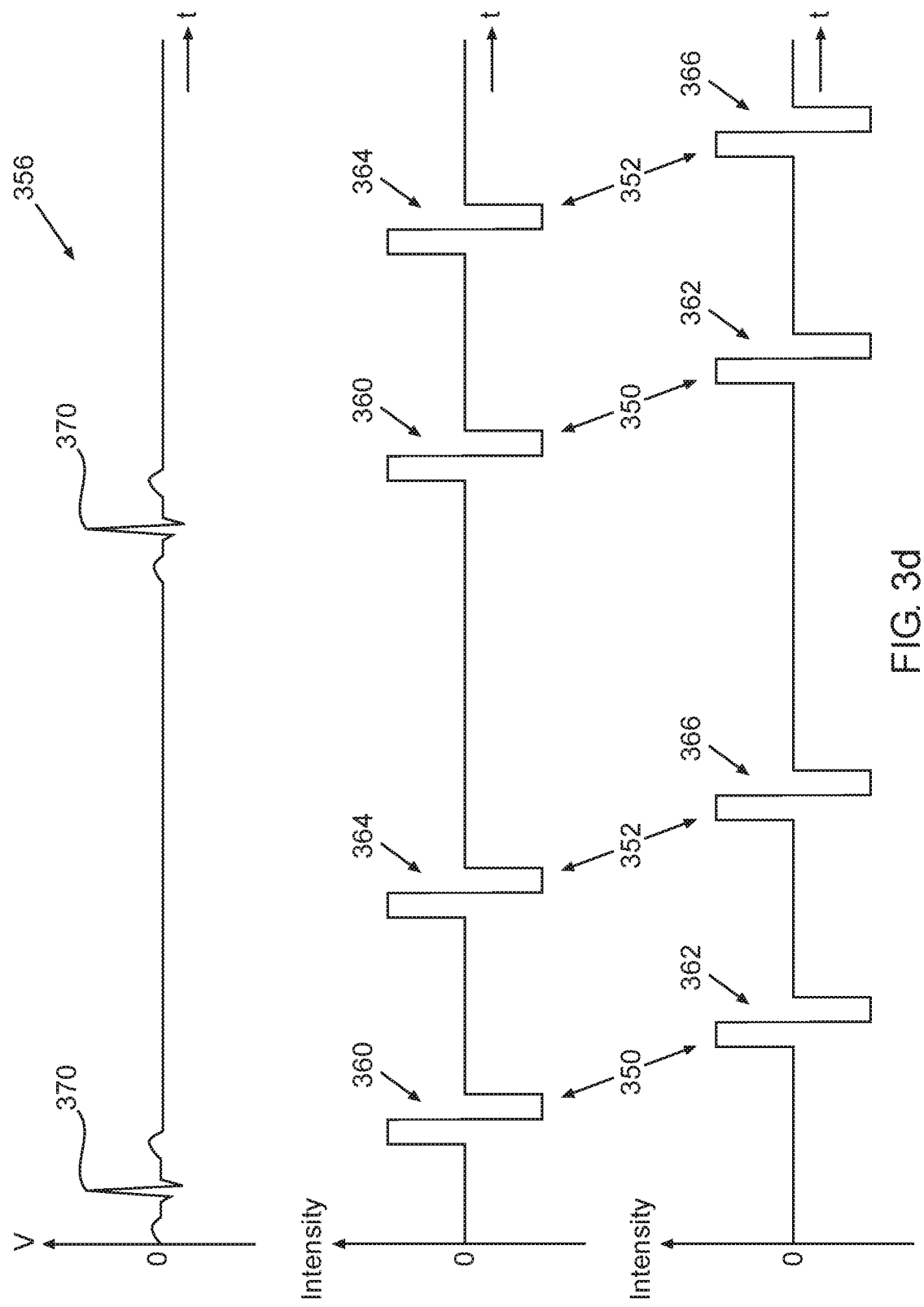
FIG. 3d schematically depicts repeated application of a stimulation cycle synchronized with an ECG signal.

FIG. 3d depicts repeated application of a stimulation cycle of two stimulation sequences synchronized with an ECG signal 356: a first stimulation sequence 350 and a second stimulation sequence 352. First stimulation sequence 350 comprises two pulses: A stimulation pulse 360 applied between first electrode 136a and second electrode 136b, and a stimulation pulse 362 subsequently applied between third electrode 136c and fourth electrode 136d. Second stimulation sequence 352 comprises two pulses: A stimulation pulse 364 applied between first electrode 136a and second electrode 136b, and a stimulation pulse 366 subsequently applied between third electrode 136c and fourth electrode 136d. Stimulation pulses 360, 362, 364, and 366 are similar to stimulation pulse 300, but may differ in amplitude and/or width. Each stimulation cycle may be timed to fully occur in a 400 msec time interval beginning 100 msec after a respective R peak 370 (of a normal beat) occurrence time.

Figure 3E:
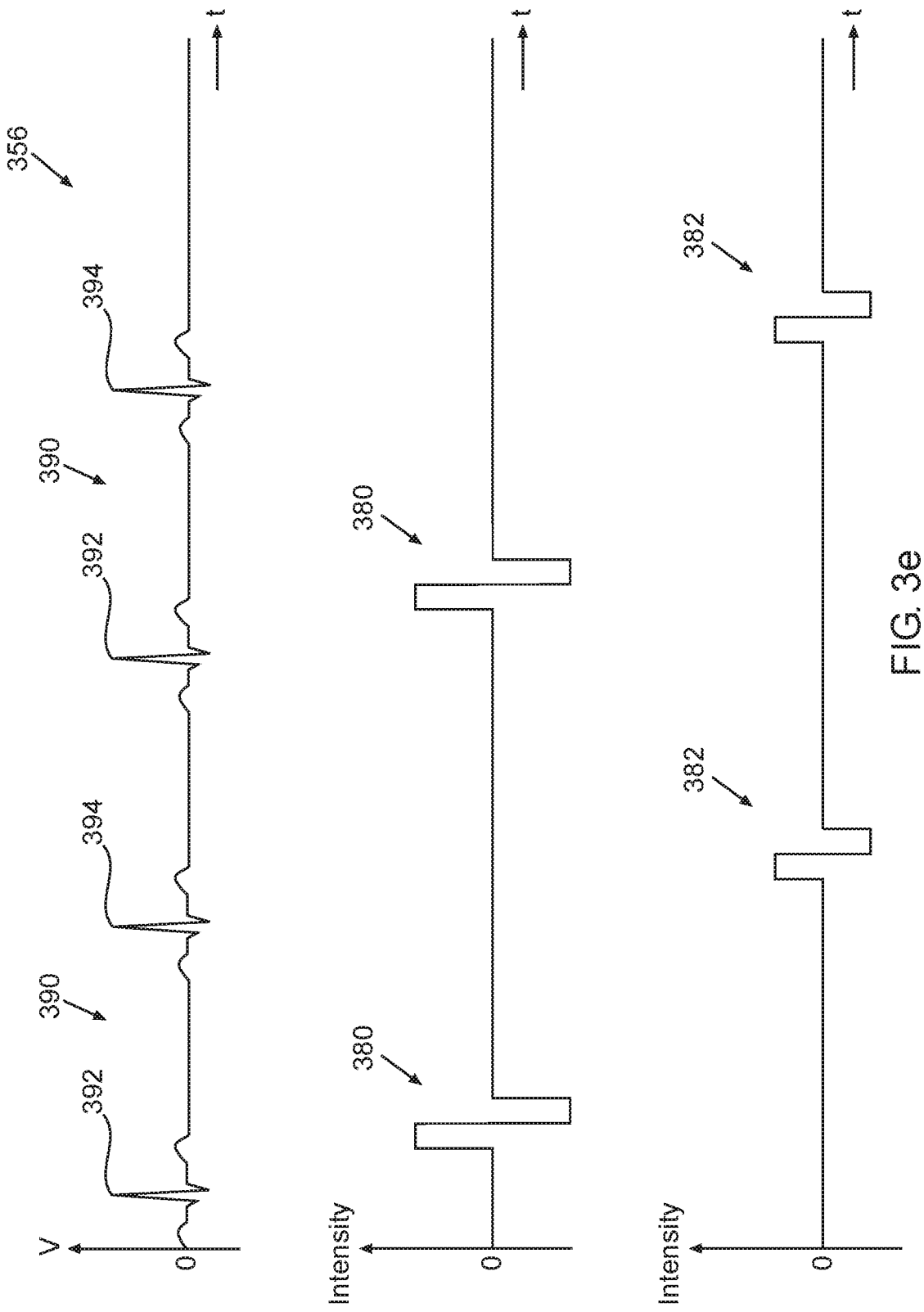
FIG. 3e schematically depicts repeated application of a stimulation sequence synchronized with an ECG signal.

FIG. 3e depicts repeated application of a sequence of two stimulation pulses synchronized with ECG signal 356. Each sequence comprises a first stimulation pulse 380 and a second stimulation pulse 382. Stimulation pulse 380 is applied between first electrode 136a and second electrode 136b, and a stimulation pulse 382 is subsequently applied between third electrode 136c and fourth electrode 136d. Stimulation pulses 380 and 382 are similar to stimulation pulse 300, but may differ in amplitude and/or width. The stimulation pulses are regulated relative to occurrence times of R peak pairs 390 of successive normal beats. An onset of each of stimulation pulses 380 is timed to occur in a respective 400 msec time interval beginning 100 msec after an occurrence time of a first R peak 392 in a respective R peak pair 390, while an onset of each of stimulation pulses 382 is timed to occur in a respective 400 msec time interval beginning 100 msec after an occurrence time of a second R peak 394 in a same respective R peak pair 390.

It is to be understood that the above-mentioned stimulation pulses, signals, sequences, cycles, and algorithms are discussed solely by way of examples of effective treatment for modulating HRV discovered by the inventor. Other electrode arrangements and stimulation parameters, etc., which may be useful for modulating HRV are considered to be within the scope of the present invention.

System 100 may be operated (i.e. controlled) by a trained professional via user control interface 124. According to some embodiments, session data and personal data may be selectively presented on user control interface 124 display. For example, the trained professional may use user control interface 124 input devices to instruct user control interface 124 to display, for example, real-time sensor-obtained data (e.g. heart-rate, blood pressure), values of electrical stimulation parameters characterizing the stimulation signals, and/or the medical history of the subject. User control interface 124 display may further be configured to display other data, such as remaining battery power in embodiments wherein controller 102 is powered by a battery. User control interface 124 input devices allow to start, stop, or pause the delivering of neuro-stimulation, as well as to select a stimulation session goal. User control interface 124 may further allow the trained professional to program a stimulation session, i.e. to assign values to the stimulation parameters, as well as to modify the stimulation parameters during the stimulation session, for example, based on real-time sensor-obtained data (e.g. HRV parameters, blood pressure, degrees of muscle contraction) displayed on user control interface 124 display. User control interface 124 input devices further allow to enter personal data of a subject, which may then be stored in memory circuitry 128 in a directory associated with the subject.

Wireless Electrical Stimulation System for Improving HRV

Figure 4A:
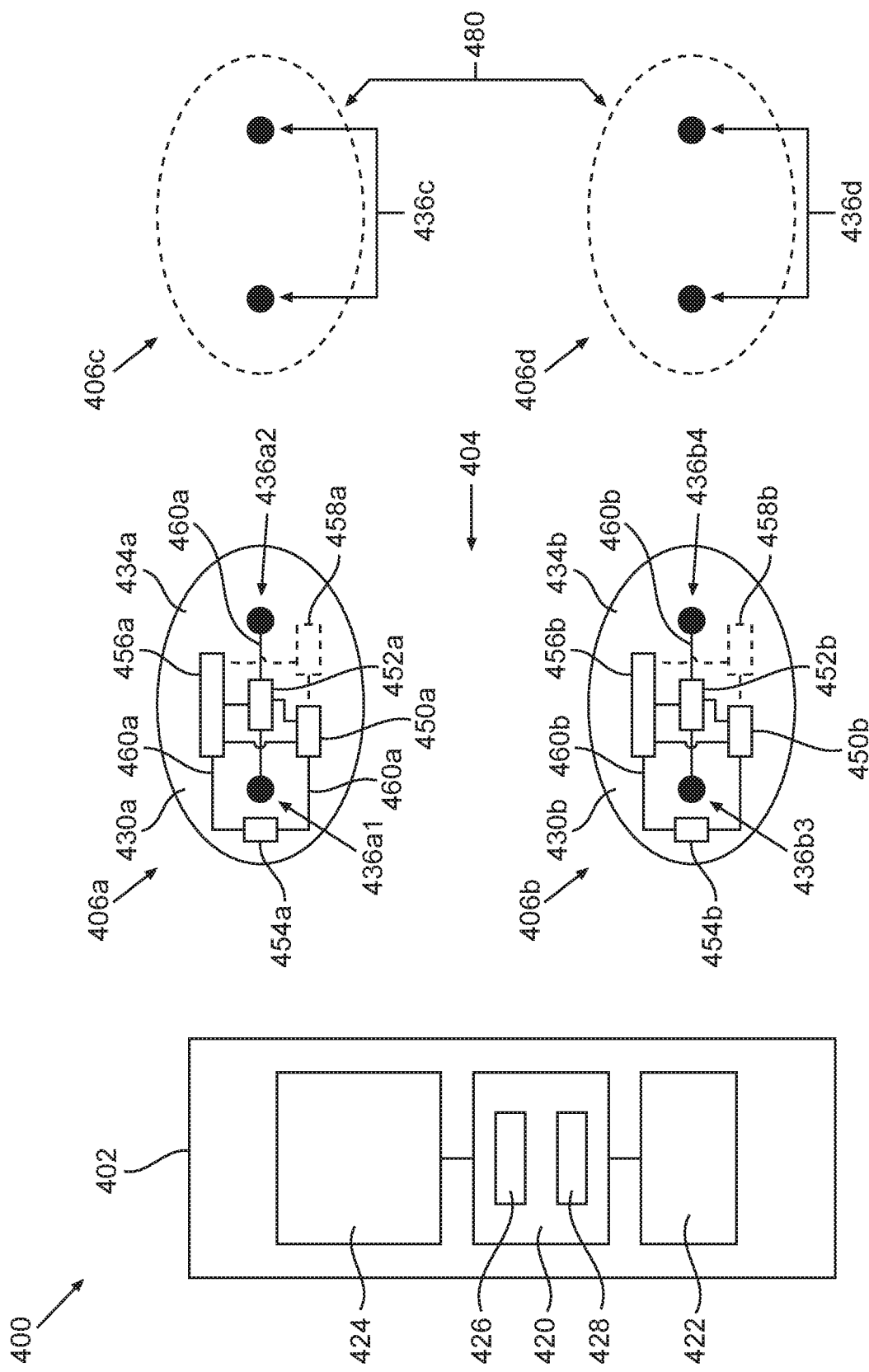
FIG. 4a schematically depicts an embodiment of a wireless electrical neuro-stimulation system.
Figure 4B:
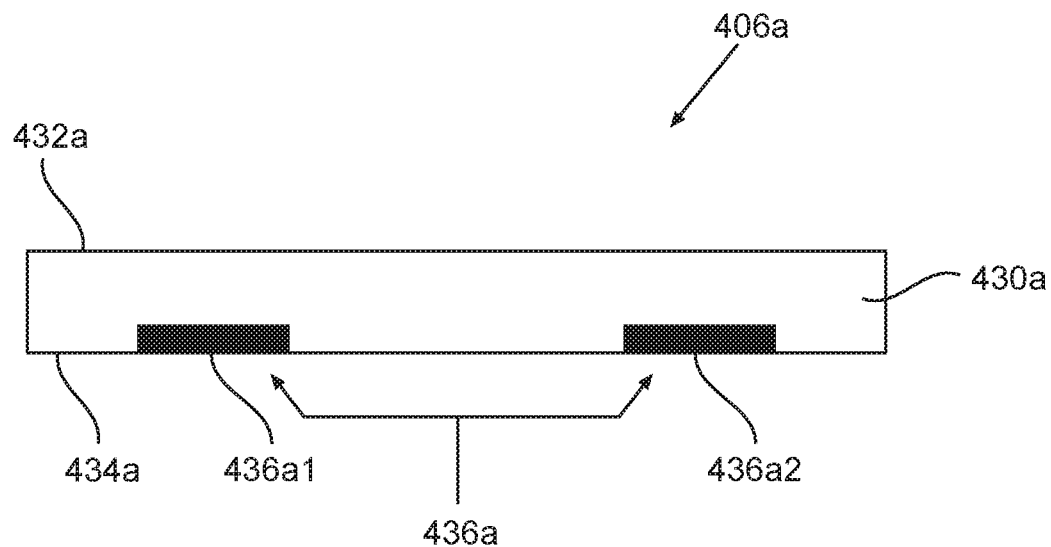

Another embodiment of the invention, according to another aspect thereof, is schematically depicted in FIGS. 4a-6. FIGS. 4a and 4b, schematically depicts a wireless system 400 for delivering electrical neuro-stimulation to a subject. Wireless system 400 comprises a controller 402, and a first wireless patch (WP) pair 404 including a first WP 406a, and a second WP 406b. Wireless system 400 is said to be "wireless" in the sense that the wireless patches, e.g. first WP 406a and second WP 406b, are physically disconnected from any object external thereto, particularly, controller 402. Controller 402 comprises a control module 420, a wireless communication unit 422 supporting Bluetooth technology, NFC technology, Wi-Fi, and/or the like, and a user control interface 424 similar to user control interface 124. Control module 420 is similar to control module 120 and comprises a processing circuitry 426, a memory circuitry 428 and a clock/timer (not shown). Wireless communication unit 422 and user control interface 424 are functionally associated with control module 420.

According to some embodiments, controller 402 may be a smartphone, a tablet, a laptop, a desktop computer, installed with customized software for controlling and communicating with one or more WP pairs, such as WP pair 404, as detailed hereinbelow. According to some embodiments, controller 402 may be a customized device. Controller 402 may be powered by a rechargeable battery and/or by an external power source (not shown).

First WP 406a comprises a first WP body 430a, a first WP outer face 432a (shown in FIG. 4b), a first WP inner face 434a, and a first electrode pair 436a comprising a first electrode 436a1 and a second electrode 436a2. First electrode 436a1 and second electrode 436a2 are each embedded in/on first WP inner face 434a, such as to be partially exposed (in an essentially similar manner to electrodes 136a and 136b). Second WP 406b comprises a second WP body 430*b*, a second WP outer face (not shown), a second WP inner face 434*b*, and a second electrode pair 436*b* comprising a third electrode 436*b*3 and a fourth electrode 436*b*4. Third electrode 436*b*3 and fourth electrode 436*b*4 are each embedded in/on second WP inner face 434*b*, such as to be partially exposed (in an essentially similar manner to electrodes 136*a* and 136*b*).

First WP 406*a* is configured to be removably attached onto the skin of a subject so that dermal contact is established between first electrode 436*a*1 and second electrode 436*a*2, respectively, and the subject's skin (via external surfaces of the electrodes (not indicated), essentially similarly to first electrode 136*a*). For example, first WP inner face 434*a* may be adhesive such as to allow first WP 406*a* to be removably attached onto the skin. Similarly, third electrode 436*b*3 and fourth electrode 436*b*4 are configured to establish dermal contact with the skin when second WP 406*b* is attached thereunto. First WP 406*a* and second WP 406*b* may be substantially identical or may differ, e.g. in a size and a shape of the respective WP bodies and the embedded electrodes. The size and shape of the patch bodies may depend on physical characteristics of respective target regions on the subject's body whereunto the patches are configured to be attached, e.g. a thickness of the skin, a proximity of an acupuncture point and/or a target nerve to the skin's surface, as elaborated on hereinbelow. First WP 406*a* and second WP 406*b* may also differ in a number and types of additional components which they comprise (i.e. beyond the electrodes), as detailed hereinbelow. According to some embodiments, each of first WP 406*a* and second WP 406*b* is a wearable item, similarly to the wearable item embodiments of patches 106*a* and 106*b*.

First WP 406*a* further comprises a control circuitry 450*a*, a neuro-stimulation unit 452*a*, a wireless transceiver 454*a* and a WP battery 456*a*. According to some embodiments, first WP 406*a* may further comprise a WP sensor 458*a*, which may be similar to first sensor 162*a*. According to some embodiments, control circuitry 450*a* may include a processor, a memory, and an internal clock/timer (all not shown), similarly to control module 120. According to some embodiments, control circuitry 450*a* may comprise an elementary electronic circuit (not shown) configured, for example, to instruct stimulation unit 452*a* to modify the amplitude and/or frequency of a generated stimulation signal, or even just to start, stop, or pause the delivery of electrical neuro-stimulation. Stimulation unit 452*a* may comprise analog signal generator, a digital signal generator, a function generator, a waveform generator, and/or the like (all not shown). Stimulation unit 452*a* may further comprise a voltmeter, an ammeter, a resistivity meter, a multi-meter, and/or the like (all not shown). Wireless transceiver 454*a* is configured to send information to, and to receive information from, wireless communication unit 422, for example, via Bluetooth technology, NFC technology, Wi-Fi, and/or the like. WP sensor 458*a* is similar to first sensor 162*a* and may be, for example, a heart-rate sensor, an HRV sensor, a muscle contraction sensor, and/or a blood pressure sensor. According to some embodiments, first WP 406*a* may comprise one or more additional sensors (not shown). For example, WP sensor 458*a* may be a blood-pressure sensor and a second sensor (not shown) in/on first WP 406*a* may be a heart-rate sensor. WP battery 456*a* powers first WP 406*a*, and may be rechargeable and/or replaceable.

Electrical wires 460*a* connect elements in first WP 406*a*. (e.g. control circuitry 450*a*, stimulation unit 452*a*) Particularly, electrical wires 460*a* connect stimulation unit 452*a* to first electrode 436*a*1 and to second electrode 436*a*2, respectively. Stimulation unit 452*a*, wireless transceiver 454*a*, and WP sensor 458*a* are all functionally associated with control circuitry 450*a*, and are configured to transmit information to, and/or receive information from, control circuitry 450*a* (via electrical wires 460*a*).

Wireless transceiver 454*a* and wireless communication unit 422 are communicatively associated and functionally associate control circuitry 450*a* with control module 420. In particular, stimulation unit 452*a* and WP sensor 458*a* are thereby functionally associated with control module 420, and may be controlled via user control interface 424.

Similarly, second WP 406*b* further comprises a control circuitry 450*b*, a stimulation unit 452*b*, a wireless transceiver 454*b*, and a WP battery 456*b*, essentially similar to respective counterparts on first WP 406*a*. According to some embodiments, second WP 408 may further comprise WP sensor 458*b*, which may be similar to WP sensor 458*a*. Second WP 406*b* further comprises electrical wires 460*b*. Control circuitry 450*b*, stimulation unit 452*b*, wireless transceiver 454*b*, WP battery 456*b*, and WP sensor 458*b* (in embodiments where present) are connected/functionally associated in an essentially similar manner as the respective counterparts in first WP 406*a* (e.g. control circuitry 450*a* is the counterpart of control circuitry 450*b*).

According to some embodiments, wireless system 400 comprises a second WP pair 480, essentially similar to first WP pair 404, including a third WP 406*c* and a fourth WP 406*d*. According to some embodiments, beyond WP pairs 404 and 480, wireless system 400 may comprise one, two, five, ten or even twenty or more additional WP pairs (not shown), essentially similar to first WP pair 404. According to some embodiments, wireless system 400 comprises an odd number of WPs. For example, wireless system 400 may comprise only three patches: First WP 406*a*, second WP 406*b*, and third WP 406*c*.

Figure 4C:
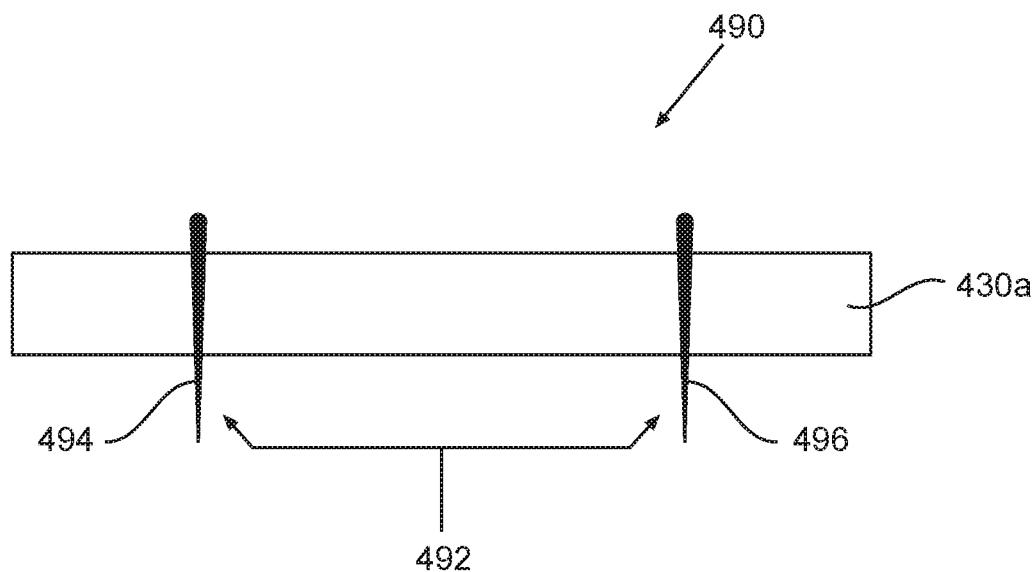

FIG. 4*c* shows an embodiment of a percutaneous WP 490. Percutaneous WP 490 differs from first WP 406*a* in comprising a percutaneous electrode pair 492, including a first percutaneous electrode 494 and a second percutaneous electrode 496, in place of first electrode pair 436*a*. The shape and the length of percutaneous electrodes 494 and 496 may depend on a target region whereunto percutaneous WP 490 is configured to be attached, particularly, a proximity of a target acupoint and/or a target nerve to the skin's surface. According to some embodiments, wireless system 400 comprises only percutaneous WPs, such as percutaneous WP 490, or WPs essentially similar thereto. According to some embodiments, wireless system 400 may comprise both percutaneous WPs and transcutaneous WPs, i.e. WPs such as first WP 406*a* which do not include a percutaneous electrode.

Figure 5A:
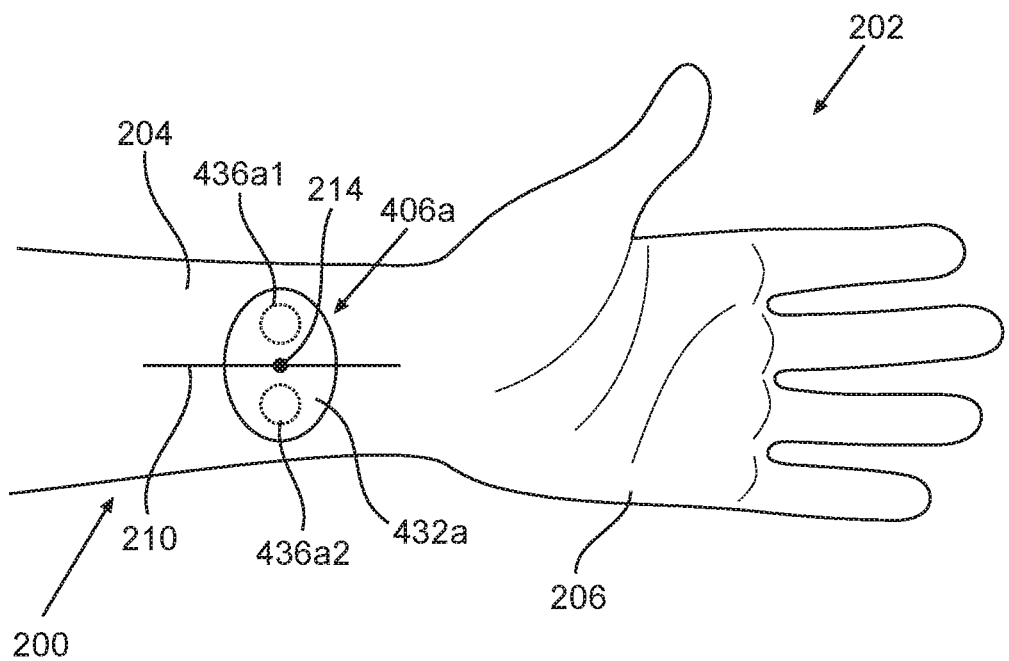
FIG. 5a schematically depicts a placement of the transcutaneous patch of FIG. 4b proximately to an acupoint on a left forearm in a transverse-electrode attachment configuration.
Figure 5B:
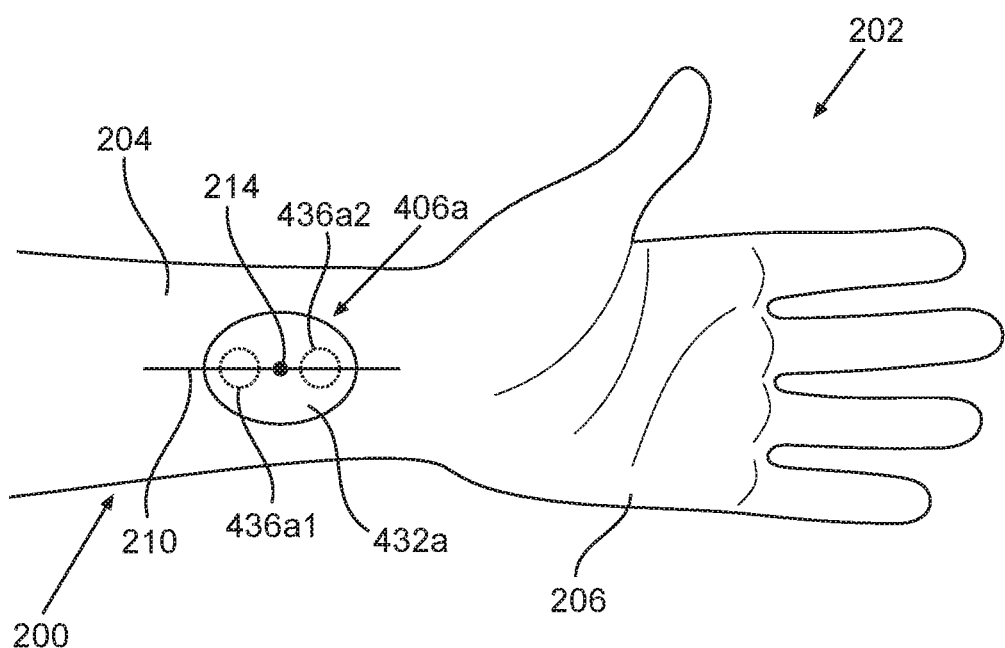
FIG. 5b schematically depicts a placement of the transcutaneous patch of FIG. 4b proximately to an acupoint on a left forearm in a parallel-electrode attachment configuration.

FIGS. 5*a* and 5*b* show two possible placements of first WP 406*a* on left forearm distal section 200. In FIG. 5*a* first WP 406*a* is shown attached onto forearm ventral side 204 in a transverse-electrode attachment configuration: First electrode 436*a*1 and second electrode 436*a*2 are positioned on opposite sides of median nerve 210, with left Pc6 acupoint 214 midway therebetween and with first electrode 436*a*1 located superiorly to second electrode 436*a*2. In FIG. 5*b* first WP 406*a* is shown attached onto forearm ventral side 204 in a parallel-electrode attachment configuration: First electrode 436*a*1 and second electrode 436*a*2 are positioned along median nerve 210, at equal distances proximally and distally relative to acupoint 214, respectively. Similarly, second WP 406*b* may be attached in a transverse-electrode attachment configuration onto right ankle inner side 270, such that third electrode 436*b*3 and fourth electrode 436*b*4 are positioned on opposite sides of ankle tibial nerve 260, with right Ki6 acupoint 274 midway therebetween. Second WP 406b may also be attached in a parallel-electrode attachment configuration onto right ankle inner side 270, such that third electrode 436b3 and fourth electrode 436b4 are positioned along ankle tibial nerve 260, with right Ki6 acupoint 274 midway therebetween.

Wireless transceivers 452a and 452b are configured to send information to, and receive information from, wireless communication unit 422, and thereby to establish communication between control module 420 and control circuitries 450a and 450b, respectively, and indirect communication between control circuitries 450a and 450b. According to some embodiments, wireless transceivers 454a and 454b may be configured to communicate directly therebetween, as well as with any other wireless transceiver on any other WP. In such embodiments, a bulk of the real-time data processing may be implemented by the control circuitries (e.g. control circuitries 450a and 450b) rather than by control module 420.

According to some embodiments, stimulation unit 452a is configured to allow for generating a voltage between electrodes 436a1 and 436a2. According to some embodiments, stimulation unit 452a is configured to allow for generating a current passing through electrodes 436a1 and 436a2 when forming therewith a closed circuit. Stimulation unit 452a allows inducing a current through a conduction path extending through a subject's body part between first electrode 436a1 and second electrode 436a2 when the electrodes are attached onto the body part. In FIG. 5a or 5b, for example, the placement positions of electrodes 436a1 and 436a2 is selected such as to have the conduction path pass through/near a segment of median nerve 210, proximately to left Pc6 acupoint 214, and thereby electrically stimulate median nerve 210.

Similarly, according to some embodiments, stimulation unit 452b is configured to allow for generating a voltage between electrodes 436b3 and 436b4. According to some embodiments, stimulation unit 452b is configured to allow for generating a current passing through electrodes 436b3 and 436b4 when forming therewith a closed circuit. Stimulation unit 452b allows inducing a current passing through a conduction path extending through a subject's body part between third electrode 436b3 and fourth electrode 436b4 when the electrodes are attached onto the body part. For example, the placement position of electrodes 436b3 and 436b4 may be selected such as to have the conduction path pass through/near a segment of right ankle tibial nerve 260, proximately to right Ki6 acupoint 274, and thereby electrically stimulate right ankle tibial nerve 260.

According to some embodiments, stimulation unit 452a is configured to controllably apply a first electrical stimulation signal, such as stimulation signal 300 between electrodes 436a1 and 436a2, when first WP 406a is attached onto the skin, particularly at a first acupoint (e.g. as in FIGS. 5a and 5b), and thereby deliver electrical neuro-stimulation at the first acupoint. According to some embodiments, stimulation unit 452b is configured to controllably apply a second stimulation signal, such as stimulation signal 300, between electrodes 436b3 and 436b4, when second WP 406b is attached onto the skin, particularly at a second acupoint (e.g. right Ki6 acupoint 274), and thereby deliver electrical neurostimulation at the second acupoint. According to some embodiments, the first stimulation signal and the second stimulation signal may be substantially similar, except for a possibly differing in amplitude and/or maximum intensity. According to some embodiments, the first stimulation signal and the second stimulation signal may have a same frequency and be in phase (i.e. such that an overlap between simultaneously occurring stimulation pulses does not vary in time), but may otherwise differ from one another in waveforms of respective stimulation pulses. For example, the first stimulation signal may comprise a series of sine waves, while the second stimulation signal may comprise a series of square waves. According to some embodiments, the second stimulation signal may be temporally shifted with respect to the first stimulation signal, essentially similarly to how second stimulation signal 300b is temporally shifted relative to first stimulation signal 300a in FIG. 3b. According to some embodiments, stimulation pulses in the first stimulation signal may differ in intensity and/or in waveform. Similarly, stimulation pulses in the first stimulation signal may differ in intensity and/or in waveform. For example, the first stimulation signal may comprise a repetition of two square wave pulses, such that a first of the square wave pulses has twice the intensity of the second of the square wave pulses.

According to some embodiments, each of stimulation units 452a and 452b is configured to allow for controllably varying the stimulation parameters of the stimulation signals. In particular, each of stimulation units 452a and 452b may be configured to allow for controllably generating and modifying stimulation signals, including continuous signals, intermittent signals, as well as signals comprising burst pulses. In particular, stimulation units 452a and 452b may allow for generating pairs of simultaneous stimulation signals, wherein the stimulation signals stimulating median nerve 210 and ankle tibial nerve 260, respectively, are simultaneous (e.g. having a same frequency, and being in phase). According to some embodiments, a stimulation signal generated by stimulation unit 452b may be delayed relative to a stimulation signal generated by stimulation unit 452a, but otherwise be substantially identical thereto (i.e. each stimulation signal may be obtained from the other by a phase-shift).

In addition, the stimulation signals generated by stimulation units 452a and 452b may also differ in waveform, amplitude, and particularly in maximum intensity. The electrical resistivity (i.e. specific electrical resistance) may vary from a region about one acupoint to a region about another acupoint, requiring the application of stimulation signals having a different voltage maximum intensity at each of the regions in order to achieve the same maximum intensity for both currents. Further, a motor threshold at the vicinity of one acupoint may differ from the motor threshold at the vicinity of another acupoint. For example, a motor threshold at the vicinity of left Pc6 acupoint 214 may differ from a motor threshold at the vicinity of right Ki6 acupoint 274, requiring that the stimulation signal applied at left Pc16 acupoint 214 have a different maximum intensity than that of the stimulation signal applied at Ki6 acupoint 274 in order to approach/achieve both of the motor thresholds. Such a selective application of the stimulation signals differs from the embodiment described in the Electrical neuro-stimulation system for improving HRV section hereinabove, wherein first patch 106a and second patch 106b are attached onto left forearm ventral side 204 and right ankle inner side 270, respectively: In such a placement configuration, electrodes 136a and 136b may close a conduction path extending from one onto the other across the subject's body, i.e. extending crosswise, and a same current passes through both the electrodes and near/through respective proximate acupoints.

Further, embodiments comprising more than a single WP pair may allow for sequential neuro-stimulation of acupoint pairs. For example, applying a sequence of two pairs of stimulation pulses may include: (i) Simultaneously or at least partially simultaneously applying a first and a second current through a first and conduction path and a second conduction path comprising first electrode pair 436a and second electrode pair 436b, respectively. The first current and the second current each pass through/near a respective acupoint from a first acupoint pair. (ii) Subsequently, simultaneously or at least partially simultaneously applying a third current and a fourth current through a third conduction path and a fourth conduction path comprising a third electrode pair 436c in third WP 406c and a fourth electrode pair 436d in fourth WP 406d, respectively. The third current and the fourth current each pass through/near a respective acupoint from a second acupoint pair. As used herein, "sequence of pairs of stimulation pulses" and "paired-pulses stimulation sequence" may refer to a group of pairs of stimulation pulses applied one pair after the other at different acupoint pairs, e.g. by different electrode pairs, such that each pair of stimulation pulses is applied simultaneously or at least partially simultaneously. "Sequence of pairs of stimulation pulses", "sequence of paired stimulation pulses", or "paired-pulses stimulation sequence" may also refer to a number of groups of pairs of stimulation pulses (e.g. two, three, four, five, or even ten groups), such that all pairs of stimulation pulses within a group are applied simultaneously or at least partially simultaneously, but pairs of stimulation pulses from different groups (e.g. a pair of stimulation pulses from a first group and a pair of stimulation pulses from a second group) are applied one after the other, as elaborated on hereinebelow. Such sequences of paired stimulation pulses may allow for sequentially delivering electrical neuro-stimulation at different target acupoint pairs, as elaborated on hereinbelow and in the Heart-rate variability improvement method section.

According to some embodiments, system 400 is configured to successively apply n≥3 pairs of stimulation pulses, one pair after another, i.e. apply a sequence of n pairs of stimulation pulses: a first stimulation pulse in a pair of stimulation pulses being applied between electrodes on a first WP in a respective pair of WPs, and the second stimulation pulse in the pair of stimulation pulses being applied between electrodes on the second WP in the respective pair of WPs. According to some embodiments, system 400 is configured to repeatedly apply the sequence of n pairs of stimulation pulses, such that the first pulse pair in each sequence may be delayed, for example, by 1 sec relative to a last pulse pair in a preceding sequence thereto. According to some embodiments, control module 420, and the control circuitries and neuro-stimulation units in each WP (such as control circuitries 450a and 450b and neuro-stimulation units 452a and 452b on first WP 406a and second WP 406b, respectively) are configured to generate n pairs of stimulation signals, such as pairs of stimulation signal 300, and such that: (i) For any m (1≤m≤n) a first stimulation signal and a second stimulation signal in the mth stimulation signal pair are applied between electrodes on a first WP and a second WP in the mth WP pair, respectively. (ii) For any m (1≤m≤n) the first stimulation signal and the second stimulation signal in the mth stimulation signal pair are in phase (i.e. onsets of respective stimulation pulses in each of the stimulation signals are simultaneous) and may further be substantially identical up to a possible difference in respective maximum intensities. (iii) For any m (2≤m≤n) stimulation pulses of the mth stimulation signal pair are delayed by 1 μsec to 1 sec or 10 μsec to 100 msec relative to a respective stimulation pulses of the (m−1)th stimulation signal pair.

According to some embodiments, a sequence of pairs of stimulation pulses may comprise simultaneously or at least partially simultaneously applying more than one pair of stimulation pulses. For example, a first pair of stimulation pulses may be applied by a first WP and a second WP, respectively, of a first WP pair. Subsequently, a second pair of stimulation pulses may be applied by a third WP and a fourth WP, respectively, of a second WP pair, and simultaneously or at least partially simultaneously to the second pair of stimulation pulses, a third pair of stimulation pulses may be applied by a fifth WP and a sixth WP of a third WP pair. The sequence may then be repeated.

Control module 420, the control circuitries and the stimulation units on the WPs may be further configured to repeatedly generate a stimulation cycle of paired-pulse stimulation sequences, the stimulation cycle comprising a rapid succession of potentially different sequences of paired stimulation pulses. The sequences may differ, for example, in amplitudes and waveforms of the paired pulses, as well as in an order that the paired pulses are applied. Different sequences of pairs of stimulation pulses in a stimulation cycle may also differ in pairings of WPs. For example, a first stimulation sequence may comprise two paired pulses applied by a first WP pair and by a second WP pair, respectively, while a second stimulation sequence may comprise two paired pulses subsequently applied by a third WP pair and a fourth WP pair, respectively. The time delay between a last pair of pulses in a last sequence in a cycle and a first pair of pulses in a first sequence in a successive cycle may be significantly greater than a time delay between successive sequences in a cycle, for example, 1 sec as compared to 1 msec.

It is noted that different WP pairs need not necessarily be fully distinct, in the sense that two different WP pairs may include a same WP. For example, a first WP pair may comprise first WP 406a and second WP 406b, and a second WP pair may comprise first WP 406a and third WP 406c. The WP pairs may be used alternately. Applying a sequence of two paired stimulation pulses may include delivering neuro-stimulation by first WP 406a while simultaneously or at least partially simultaneously delivering neuro-stimulation by second WP 406b, and subsequently delivering neuro-stimulation by first WP 406a while simultaneously or at least partially simultaneously delivering neuro-stimulation by third WP 406c. The first of the two paired stimulation pulses may then be applied again by first WP 406a and second WP 406b, respectively, followed by the second of the two paired stimulation pulses being applied again by first WP 406a and third WP 406c, and so on.

Control module 420 communicates with control circuitries 450a and 450b through wireless communication unit 422 and wireless transceivers 454a and 454b, respectively. Control circuitries 450a and 450b are configured to convey to stimulation units 452a and 452b, respectively, instructions from control module 420, e.g. instructions to start or stop applying one or more stimulation signals between one or more of the electrodes pairs, e.g. electrode pairs 436a and 436b, or instructions detailing adjustments to the stimulation signals. According to some embodiments, memory circuitry 428 may store stimulation algorithms corresponding to respective stimulation session goals. According to some embodiments, control module 420 may comprise loop feedback circuitry (not shown) and the stimulation algorithms may further comprise instructions for the real-time adjustment of the stimulation signals, based on data received by control module 420 from WP sensors 458a and 458b via control circuitries 450a and 450b and/or any other sensors on any other WPs via respective control circuitries, and/or from external monitoring devices, such as an ECG monitor.

According to some embodiments, the control circuitries on the WPs may each comprise loop feedback circuitry (not shown), and may be configured to instruct a respective stimulation unit (i.e. on the same WP as the control circuitry) to adjust stimulation parameters based on real-time data from the respective sensor.

According to some embodiments, session data is saved and stored in memory circuitry 428. Similarly, to processing circuitry 126, processing circuitry 426 may further be installed with machine learning algorithms for analyzing stored session data to adapt the stimulation algorithms to better meet the (objectives of) respective stimulation session goals in future treatments (i.e. stimulation sessions).

According to some embodiments, the data received from the sensors is communicated to an online database (via an internet connection port (not shown) in controller 402 or via wireless communication unit 422) where it is stored and analyzed on an associated database computer, as detailed in the Learning methods for heart-rate variability improvement section hereinbelow. According to some embodiments, the real-time data processing is performed on the database computer and adjusted values of the stimulation parameters are communicated back to controller 402.

According to some embodiments, WP sensors 458a and 458b are muscle contraction sensors. WP sensors 458a and 458b are each configured to send a signal to control circuitries 450a and 450b, respectively, when a motor threshold is approached/has been reached in a region near where first WP 406a and second WP 406b are placed, respectively. As a safety precaution, control circuitries 450a and 450b may be configured to stop, attenuate, or not further increase the maximum intensity of, the stimulation signal applied by first WP 406a and second WP 406b on receipt of any of the above-mentioned signals.

According to some embodiments, control module 420 may receive real-time data indicative of temporal heart activity of the subject (e.g. from an external ECG monitor (not shown) via conduction cables (not shown) connecting controller 402 to the ECG monitor), thereby allowing for synchronizing an onset of each stimulation pulse with a time of occurrence of a respective reference point, as elaborated on in the description of system 100. In particular, according to some embodiments, control module 420 and/or the control circuitries may be configured to time the onsets of a pair of stimulation pulses such as to occur after the occurrence time of a respective reference point. According to some embodiments, control module 120 may be configured to time the onsets of stimulation pulses in a sequence of pairs of stimulation pulses such as to occur after respective occurrence times of respective reference points. According to some embodiments, control module 420 and/or the control circuitries may be configured to time the application of one or more pairs of intermittent stimulation signals such as to be alternating with the reference points. According to some embodiments, the reference points may be ECG signal R peaks of respective normal heart beats (i.e. non-arrhythmic heart beats). An onset of a pair of stimulation pulses may be configured to be delayed relative to a respective R peak occurrence time.

According to some embodiments, a sequence of paired pulses may be timed such as to fully occur in a 400 msec time interval beginning 100 msec after a respective R peak occurrence time. According to some embodiments, a cycle of sequences of paired pulses may be timed such as to fully occur in a 400 msec time interval beginning 100 msec after a respective R peak occurrence time. According to some embodiments, each pair of pulses in a sequence of paired pulses is timed such as to fully occur in a 400 msec time interval beginning 100 msec after a respective R peak occurrence time. That is to say, a first pulse pair, applied between a first electrode pair on a first WP and a second electrode pair on a second WP, respectively, is timed such as to fully occur in a 400 msec time interval beginning 100 msec after a first R peak occurrence time, while a second pulse, applied between a third electrode pair on a third WP and a fourth electrode pair on a fourth WP, respectively, is timed such as to fully occur in a 400 msec time interval beginning 100 msec after a second R peak occurrence time, and so on.

Figure 6A:
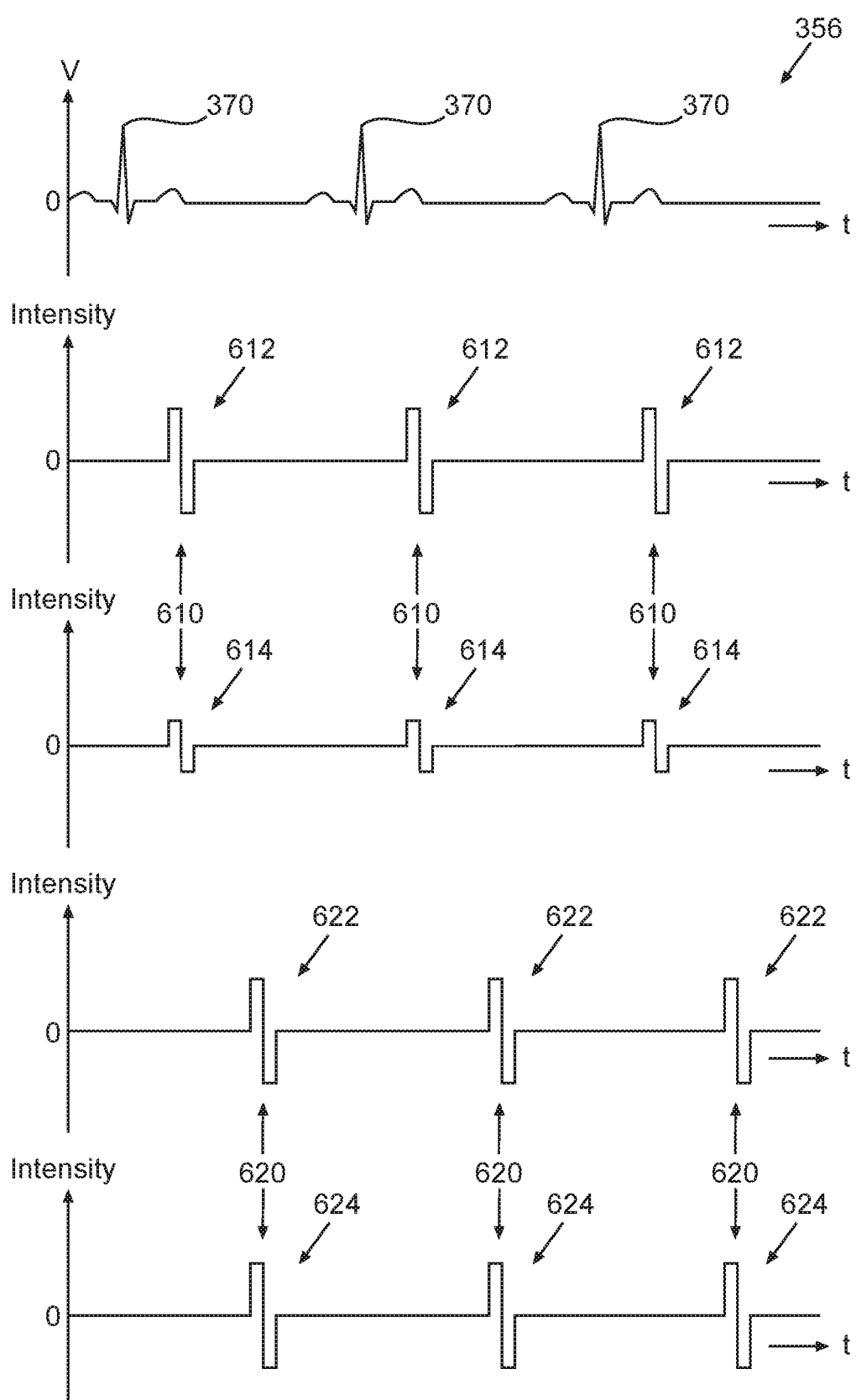
FIG. 6a schematically depicts repeated application of a sequence of pairs of stimulation pulses synchronized with an ECG signal.

FIG. 6a depicts a repeated application of a stimulation sequence 600 of two paired pulses synchronized with an ECG signal 356. A first pair of pulses 610 comprises a first pulse 612 and a second pulse 614. First pulse 612 is applied between electrodes 436a1 and 436a2 on first WP 406a. Second pulse 614 is applied between electrodes 436b3 and 436b4 on second WP 406b. First pulse 612 and second pulse 614 are applied substantially simultaneously. A second pair of pulses 620 comprises a third pulse 622 and a fourth pulse 624. Third pulse 614 is applied between electrodes on third WP 406c. Fourth pulse 624 is applied between electrodes on fourth WP 406b. Third pulse 622 and second pulse 624 are applied substantially simultaneously and subsequently to first pulse 612 and second pulse 614. Stimulation pulses 612, 614, 622, and 624 are similar to stimulation pulse 300, but may differ in amplitude and/or width. Each stimulation sequence is timed to commence between 100-500 msec or between 200-400 msec after a respective R peak 370 (of a normal beat) occurrence time.

Figure 6B:
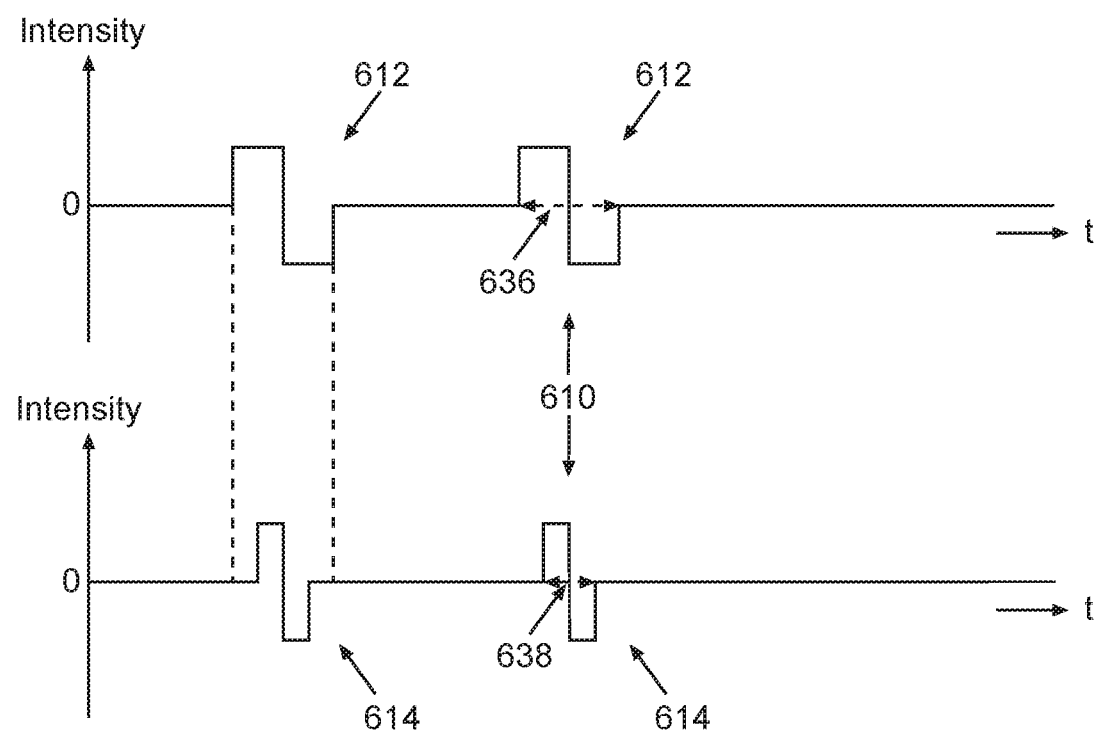
FIG. 6b schematically depicts repeated application of a sequence of pairs partially overlapping of stimulation pulses.

FIG. 6b depicts a repeated application of first pair of pulses 610 in an embodiment wherein first pulse 612 and second pulse 614 are applied partially simultaneously. A pulse width 636 of first pulse 612 is greater than a pulse width 638 of second pulse 614. First pulse 612 begins before second pulse 614 begins and ends after second pulse 614 ends.

Figure 6C:
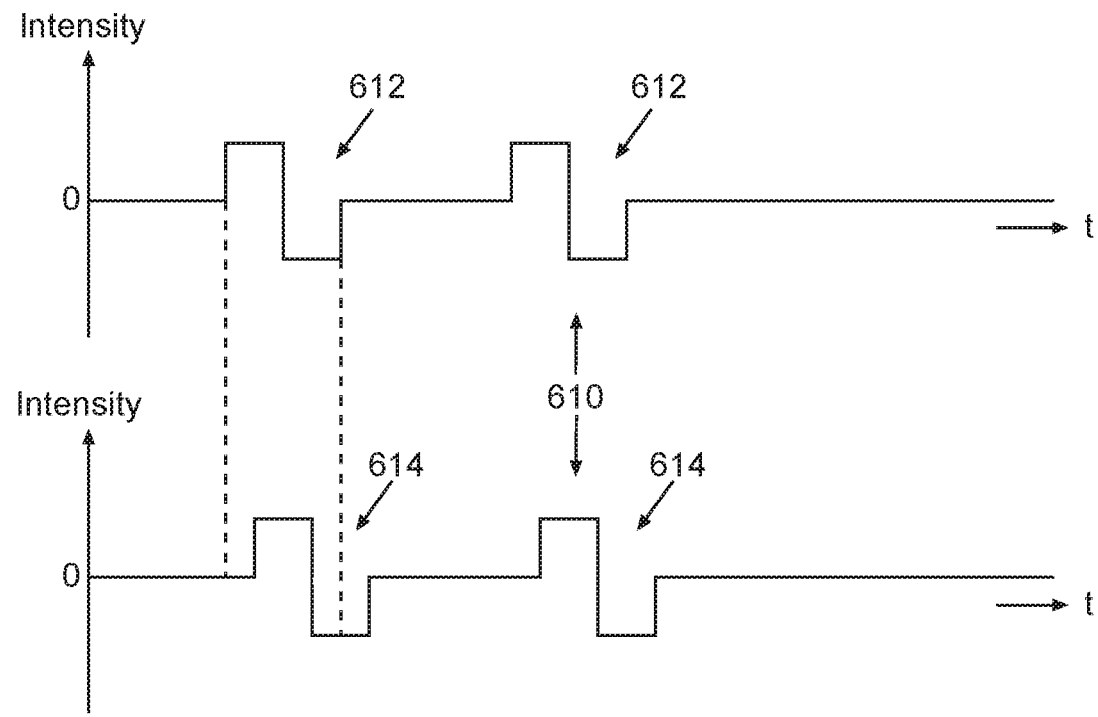
FIG. 6c schematically depicts repeated application of a sequence of pairs of partially overlapping stimulation pulses.

FIG. 6c depicts a repeated application of first pair of pulses 610 in another embodiment wherein first pulse 612 and second pulse 614 are applied partially simultaneously. First pulse 612 begins before second pulse 614 begins. First pulse 612 ends after second pulse 614 begins but before second pulse 614 ends.

It is to be understood that the above-mentioned stimulation pulses, signals, sequences, cycles, and algorithms are discussed solely by way of examples of effective treatments for modulating HRV discovered by the inventor. Other electrode arrangements and stimulation parameters, etc., which may be useful for modulating HRV are considered to be within the scope of the present invention.

Wireless system 400 may be operated (i.e. controlled) by a trained professional via user control interface 424, essentially similarly to how system 100 may be operated using user control interface 124, as described hereinabove.

It is noted that any type of neuro-stimulation delivered by wireless system 400 may be delivered by system 100. For example, the transverse-electrode attachment configuration of FIG. 5a may be reproduced by first patch 106a and second patch 106b by attaching the patches onto forearm ventral side 204 such that first electrode 106a and second 106b are positioned at the FIG. 5a locations of first electrode 436a1 and second electrode 436a2, respectively. In particular, if first electrode 136a and second electrode 136b are substantially identical to first electrode 436a1 and second electrode 436a2, respectively, than for a given stimulation signal (induced by neuro-stimulation unit 122 and stimulation unit 452a, respectively), the respective conduction paths formed by electrodes 136a and 136b and electrodes 436a1 and 436a2 are substantially identical.

Methods for Improving Heart-Rate Variability

Another aspect of the invention finds an embodiment in a method 700 for increasing a subject's HRV by delivering electrical neuro-stimulation. Method 700 comprises the following steps:

- Optionally, a step 702 of obtaining (if not already available), or updating, personal data, such as age, gender, and medical history.
- Optionally, a step 704 of measuring one or more physiological parameters of the subject, e.g. HRV.
- A step 706 of selecting a stimulation session goal.
- A step 708 of selecting or determining a stimulation algorithm, the stimulation algorithm comprising instructions for the delivering of neuro-stimulation at at least one core acupoint pair, as explained hereinbelow. The stimulation algorithm may depend on the stimulation session goal. Optionally the stimulation algorithm may be determined taking into account data from any one of steps 702 and 704.
- A step 710 of delivering electrical neuro-stimulation at one or more acupoint pairs and possibly also unpaired acupoints, as specified by the stimulation algorithm.
- Optionally, a step 720 of monitoring one or more physiological parameters of the subject during the electrical neuro-stimulation, and accordingly adjusting the stimulation signals.
- Optionally, a step 730 of measuring one or more physiological parameters of the subject once the application of the electrical neuro-stimulation is over, and dependent on the measured values of the physiological parameters, repeating steps 708, 710, 720, and 730.

Step 710 comprises electrically stimulating pairs of peripheral nerves by applying electrical stimulation signals at respective acupoint pairs—each acupoint in an acupoint pair being located proximately to a respective peripheral nerve. At least one of the acupoint pairs includes one acupoint associated with cardiovascular function (i.e. such that delivering neuro-stimulation only at the acupoint may affect cardiovascular function), and one acupoint not associated with cardiovascular function (i.e. such that delivering neuro-stimulation only at the acupoint does not, and/or is not known to, affect cardiovascular function). "Core acupoint pair" refers to an acupoint pair comprising one acupoint associated with cardiovascular function and one acupoint not associated with cardiovascular function.

Unexpectedly, the inventor of the present invention has found that delivering neuro-stimulation simultaneously at both acupoints in a bilateral and/or a semi-central core acupoint pair may have a synergistic effect in improving HRV (i.e. increasing HRV) as compared to a reference HRV. As used herein, the term "synergistic effect in improving HRV" refers to an increase in HRV, resulting from delivering neuro-stimulation at both of the acupoints simultaneously or at least partially simultaneously, that is substantially greater than an increase in HRV resulting from delivering same neuro-stimulation at the same acupoints successively, i.e. at one acupoint at a time. An increase (i.e. improvement) in HRV may be quantified by an increase in HRV parameters, such as the SDNN (standard deviation of NN intervals), rMSSD (root mean square of successive differences), and pNN50 (the number of pairs of successive NN intervals, which differ by more than 50 msec, divided by the total number of NN intervals). According to exemplary embodiments, the synergistic effect is measured relative to the HRV obtained by delivering the same neuro-stimulation only at the acupoint associated with cardiovascular function. According to certain embodiments, "substantially greater" refers to a higher value at observed $p<0.05$. Neuro-stimulation at a single acupoint may be delivered, for example, by attaching a dual-electrode patch, e.g. first WP 406a, proximately to the acupoint and applying a stimulation pulse between electrodes embedded in/on the patch, e.g. first electrode 436a1 and second electrode 436a2. Alternatively, neuro-stimulation at a single acupoint may be delivered, for example, by attaching a first patch and a second patch, e.g. first patch 106a and second patch 106b, near the acupoint. A current is then induced through a conduction path comprising electrodes in/on the first and second patch, respectively, e.g. first electrode 136a and second electrode 136b, and passing near/through the acupoint.

Furthermore, the present invention now discloses that simultaneously, partially simultaneously, or sequentially delivering neuro-stimulation at more than one core acupoint pair may result in further strengthening the synergistic effect. The increase in HRV resulting from delivering neuro-stimulation at at least two core acupoint pairs may be substantially greater than the sum of respective increases in HRV resulting from delivering neuro-stimulation at each of the core acupoint pairs alone.

Furthermore, the present invention discloses that simultaneously, partially simultaneously, or sequentially delivering neuro-stimulation at two or more acupoint pairs, wherein at least one of the acupoints is not associated with cardiovascular function, may result in further strengthening the synergistic effect due to the at least one core acupoint pair.

As used herein, "neuro-stimulation delivered at an acupoint pair" refers to neuro-stimulation delivered simultaneously or at least partially simultaneously at both acupoints in the acupoint pair, unless the context clearly dictates otherwise.

According to some embodiments, neuro-stimulation delivered at a first bilateral pair may be accompanied by neuro-stimulation delivered at a second bilateral pair, reciprocal thereto. In particular, neuro-stimulation delivered at a first core acupoint pair, which is bilateral, may be accompanied by neuro-stimulation delivered at a second core acupoint pair, reciprocal thereto. According to some embodiments, the neuro-stimulation at two acupoint pairs, which are reciprocal, may be delivered simultaneously, partially simultaneously, or alternately. The increase in HRV resulting from delivering neuro-stimulation at two core acupoint pairs, which are reciprocal, may be substantially greater than the sum of respective increases in HRV resulting from delivering neuro-stimulation at each of the core acupoint pairs alone. As described in the Treatment results using an embodiment of system 100 section hereinbelow, deliverance of neuro-stimulation simultaneously at four core acupoint pairs, such that a first and a second of the four core acupoint pairs are reciprocal, and such that a third and a fourth of the four core acupoint pairs are reciprocal, resulted in an HRV increase of more than 40%, as quantified by the SDNN.

The following acupoints are known in the art to be associated with cardiovascular function:

1. The left and right Ht7 acupoints in the left and right wrists, near the left and right ulnar nerves, respectively.

2. The left and right Pc6 acupoints in the left and right ventral forearms, near the left and right median nerves, respectively.
3. The left and right Gb34 acupoints in the left and right legs, near the left and right peroneal nerves, respectively.
4. The left and right Ub14 acupoints in the back on the left and right side of the spine, near left and right thoracic vertebral nerves, respectively.
5. The left and right Ub15 acupoints on the left and right side of the spine, near left and right thoracic vertebral nerves, respectively.
6. The left and right HUA T4 acupoints in the back on the left and right side of the spine, near left and right thoracic vertebral nerves, respectively.
7. The left and right HUA T5 acupoint in the back on the left and right side of the spine, near left and right thoracic vertebral nerves, respectively.
8. The Cv17 acupoint in the chest, near the chest midline cutaneous nerve.

The following acupoints are not known in the art to be associated with cardiovascular function:
9. The left and right Sp6 acupoints in the left and right legs, near the left right posterior tibial nerves, respectively.
10. The left and right Ki6 acupoints in the left and right ankles, near the left and right ankle tibial nerves, respectively.
11. The St36 acupoints under in the left and right legs under the left and right knees, near the left and right peroneal nerves, respectively.
12. The left and right Lv14 acupoints in the chest, near the left and right lateral-cutaneous intercostal nerves, respectively.
13. The Cv12 acupoint in the chest, above the abdominal vagus nerve.
14. The left and right St32 acupoints in the thighs, near the left and right femoral nerves, respectively.
15. The left and right Lv3 acupoints in the feet, near the left and right distal peroneal nerves, respectively.
16. The left and right Li4 acupoints in the hands, near the left and right superficial radial nerves, respectively.

Unexpectedly, the inventor has found that simultaneously neuro-stimulating any of the following acupoint pairings may lead to a synergistic effect in HRV improvement:
1. Bilateral pairing of an Ht7 acupoint with an Sp6 acupoint.
2. Bilateral pairing of a Pc6 acupoint with a Ki6 acupoint.
3. Bilateral pairing of a Pc6 acupoint with an Lv14 acupoint.
4. Bilateral pairing of a Pc6 acupoint with an Lv3 acupoint.
5. Pairing of the Cv17 acupoint with any of the two Lv14 acupoints.

The synergistic effect may be enhanced (i.e. strengthened) by neuro-stimulating at other acupoint pairs, e.g. simultaneously, partially simultaneously, or sequentially, as described hereinbelow.

Step 710 may further comprise delivering neuro-stimulation at a core acupoint pair and at an unpaired acupoint, such that the neuro-stimulation delivered at the unpaired acupoint is delivered at least partially simultaneously with the neuro-stimulation delivered at the core acupoint pair.

The neuro-stimulation may comprise delivering continuous stimulation signals, and/or intermittent stimulation signals, and/or stimulation signals comprising burst pulses, and/or any combination thereof, at one or more acupoint pairs, wherein at least one of the acupoint pairs is a core acupoint pair. According to some embodiments, the stimulation signal may comprise a series of stimulation pulses. According to some embodiments, the stimulation pulses may differ in maximum intensity and/or in waveform.

According to some embodiments, the neuro-stimulation delivered at an acupoint pair, particularly, a core acupoint pair, may comprise inducing a current through a conduction path in the subject's body passing near/through both acupoints in the pair: For example, by attaching a first patch and a second patch, such as first patch 106a and second patch 106b, onto the subject's skin proximately to the two acupoints in the pair, respectively, and applying an electrical stimulation signal between an electrode embedded in/on the first patch and an electrode embedded in/on the second patch, e.g. first electrode 136a and second electrode 136b, respectively. Or, for example, by attaching two percutaneous patches, such as percutaneous patch 190, onto the subject's skin proximately to the two acupoints in the pair, respectively, and applying an electrical stimulation signal between the electrodes in/on the two patches. "Crosswise neuro-stimulation" refers to neuro-stimulation of this type.

According to some embodiments, the neuro-stimulation delivered at an acupoint pair, particularly, a core acupoint pair, may comprise inducing a first current through a first conduction path in the body passing near/through a first acupoint in the pair, and inducing a second current through a second conduction path in the body passing near/through the second acupoint in the pair: For example, by attaching a pair of patches, such as first WP 406a and second WP 406b, onto the subject's skin proximately to the two acupoints in the pair, respectively, and applying a first electrical stimulation signal between a pair of electrodes in/on the first patch, e.g. first electrode pair 436a, and applying a second electrical stimulation signal between a pair of electrodes in/on the second patch, e.g. second electrode pair 436b. "Local neuro-stimulation" refers to neuro-stimulation of this type. According to some embodiments, the stimulation signals applied between the electrodes in/on the first patch and the electrodes in/on the second patch, respectively, may be substantially identical or may differ, e.g. in amplitude, maximum intensity, and/or waveform. According to some embodiments, the stimulation signals between the electrodes in/on the first patch and the electrodes in/on the second patch, respectively, may be applied simultaneously, or at least partially simultaneously.

According to some embodiments, both crosswise and local neuro-stimulation may be delivered. For example, crosswise neuro-stimulation may be delivered at a core acupoint pair, while local neuro-stimulation at another acupoint (i.e. an acupoint not in the core acupoint pair).

The neuro-stimulation may comprise applying different stimulation signals at different acupoint pairs, respectively, such that at least one of the acupoint pairs is a core acupoint pair, and with each stimulation signal comprising a series of respective stimulation pulses. According to some embodiments, the different stimulation signals may have a same frequency, but may differ both in amplitude and/or waveform. According to some embodiments, the neuro-stimulation may comprise sequentially neuro-stimulating acupoint pairs. According to some embodiments, in crosswise neuro-stimulation, a sequential neuro-stimulation may comprise repeatedly applying a sequence of stimulation pulses, each stimulation pulse being applied at a different acupoint pair. According to some embodiments, the stimulation pulses may be applied one pulse at a time. According to some embodiments, in local neuro-stimulation, a sequential neuro-stimulation may comprise repeatedly applying a sequence of pairs of stimulation pulses, each pair of stimulation pulses being applied at a different acupoint pair, such that a first pulse in a pair is applied at a first acupoint of a respective acupoint pair and the second pulse in the pair is simultaneously or at least partially simultaneously applied at the second acupoint of the respective acupoint pair. According to some embodiments, the stimulation pairs of stimulation pulses may be applied one pair at a time.

According to some embodiments, a first stimulation signal, such as stimulation signal 300a, is applied at acupoints in a first pair. A second stimulation signal, such as stimulation signal 300b, is applied at acupoints in a second pair. An onset of each stimulation pulse in the second stimulation signal may be delayed by 1 μsec to 1 sec or 10 μsec to 100 msec relative to an onset of a respective stimulation pulse of the first stimulation signal, as depicted in FIG. 3b. At least one of the first pair and the second pair is a core acupoint pair. According to some embodiments, stimulation signals in a first pair of stimulation signals, similar to stimulation signal 300a, are substantially simultaneously applied at respective acupoints in a first acupoint pair. Stimulation signals in a second pair of stimulation signals, similar to stimulation signal 300b, are substantially simultaneously applied at respective acupoints in a second acupoint pair. Onsets of each pair of stimulation pulses in the second pair of stimulation signals may be delayed by 1 μsec to 1 sec or 10 μsec to 100 msec relative to onsets of a respective pair of stimulation pulses in the first pair of stimulation signals. At least one of the first pair and the second pair is a core acupoint pair.

According to some embodiments, n≥3 stimulation signals are sequentially applied at n acupoint pairs, respectively, wherein at least one of the n acupoint pairs is a core acupoint pair. Each of the stimulation signals is similar to stimulation signal 300 but different stimulation signals are temporally shifted relative to one another. For all m (2≤m≤n) an onset of each stimulation pulse of the mth stimulation signal may be delayed by 1 μsec to 1 sec or 10 μsec to 100 msec relative the onset of a respective stimulation pulse of the (m−1)th stimulation signal. According to some embodiments, n≥3 pairs of stimulation signals, are sequentially applied at n acupoint pairs, respectively, wherein at least one of the n acupoint pairs is a core acupoint pair. Each of the stimulation signals is similar to stimulation signal 300, with stimulation signals within a stimulation signal pair being applied substantially simultaneously, but with different stimulation signal pairs being temporally shifted relative to one another. For all m (2≤m≤n) an onset of each pair of stimulation pulses of the mth pair of stimulation signals may be delayed by 1 μsec to 1 sec or 10 μsec to 100 msec relative the onset of a respective pair of stimulation pulse of the (m−1)th pair of stimulation signals. According to some embodiments, the number of acupoint pairs n may equal 4, 5, 6, or even 10, or more. According to some embodiments, the different acupoint pairs are not fully distinct in the sense that some acupoint pairs share a common acupoint. For example, the first acupoint pair may comprise the left Pc6 acupoint and the right Lv3 acupoint, while the second pair may comprise the right Pc6 acupoint and the left Lv3 acupoint.

According to some embodiments, in crosswise neuro-stimulation, a sequence of stimulation pulses may comprise applying some of the stimulation pulses simultaneously or at least partially simultaneously. For example, a first stimulation pulse may be applied at a first acupoint pair, and subsequently a second and third stimulation pulses may be simultaneously or at least partially simultaneously applied at a second and third acupoint pairs, respectively. The sequence may then be repeated. Or, for example, a first pair of stimulation pulses may be substantially simultaneously applied a first and second acupoint pairs, respectively, and subsequently a second pair of stimulation pulses may be substantially simultaneously applied at the first acupoint pair and a third acupoint pair, respectively.

According to some embodiments, in local neuro-stimulation, a sequence of pairs of stimulation pulses may comprise simultaneously or at least partially simultaneously applying more than one pair of stimulation pulses. For example, a first pair of stimulation pulses may be applied at a first acupoint pair, respectively, and subsequently a second pair of stimulation pulses and a third pair of stimulation pulses may be substantially simultaneously applied at a second acupoint pair and at a third acupoint pair, respectively. The sequence may then be repeated. Or, for example, a first pair of stimulation pulses and a second pair of stimulation pulses may be substantially simultaneously applied at a first acupoint pair and a second acupoint pair, respectively. Subsequently, a third pair of stimulation pulses and a fourth pair of stimulation pulses may be substantially simultaneously applied at the first acupoint pair and a third acupoint pair, respectively. The sequence may then be repeated.

According to some embodiments, in local neuro-stimulation, the rate of delivery of stimulation pulses at a first acupoint and the rate of delivery of stimulation pulses at a second acupoint may be multiples of one another, e.g. twice as many or three times as many stimulation pulses may be delivered per minute at the first acupoint as compared to the second acupoint. Similarly, in crosswise neuro-stimulation, the rate of delivery of stimulation pulses at a first acupoint pair and the rate of delivery of stimulation pulses at a second acupoint pair may be multiples of one another.

According to some embodiments, a stimulation cycle may be repeatedly applied, the stimulation cycle comprising applying a succession of potentially different stimulation sequences. The sequences may differ, for example, in amplitudes and waveforms of the stimulation pulses, as well as in an order that the stimulation pulses are applied at respective acupoint pairs. Different stimulation sequences in a stimulation cycle may also be applied at different sets of stimulation acupoint pairs. For example, a first stimulation sequence comprising two pulses may be applied at a first acupoint pair and at a second acupoint pair, respectively, while a second stimulation sequence comprising two pulses may be applied at a third acupoint pair and at a fourth acupoint pair, respectively. The time delay between a last pulse in a last sequence in a cycle and a first pulse in a first sequence in a successive cycle may be significantly greater than a time delay between successive sequences in a cycle, for example, 1 sec as compared to 1 msec.

According to some embodiments, a stimulation cycle of paired-pulse stimulation sequences may be repeatedly applied, the stimulation cycle comprising application of a succession of potentially different stimulation sequences of paired pulses. The sequences may differ, for example, in amplitudes and waveforms of the paired pulses, as well as in an order that the paired pulses are applied at respective acupoint pairs. Different stimulation sequences of paired pulses in a stimulation cycle may also differ in pairings of acupoints. For example, a first stimulation sequence comprising two paired pulses may be applied at a first acupoint pair and a second acupoint pair, respectively, while a second stimulation sequence comprising two paired pulses may be applied at a third acupoint pair and a fourth acupoint pair, respectively. The time delay between a last pair of pulses in a last sequence in a cycle and a first pair of pulses in a first sequence in a successive cycle may be significantly greater than a time delay between successive sequences in a cycle, for example, 1 sec as compared to 1 msec.

The following stimulation (treatment) algorithms have been found by the inventor to be effective in improving (i.e. increasing) HRV:

I. Sequential crosswise/local neuro-stimulation in the following order:
   a. A left Pc6-right Lv3 core acupoint pair.
   b. An acupoint pair reciprocal thereto (a right Pc6-left Lv3 core acupoint pair).
   while substantially simultaneously delivering neuro-stimulation at a left St36-right St36 acupoint pair (St36 acupoint pair), such that each pulse or pair of pulses delivered at each of the core acupoint pairs is substantially simultaneous to a respective pulse delivered at the St36 acupoint pair (and such that each of the pulses delivered at the St36 acupoint pair is substantially simultaneous to a pulse delivered or pair of pulses delivered at the core acupoint pairs). For example, the rate of delivery of stimulation pulses at the St36 acupoint pair may be four times higher than a rate of delivery of the stimulation signals at each of the core acupoint pairs. According to some embodiments, the neuro-stimulation may be delivered sequentially at all three acupoint pairs.

II. Sequential crosswise/local neuro-stimulation in the following order:
   a. A left Ht7-right Sp6 core acupoint pair.
   b. A right Ht7-left Sp6 core acupoint pair.
   c. The left Pc6-right Lv3 core acupoint pair.
   d. The right Pc6-left Lv3 core acupoint pair.
   e. A left St36-right St36 acupoint.

In both stimulation algorithm I and stimulation algorithm II each stimulation signal may be similar to any one of the different embodiments of stimulation signal 300 listed in the description of stimulation signal 300 hereinabove in the Electrical neuro-stimulation system for improving HRV section. Other stimulation algorithms potentially effective for improving HRV are listed in the description of method 900, hereinbelow.

According to some embodiments, method 700 may further comprise step 702 wherein the subject provides personal data, including age, gender, medical history, and heart related symptoms, and possibly information regarding physical activity, smoking habits, diet, and/or the like. The personal data may be stored in a memory for future reference and/or transmitted to an online database, as described hereinbelow.

According to some embodiments, method 700 may further comprise prior to step 710, step 704 wherein one or more physiological parameters of the subject are measured. The physiological parameters may include, for example, heart-rate (from which HRV parameters may be computed), degrees of muscle contraction at respective acupoints, and/or blood pressure. The physiological parameters may be stored in a memory for future reference and/or transmitted to an online database, as described hereinbelow.

Method 700 may further comprise, prior to step 710, step 706 of selecting a stimulation session goal. Stimulation session goals may include increasing HRV before a physical workout to improve efficacy thereof, improving quality of sleep, long-term HRV improvement, as well as improving HRV to treat heart-related conditions (e.g. various arrhythmias, as elaborated on in the description of method 900 hereinbelow). The stimulation session goal may also be determined taking into account data from any steps of 702 and 704. For example, a subject's medical history, heart-related symptoms, and measured values of physiological parameters may affect the stimulation session goal.

Method 700 may further comprise, prior to step 710, step 708 of determining the stimulation algorithm (specifying the acupoints and the acupoint pairs, the application order of stimulation signals, and respective stimulation parameters characterizing each of the stimulation signals, etc.). According to some embodiments, the stimulation algorithm may be automatically determined based on the stimulation session goal. According to some embodiments, the stimulation algorithm may be determined taking into account also the subject's personal data, and/or the measured values of the one or more physiological parameters obtained in step 704. If the subject has already undergone one or more neuro-stimulation sessions, the stimulation algorithm may be determined taking into account also session data from previous neuro-stimulation sessions (e.g. values of the physiological parameters measured before, during, and/or after the sessions, the stimulation algorithm employed, and specification of any adjustments made to the stimulation parameters during the sessions, and so on). The determination may be performed by a trained professional, i.e. a person administering the neuro-stimulation, or automatically by a system used to deliver the neuro-stimulation, such as system 100 or system 400, or by a remote agent, e.g. a database computer, communicatively associated with the system delivering the neuro-stimulation, as described hereinbelow. The trained professional may also decide to modify the system's automatic determination.

Further, step 708 may comprise determining the maximum intensity of each of the stimulation signals manually or automatically. Manually, the maximum intensities may be determined based on tactile sensation of the subject. For local neuro-stimulation, the determination of the maximum intensities may proceed by applying a stimulation signal at one acupoint at a time. At the beginning of a stimulation session, when a first stimulation signal is first applied at a first acupoint, a maximum intensity thereof may be slowly increased, or increased in incremental units, until a sensation threshold is achieved thereabout the acupoint. The sensation threshold may be identified by the subject as a distinct sensation at the vicinity of the acupoint. Normally, the sensation is described as a pulsation or a twitch in the skin or a muscle. After determining the maximum intensity of the first stimulation signal, the maximum intensity thereof is kept fixed, and a second stimulation signal is applied at a second acupoint, a maximum intensity thereof is determined and kept fixed, and so on.

If needed, once the maximum intensities of all stimulation signals have been determined, the stimulation signals may be temporally shifted with respect to one another (i.e. synchronized) such as to deliver sequential neuro-stimulation at the acupoints pairs.

For crosswise neuro-stimulation, the determination of the maximum intensities may proceed by applying a stimulation signal at one acupoint pair at a time. At the beginning of a stimulation session, when a first stimulation signal is first applied at a first acupoint pair (i.e. by inducing a current through a conduction path in the body passing through/near both acupoints in a pair), then the maximum intensity of the stimulation signal may be slowly increased, or increased in incremental units, until a respective sensation threshold is achieved at the vicinity of each of the acupoints. The maximum intensity is then kept fixed. After determining the maximum intensity of the first stimulation signal, a second stimulation signal is applied at a second acupoint pair, a maximum intensity thereof determined and kept fixed, and so on.

If, however, the subject reports an onset of discomfort at the vicinity of one of the acupoints before the sensation threshold has been achieved in the vicinity of the other, then the maximum intensity may be slightly lowered and then kept fixed. Additionally or alternatively, one or both of the patches may be replaced with other patches having different electrodes geometries. For example, a percutaneous electrode may be used to replace a transcutaneous electrode at the vicinity of the acupoint where the sensation threshold has not been achieved, thereby potentially allowing for achieving the sensation threshold at a lower maximum intensity.

When implemented automatically, maximum intensities may be determined based on real-time or near real-time muscle contraction sensor data. For example, a muscle contraction sensor may be placed near each acupoint whereat neuro-stimulation is to be applied. At the beginning of a stimulation session, a maximum intensity of each the stimulation signals applied at each of the acupoints (local neuro-stimulation), or each of the acupoint pairs (crosswise neuro-stimulation), may be slowly increased or increased in incremental units. The increase in the maximum intensity of a stimulation signal delivered at an acupoint (local neuro-stimulation) is continued until a respective muscle contraction sensor indicates that a motor threshold in a region near the acupoint has been reached. The increase in the maximum intensity of a stimulation signal delivered at an acupoint pair (crosswise neuro-stimulation) is continued until a respective muscle contraction sensor indicates that a motor threshold in a region near one of the acupoints in the acupoint pair has been reached. The maximum intensity is then kept fixed. Alternatively, the increase in the neuro-stimulation delivered at the acupoint pair may be continued until muscle contraction sensors indicate that motor thresholds have been reached near both of the acupoints (unless the subject reports an onset of discomfort at the vicinity of one of the acupoints before the motor threshold has been achieved in the vicinity of the other, in which case the maximum intensity may be slightly lowered and then kept fixed.). The maximum intensity is kept fixed.

According to some embodiments, method 700 may further comprise step 720 of monitoring one or more of the physiological parameters, simultaneously with the neuro-stimulation. Stimulation parameters characterizing the stimulation signals, e.g. amplitude, maximum intensity, frequency, waveform, may be adjusted in real-time based on the monitored values of the one or more physiological parameters, particularly real-time HRV values. The adjustment may be performed automatically (e.g. by a processing circuitry and/or a loop feedback circuitry) or may be performed manually (by the trained professional).

According to some embodiments, step 720 comprises obtaining a signal indicative of temporal heart activity of the subject. The signal may be used to identify reference points therein, and their respective occurrence times. The onset of at least some of the neuro-stimulation pulses may be delayed relative to the occurrence times of respective reference points. For example, the signal may be an ECG signal, the reference points may be R peaks of normal beats, and an onset of each neuro-stimulation pulse (crosswise neuro-stimulation), or onsets of pulses in a neuro-stimulation pulse pair (local neuro-stimulation), may be timed to occur in a time interval beginning after at least 100 msec or after at least 200 msec, after the occurrence time of the R peak of a respective normal beat. Additionally or alternatively, the time by which the onset of each neuro-stimulation pulse or pulse pair is delayed relative to the occurrence time of the respective R peak may depend on an average of several NN intervals, e.g. be equal to one tenth, one fifth, one third, or even on half of the average of the last five, ten, or even twenty NN intervals.

According to some embodiments, a sequence of n≥2 pulses, delivered (crosswise) at n acupoint pairs, may be timed such as to be delayed by 100-500 msec relative to a respective R peak occurrence time. According to some embodiments, a cycle of sequences may be timed such as to be delayed by 100-500 msec relative to a respective R peak occurrence time. According to some embodiments, each pulse in a sequence is timed such as to be delayed by 100-500 msec relative to a respective R peak occurrence time. That is to say, a first pulse, applied at a first acupoint pair, is timed such as to be delayed by 100-500 msec relative to a first R peak occurrence time, while a second pulse, applied at a second acupoint pair, is timed such as to be delayed by 100-500 msec relative to a second R peak occurrence time, and so on. At least one of the acupoint pairs is a core acupoint pair.

According to some embodiments, a sequence of n≥2 paired stimulation pulses, delivered (locally) at n acupoint pairs, may be timed such as to be delayed by 100-500 msec relative to a respective R peak occurrence time. According to some embodiments, a cycle of sequences of paired pulses may be timed such as to be delayed by 100-500 msec relative to a respective R peak occurrence time. According to some embodiments, each pair of pulses in a sequence of paired pulses is timed such as to be delayed by 100-500 msec relative to a respective R peak occurrence time. That is to say, a first pulse pair, applied at a first acupoint pair, is timed such as to be delayed by 100-500 msec relative to a first R peak occurrence time, while a second pulse, applied at a second acupoint pair, is timed such as to be delayed by 100-500 msec relative to a second R peak occurrence time, and so on. At least one of the acupoint pairs is a core acupoint pair.

According to some embodiments, method 700 may further comprise following step 710, step 730 wherein one or more physiological parameters of the subject are measured. The physiological parameters may be measured immediately after the neuro-stimulation, and/or a few minutes after, for example, one minute, and/or five minutes, and/or ten minutes, and/or even thirty minutes, after. The physiological parameters may be stored in a memory (e.g. memory circuitry 128 or memory circuitry 428 when applying method 700 using system 100 or system 400, respectively) for future reference and/or transmitted to an online database, as described hereinbelow.

According to some embodiments, based on the measured values of the physiological parameters, another stimulation session may be recommended and steps 708 to 730 may be repeated.

According to another aspect of the invention, there is provided a method 800 for increasing a subject's HRV. Method 800 comprises a step 808 of obtaining a signal indicative of temporal heart activity of the subject, and a step 810 of neuro-stimulating a peripheral nerve by applying a stimulation signal at a respective acupoint located proximately to the peripheral nerve. The obtained signal may be used to identify reference points therein, and respective occurrence times thereof. According to some embodiments, the stimulation signal comprises a series of stimulation pulses. The onset of at least some of the stimulation pulses may be delayed relative to the occurrence times of respective reference points. For example, the obtained signal may be an ECG signal, the reference points may be R peaks of normal beats, and an onset of each stimulation pulse may be timed to be delayed by a time delay of 100-500 msec or 200-400 msec relative to the occurrence time of the R peak of a respective normal beat. According to some embodiments, the time delay depend on an average of several NN intervals, e.g. be equal to one tenth, one fifth, one third, or even one half of the average of the last five, ten, or even twenty NN intervals.

According to some embodiments, additional peripheral nerves may be electrically neuro-stimulated by applying additional series of stimulation pulses at additional acupoints. The onset of at least some of the additional stimulation pulses in each series of stimulation pulses may be delayed relative to the occurrence times of respective reference points. The delay of a stimulation pulse relative to the occurrence time of a respective reference points may differ from one series of stimulation pulses to another.

According to some embodiments, n≥2 stimulation signals, each comprising a series of stimulation pulses, are applied at n acupoints or acupoint pairs simultaneously. In particular, the delay time of a stimulation pulse relative to the occurrence time of a respective R peak is substantially the same across all the stimulation signals. For example, the onset of each of the stimulation pulses may be timed to occur about 200 msec after the respective R peak occurrence time. The acupoint pairs may be core acupoint pairs, but may also comprise non-core acupoint pairs, particularly acupoint pairs wherein both acupoints are associated with cardiovascular function. According to some embodiments, none of the acupoint pairs are core acupoint pairs.

According to some embodiments, a sequence of n≥2 pulses, delivered (crosswise) at n acupoint pairs, may be timed such as to be delayed by 100-500 msec relative to a respective R peak occurrence time (e.g. the sequence comprising stimulation pulses 360 and 364 in FIG. 3d). According to some embodiments, a cycle of sequences may be timed such as to be delayed by 100-500 msec relative to a respective R peak occurrence time (e.g. the cycle comprising two stimulation sequences in FIG. 3d: a first sequence of stimulation pulses 360 and 364 and a second sequence of stimulation pulses 362 and 366). According to some embodiments, each pulse in a sequence is timed such as to be delayed by 100-500 msec relative to a respective R peak occurrence time. That is to say, a first a pulse (e.g. stimulation pulse 380 in FIG. 3e), applied at a first acupoint pair, is timed such as to be delayed by 100-500 msec relative to a first R peak occurrence time, while a second pulse (e.g. stimulation pulse 382 in FIG. 3e), applied at a second acupoint pair, is timed such as to be delayed by 100-500 msec relative to a second R peak occurrence time, and so on.

According to some embodiments, a sequence of n≥2 paired stimulation pulses, delivered (locally) at n acupoint pairs, may be timed such as to fully occur fully occur in a 400 msec time interval beginning 100 msec after a respective R peak occurrence time (e.g. the sequence comprising paired pulses 612 and 614 and paired pulses 622 and 624 in FIG. 6a). According to some embodiments, a cycle of sequences of paired pulses may be timed such as to fully occur in a 400 msec time interval beginning 100 msec after a respective R peak occurrence time. According to some embodiments, each pair of pulses in a sequence of paired pulses is timed such as to fully occur in a 400 msec time interval beginning 100 msec after a respective R peak occurrence time. That is to say, a first pulse pair, applied at a first acupoint pair, is timed to fully occur in a 400 msec time interval beginning 100 msec after a first R peak occurrence time, while a second pulse, applied at a second acupoint pair, is timed to fully occur in a 400 msec time interval beginning 100 msec after a second R peak occurrence time, and so on.

Method 800 may further comprise steps similar to steps 702, 704, 706, 720, and 730, respectively. Method 800 may further incorporate features of steps 708 and 710, which have not been mentioned in the description of steps 806 and 810 (e.g. features such as determining maximum intensities of stimulation signals, as taught in step 708). In particular, method 800 may comprise adapting any of one the stimulation algorithms described in method 700, such as to synchronize the application of the stimulation signals relative to reference points in a signal indicative of temporal heart activity of the subject.

Method 700, method 800, and/or combinations thereof, may be used to achieve long-term HRV improvement through regular application thereof over an extended period of time, such as days, weeks, or even months. Sustention of long-term HRV improvement may require regular application of method 700 and/or method 800, for example, every day, every second day, once a week, or once a month. Method 700 and/or method 800 may also be used to achieve short-term HRV improvement through a single application thereof. Each application of method 700 or method 800, i.e. stimulation session, may take five minutes, twenty minutes, an hour, or even two hours. Each stimulation session may contribute incrementally to long-term HRV improvement. It is contemplated that long-term HRV improvement may help, for example, in the treatment of arrhythmias. Short-term HRV improvement may help, for example, in improving an efficacy of a physical workout and/or in improving sleep.

According to certain embodiments of the invention, a method 900 for treating cardiac arrhythmias and arrhythmia-related conditions by improving HRV is contemplated. As known in the art, there exists a correlation between decreased arrhythmia and increased mortality after myocardial infraction and decreased HRV. The inventor has found that increasing HRV—particularly, by delivering neuro-stimulation at acupoints pairs, comprising at least one core acupoint pair—may help treat various arrhythmias, including: pre-fibrillation, paroxysmal atrial fibrillation (PAF), persistent AF (PsAF), chronic AF (CAF), atrial tachycardia, ventricular premature complexes (VPCs), atrial premature complexes (APCs), SVT (Supraventricular tachycardia), and/or the like. The treatment may depend on triggers of arrhythmia for each subject (abdominal-gastrointestinal, chest congestion, stress, adrenal, vagal, etc.) Different treatment algorithms may be used for treating and preventing different arrhythmias (VPCs, APCs, atrial tachycardia, etc.).

Unexpectedly, the following stimulation algorithms for improving (i.e. increasing) HRV have been found by the inventor to be effective in treating various arrhythmias:

III. For decreasing arrhythmia, sequential crosswise/local neuro-stimulation in the following order:
  a. A left Ht7-right Sp6 acupoint pair.
  b. A right Ht7-left Sp6 acupoint pair.
  c. A left Pc6-right Ki6 acupoint pair.
  d. A right Pc6-left Ki6 acupoint pair.

IV. For decreasing arrhythmia, sequential crosswise/local stimulation in the following order:
  a. The left Ht7-right Sp6 acupoint pair.
  b. The right Ht7-left Sp6 acupoint pair
  c. The left Pc6-right Ki6 acupoint pair.
  d. The right Pc6-left Ki6 acupoint pair.

e. A Cv17-right Lv14 acupoint pair.
f. A Cv17-left Lv14 acupoint pair.
g. A Cv12-right St32 acupoint pair.
h. A Cv12-left St32 acupoint pair.

V. For preventative maintenance of a reduction in arrhythmia, sequential crosswise/local neuro-stimulation in the following order:
a. The left Ht7-right Sp6 acupoint pair.
b. The right Ht7-left Sp6 acupoint pair.
c. The left Pc6-right Lv3 acupoint pair.
d. The right Pc6-left Lv3 acupoint pair.

VI. For decreasing abdominally-gastrointestinally triggered arrhythmia, sequential neuro-stimulation in the following order:
a. The left Ht7-right Sp6 acupoint pair.
b. The right Ht7-left Sp6 acupoint pair.
c. The left Pc6-right Lv3 acupoint pair.
d. The right Pc6-left Lv3 acupoint pair.
e. A left Gb34-right Gb34 acupoint pair.

VII. For decreasing abdominally-gastrointestinally triggered arrhythmia, sequential crosswise/local neuro-stimulation in the following order:
a. The left Ht7-right Sp6 acupoint pair.
b. The right Ht7-left Sp6 acupoint pair.
c. The left Pc6-right Lv3 acupoint pair.
d. The right Pc6-left Lv3 acupoint pair.
e. The Cv12-right St32 acupoint pair.
f. The Cv12-left St32 acupoint pair.

VIII. For chest/MI/"mechanical" arrhythmia, sequential neuro-stimulation in the following order:
a. A left Pc6-right Lv14 acupoint pair.
b. A right Pc6-left Lv14 acupoint pair.
c. A left Ub14-right HUA T4 acupoint pair.
d. A right Ub14-left HUA T4 acupoint pair.
e. A left Ub15-right HUA T5 acupoint pair.
f. A right Ub15-left HUA T5 acupoint pair.

while substantially simultaneously delivering local neuro-stimulation at the Cv17 acupoint such that each of the stimulation pulses delivered at the acupoint pairs is substantially simultaneous to a respective stimulation pulse delivered at the Cv17 acupoint.

According to some embodiments, in each of the stimulation algorithms I-VIII, the stimulation signals may be delivered simultaneously or substantially at all acupoint pairs (and, if present, unpaired acupoints). According to some embodiments, in each of the stimulation algorithms I-VIII, the stimulation signals may be delivered in a different order than the respective order given above. In each of the stimulation algorithms III-VIII the stimulation signals may be similar to any one of the different embodiments of stimulation signal 300 listed in the description of stimulation signal 300 hereinabove in the Electrical neuro-stimulation system for improving HRV section. Results of treatment with some of the above-specified stimulation algorithms are presented in the Treatment results using an embodiment of system 100 section hereinbelow.

Figure 7:
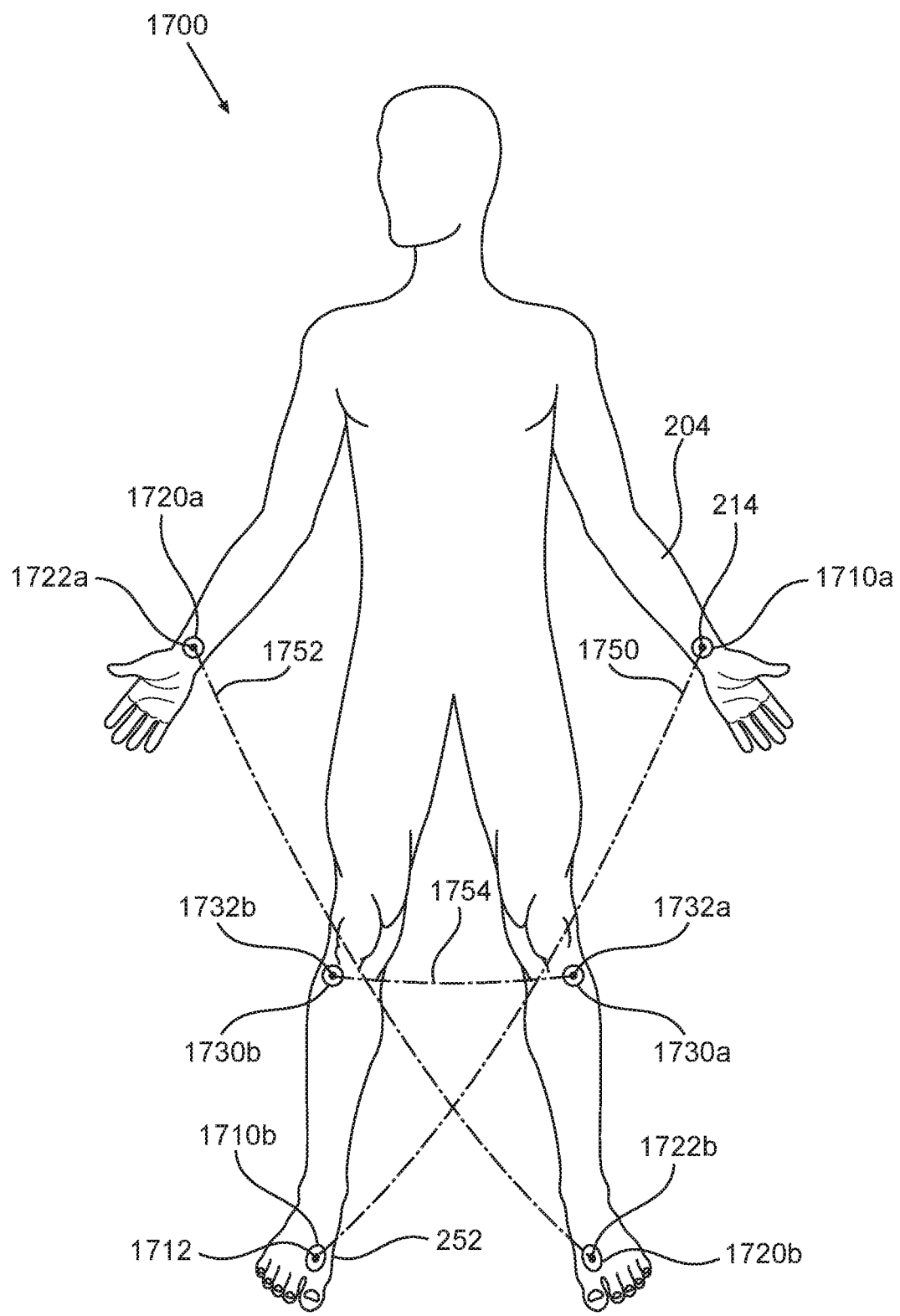
FIG. 7 schematically depicts placement of electrodes on acupoints according to a stimulation algorithm.

FIG. 7 schematically depicts placement of patches, such as first patch 136*a* or first WP 406*a*, on a body 1700 of a subject according to stimulation algorithm I. A first patch 1710*a* and a second patch 1710*b* are placed proximately to left Pc6 acupoint 214 and a right Lv3 acupoint 1712, respectively. First patch 1710*a* and second patch 1710*b* are configured to deliver simultaneous (i.e. when each comprises a single electrode) or substantially simultaneous electrical neuro-stimulation (i.e. when each comprises a pair of electrodes) at respective acupoints, as indicated by dashed-dotted line 1750. A third patch 1720*a* and a fourth patch 1720*b* are placed proximately to a right Pc6 acupoint 1722*a* and a left Lv3 acupoint 1722*b*, respectively. Third patch 1720*a* and fourth patch 1720*b* are configured to deliver simultaneous or substantially simultaneous electrical neuro-stimulation at respective acupoints, as indicated by dashed-dotted line 1752. Electrical neuro-stimulation A fifth patch 1730*a* and a sixth patch 1730*b* are placed proximately to a left St36 acupoint 1732*a* and a right St36 acupoint 1732*b*, respectively. Fifth patch 1730*a* and sixth patch 1730*b* are configured to deliver simultaneous or substantially simultaneous electrical neuro-stimulation at respective acupoints, as indicated by dashed-dotted line 1754.

It is to be understood that the above-mentioned stimulation pulses, signals, sequences, cycles, and algorithms are discussed solely by way of examples of effective treatments for modulating HRV, and for treating arrhythmias by modulating HRV, discovered by the inventor. Other acupoint pairings and stimulation parameters, etc., which may be useful for modulating HRV, and for treating arrhythmias by modulating HRV, are considered to be within the scope of the present invention.

Learning Methods for Heart-Rate Variability Improvement

Another aspect of the invention finds an embodiment in a learning method 1000 for HRV improvement, and treatment of arrhythmias, at a level of an individual (i.e. a single subject). Method 1000 comprises storing and analyzing session data of a subject undergoing stimulation sessions according to method 700, method 800, and/or method 900. The analysis of such data may allow for identifying and modifying stimulation algorithms adapted to the subject on an individual basis. Method 1000 comprises the steps of:

a. A step 1010 of storing session data of the subject in a memory. When the subject undergoes a stimulation session, session data are stored in the memory, e.g. memory circuitry 128 or memory circuitry 428 when the neuro-stimulation is delivered using system 100 or system 400, respectively. Alternatively or additionally, the session data may be sent to an online database and stored therein, as elaborated on hereinbelow.

b. A step 1020 wherein improved stimulation algorithms are determined by analyzing session data of the subject, including session data from previous stimulation sessions the subject has undergone, which is in the memory and/or in the online database. Step 1020 may be repeated when the subject undergoes another stimulation session.

More specifically, when the subject undergoes a stimulation session, before commencing the neuro-stimulation, during the neuro-stimulation, and/or after ending the neuro-stimulation, one or more of heart-rate, HRV, ECG, and/or optionally other physiological parameters (e.g. blood pressure) are measured, and the measurement results are stored in the memory and/or sent to the database. In addition, data characterizing the application of the neuro-stimulation (e.g. the stimulation algorithm) are stored in the memory and/or sent to the database, e.g. duration, amplitude, maximum intensity, frequency, waveform of each of the stimulation signals, temporal correlations between the stimulation signals, specification of whether the neuro-stimulation comprised local neuro-stimulation or crosswise neuro-stimulation or a combination thereof, acupoints whereat the stimulation signals were respectively applied and acupoint pairings, as well as any adjustments to the stimulation parameters effected during the neuro-stimulation. Finally, the session data (i.e. both data sets mentioned above) is dated.

The stored session data, including session data from previous stimulation sessions, may be analyzed using customized software (e.g. machine learning algorithms) to determine improved stimulation algorithms for future stimulation sessions. Different stimulation algorithms and corresponding sets of stimulation parameters may be determined for different respective stimulation session goals. Different stimulation algorithms and corresponding sets of stimulation parameters may be determined for different types of arrhythmias. According to some embodiments, the analysis may be performed on a controller, such as controller 102 or controller 402, e.g. by customized software installed on control module 120 or control module 420, respectively. The analysis may also be performed on a database computer associated with the online database, with the results of the analysis being communicated to the controller. According to some embodiments, session data may be analyzed even during the stimulation session, and the stimulation parameters may be accordingly adjusted during the stimulation session.

Yet another aspect of the invention finds an embodiment in a population-based learning method 1100 for HRV improvement and treatment of arrhythmias. Method 1100 comprises collecting personal data and session data from a population of subjects, which have undergone and/or undergo one or more stimulation sessions according to method 700, method 800, and/or method 900. Method 1100 further comprises analyzing the data (i.e. the personal data and the session data). The analysis of such data may allow for partitioning the population into subpopulations: Each subpopulation is characterized in that subjects therein respond similarly to identical or similar stimulation algorithms, which have been found to be effective for treatment. The analysis of such data may allow for identifying stimulation algorithms adapted to respective subpopulations or modifying stimulation algorithms such as to be better adapted to respective subpopulations. Method 1100 comprises the steps of:

a. A step 1110 of establishing a database storing session data of a population of subjects, which have undergone and/or undergo one or more stimulation sessions according to method 700 and/or method 800, optionally using an electrical neuro-stimulation system, such as system 100 or system 400. The database may be online, such as to be easily accessible.

b. A step 1120 of analyzing the data therein the database, such as to partition the population into subpopulations and to determine sets of stimulation parameters adapted to respective sub-populations.

c. A step 1130 of updating the database with new session data and/or new personal data.

More specifically, when a subject first undergoes a stimulation session, as taught hereinabove, personal data of the subject, is sent to the database. The personal data may comprise, age, gender, weight, medical history, and heart-function related symptoms.

When the subject undergoes a stimulation session, before commencing the neuro-stimulation, during the neuro-stimulation, and/or after ending the neuro-stimulation, one or more of heart-rate, HRV, ECG, and/or optionally other physiological parameters (e.g. blood pressure) are measured, and the measurement results are sent to the database. In addition, the stimulation session goal, the stimulation algorithms, and any adjustments made to the stimulation parameters (as listed in the description of method 1000) during the neuro-stimulation are sent to the database. The session data is dated and stored on the database in a file/directory of the subject.

Using a database computer associated with the database and installed with customized software (e.g. cluster analysis software), the data in the database may be analyzed using the customized software, such as to partition the population into subpopulations and determining stimulation algorithms adapted to respective subpopulations. A first partitioning into subpopulations may be effected according to the stimulation session goal. A subpopulation may also be characterized by one or more of age group (i.e. subjects who are in the same range of ages, e.g. twenty to thirty years), gender, a weight group (i.e. subjects weigh in a same range of weights), a common or similar medical history, common or similar heart-related activity symptoms, number and types of stimulation sessions underwent, response to previous stimulation sessions, and so on. Suitably defined distances or distance measures may be used to quantify the difference in the responses (e.g. as quantified by HRV parameters) of different subjects to stimulation sessions effected using identical or similar stimulation algorithms. The partitioning into subpopulations is such that the distances between the responses of different subjects within a subpopulation to similar neuro-stimulation are small. At a same time the number of subjects within most subpopulations may be restricted to be higher than a minimum number. Analysis of data of subjects within a subpopulation may allow for identifying more effective stimulation algorithms (e.g. by statistical analysis and/or pattern recognition software).

When new data is stored in the database (e.g. new session data, updates to personal data, new a subject personal data and first session data), or when a sufficient amount of new data is stored in the database, the data therein is analyzed and new subpopulation adapted sets of stimulation algorithms may be obtained. New partitions, and possibly finer partitions, of the population to sub-populations, may also be obtained.

When there is a change in the personal data of a subject, the database may be updated, for example, the next time the subject undergoes a stimulation session. Optionally, the subject may allow for updated personal data (e.g. changes in weight, changes in a medical condition, appearance of a new medical condition) to automatically be sent from his healthcare provider, physician, and/or the like, to the database.

The partitioning to subpopulations, allows for assigning a subject to a respective subpopulation. In particular, the first time a subject undergoes a stimulation session, a stimulation algorithm adapted to the subject at the level of the subpopulation may be used, thereby potentially increasing the efficacy of the neuro-stimulation. As the subject returns for additional stimulation sessions, the stimulation algorithms may be modified. The modification may be based at least in part on additional personal data and session data of other subjects (within the same subpopulation as the subject), which has been accumulated on the database (since the previous stimulation session underwent by the subject) and analyzed by the database computer. As additional personal data and session data of the subject, as well as other subjects, is accumulated and analyzed, the subject may switch from one subpopulation to another.

Applying the Disclosed Methods Using the Disclosed Systems

A first exemplary stimulation session is described, wherein a trained professional uses system 100 to deliver neuro-stimulation to a subject, according to the methods disclosed hereinabove. The stimulation session is assumed to be the subject's first. The first exemplary stimulation session comprises:

1. In a step such as step 702, using user control interface 124, entering personal data of the subject into controller 102. The data is transmitted to the online database, and the database computer assigns the subject to a respective subpopulation. Subpopulation stimulation algorithms, e.g. suggested stimulation algorithms per stimulation session goal, are downloaded from the database to controller 102 (i.e. to memory circuitry 128).
2. Laying a subject in an appropriate posture with exposed arms, legs, torso, abdomen, chest, and upper back.
3. In a step combing steps such as step 704 and step 808, performing an ECG measurement on the subject using an external ECG monitor. The results of the ECG measurement are communicated to control module 120. The ECG measurement is continued uninterrupted (i.e. an ECG signal is continuously obtained).
4. In a step such as step 706, entering into controller 102 a stimulation session goal.
5. In a step such as step 708, a suggested stimulation algorithm, including stimulation parameters and acupoint pairs to be stimulated, is determined by control module 120 based on the suggested stimulation algorithm per the stimulation session goal, as well as on and the ECG measurement results. The suggested stimulation parameters are displayed on user control interface 124. At the trained professional's discretion, the acupoint pairings, as well as the suggested stimulation parameters (e.g. the duration of the session, frequencies and waveforms of stimulation signals) may be modified. Stimulation algorithm II is selected.
6. A first pair of patches, such as first patch pair 104, is placed over a first core acupoint pair, comprising the left Ht7 acupoint and the right Sp6 acupoint. A first patch and a second patch of the first patch pair are placed proximately to the left Ht7 acupoint and proximately to the right Sp6 acupoint, respectively. A second pair of patches, such as first patch pair 104, is similarly placed over a second core acupoint pair, reciprocal to the first core acupoint pair.
7. A third pair of patches, such as first patch pair 104, is placed over a third core acupoint pair, comprising the left Pc6 acupoint and the right Lv3 acupoint. A first patch and a second patch of the third pair are placed proximately to the left Pc6 acupoint and proximately to the right Lv3 acupoint, respectively. A fourth pair of patches, such as first patch pair 104, is similarly placed over a fourth core acupoint pair, reciprocal to the third acupoint core pair.
8. A fifth pair of patches, such as first patch pair 104, is placed over a fifth acupoint pair, comprising the left St36 acupoint and the right St36 acupoint. A first patch and a second patch of the fifth pair are placed proximately to the left St36 acupoint and proximately to the right St36 acupoint, respectively.
9. A first stimulation signal, essentially similar to stimulation signal 300, is applied at the first acupoint pair and a maximum intensity thereof is determined based on tactile sensation. The maximum intensity is kept fixed and a second stimulation signal, essentially similar to stimulation signal 300, is then applied at the second acupoint pair. A maximum intensity of the second stimulation signal is determined based on tactile sensation, and so on, until maximum intensities of five stimulation signals have been determined, as explained hereinabove in the description of step 708.
10. In a step such as step 810, the stimulation signals are temporally shifted with respect to one another, such as to deliver the neuro-stimulation sequentially at the acupoint pairs, i.e. a first stimulation pulse is applied at the first acupoint pair, a second stimulation pulse is then applied at the second acupoint pair, and so on, until a fifth stimulation pulse is applied at the fifth acupoint pair. The sequence of stimulation pulses is then repeated and synchronized relative to the ECG signal from the external ECG monitor. A duration of each stimulation sequence is selected such as to be smaller than 400 msec. An onset of a first stimulation pulse in each sequence is timed to occur 200 msec after an occurrence time of an R peak of a respective normal beat, as explained in the description of step 810.
11. In step such as step 720, one or more physiological parameters are monitored (i.e. beyond the occurrence times of R peaks) using sensors on the patches, e.g. first sensor 162a on first patch 106a, and/or one or more external monitors, such as the ECG monitor. The physiological parameters are displayed on user control interface 124 display. The stimulation parameters, characterizing the stimulation signals, are automatically adjusted in real-time by control module 120, based on the monitored values of the one or more physiological parameters. The trained professional may decide to disable the automatic adjustment of the stimulation parameters, and adjust the stimulation parameters by himself.
12. Saving session data into memory circuitry 128 and transmitting the session data to the online database.
13. Five minutes after the session has ended, in a step such as step 730, one or more of the physiological parameters of the subject are re-measured. Based on the re-measured values, neuro-stimulation may be applied again with the stimulation parameters possibly adjusted.

A second exemplary stimulation session is described, wherein the trained professional uses system 400 to deliver neuro-stimulation to a subject, according to the methods disclosed hereinabove, and in particular, method 900. The subject is assumed to have already undergone stimulation sessions, and is assumed to be treated for chest/MI/"mechanical" arrhythmia. The second exemplary stimulation session comprises:

1. In a step such as step 702, using user control interface 424, heart-related symptoms reported by the subject and any updates to the subject's medical history are entered into controller and 402 and transmitted onto the online database.
2. Laying a subject in an appropriate posture with exposed arms, legs, torso, abdomen, chest, and upper back.
3. In a step such as step 704, performing an ECG measurement on the subject using an external ECG monitor. The results of the ECG measurement are communicated to control module 420.
4. In a step such as step 706, using user control interface 424, entering into controller 402 a stimulation session goal (i.e. treatment of chest/MI/"mechanical" arrhythmia).
5. In a step such as step 708, a suggested stimulation algorithm, including stimulation parameters and acupoint pairs to be stimulated, is determined by control module 420 and displayed on user control interface 424. At the trained professional's discretion, the acupoint pairings, as well as the suggested stimulation parameters may be modified. Stimulation algorithm II is selected.
6. A first pair of WPs, such as first WP pair 404, is placed over a first core acupoint pair, comprising the left Pc6 acupoint and the right Lv14 acupoint. A first WP and a second WP of the first pair are placed proximately to the left Pc6 acupoint and the right Lv14 acupoint, respectively. A second pair of WPs, such as first WP pair 404, is similarly placed over a second core acupoint pair, reciprocal to the first acupoint pair.
7. A third pair of WPs, such as first WP pair 404, is placed over a third acupoint pair, comprising the left Ub14 acupoint and the right HUA T4 acupoint. A first WP and a second WP of the third pair are placed proximately to the left Ub14 acupoint and the right HUA T4 acupoint, respectively. A fourth pair of WPs, such as first WP pair 404, is similarly placed over a fourth acupoint pair, reciprocal to the third acupoint pair.
8. A fifth pair of WPs, such as first WP pair 404, is placed over a fifth acupoint pair, comprising the left Ub15 acupoint and the right HUA T5 acupoint. A first WP and a second WP of the fifth pair are placed proximately to the left Ub15 acupoint and the right HUA T5 acupoint, respectively. A sixth pair of WPs, such as first WP pair 404, is similarly placed over a sixth acupoint pair, reciprocal to the fifth acupoint pair.
9. A single WP, such as first WP 406a, is placed over the Cv17 acupoint.
10. Stimulation signals are simultaneously applied at each of the acupoints. Each of the stimulation signals comprises a series of stimulation pulses. Respective maximum intensities of the stimulation signals are determined: A maximum intensity of each stimulation signal is automatically slowly increased until a muscle contraction sensor, in a respective WP, signals that a motor threshold in the vicinity of the respective acupoint has been reached, as described hereinabove. The maximum intensities are kept fixed.
11. The stimulation signals are adjusted such that the stimulation signals delivered at each acupoint in a pair are on phase and identical, up to a possible difference in the maximum intensities. The paired stimulation signals are temporally shifted with respect to one another, one pair with respect to another, such as to deliver the neuro-stimulation sequentially at the acupoint pairs, i.e. a first pair of stimulation pulses is simultaneously applied at the first acupoint pair, a second pair of stimulation pulses is then simultaneously applied at the second acupoint pair, and so on, until a sixth pair of stimulation pulses is applied at the sixth acupoint pair. The stimulation signal delivered at the Cv17 acupoint is such as to be simultaneous with all the stimulation signals, i.e. when the first pair of stimulation pulses in a sequence is applied, a respective stimulation pulse is applied at the Cv17 acupoint, identical to the first pair of pulses up to a possible difference in maximum intensities. Then when the second pair of stimulation pulses in the sequence is applied, a respective stimulation pulse is applied at the Cv17 acupoint, identical to the second pair of pulses up to a possible difference in maximum intensities, and so on. The sequence of stimulation pulses is then repeated, as explained in the description of step 710.
12. In step such as step 720, monitoring one or more physiological parameters using sensors on the patches, e.g. first sensor 458a on first patch 406a, and/or one or more external monitors, such as an ECG monitor. The physiological parameters are displayed on control user control interface 424 display. The stimulation parameters, characterizing the stimulation signals, are automatically adjusted in real-time by control module 420, based on the monitored values of the one or more physiological parameters. The trained professional may decide to disable the automatic adjustment of the stimulation parameters, and adjust the stimulation parameters himself.
13. Saving session data into memory circuitry 428 and transmitting the session data to the online database.
14. Five minutes after the session has ended, in a step such as step 730, one or more of the physiological parameters of the subject are re-measured. Based on the re-measured values, neuro-stimulation may be applied again with the stimulation parameters possibly adjusted.

Treatment Results Using an Embodiment of System 100

Figure 8A:
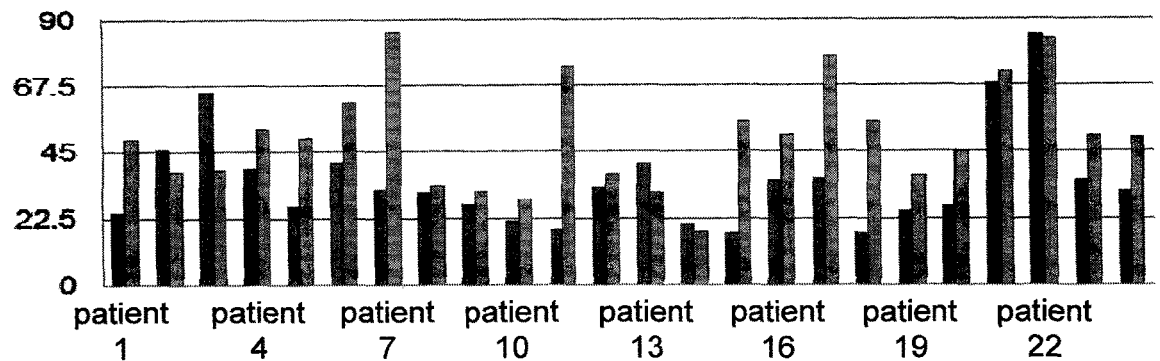
FIG. 8a presents SDNNs of 22 subjects before and after HRV improving stimulation sessions, as taught herein.
Figure 8B:
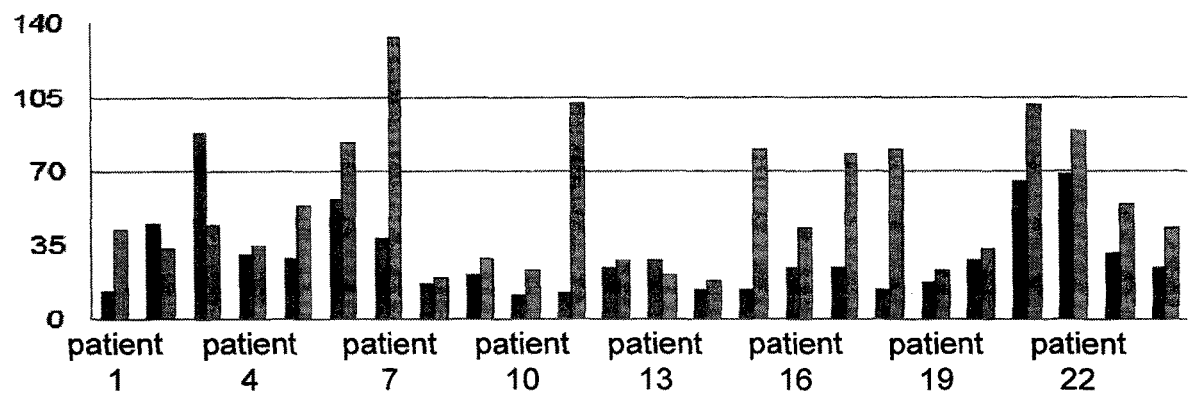
FIG. 8b presents rMSSDs of the 22 subjects of FIG. 8a before and after the HRV improving stimulation sessions.
Figure 8C:
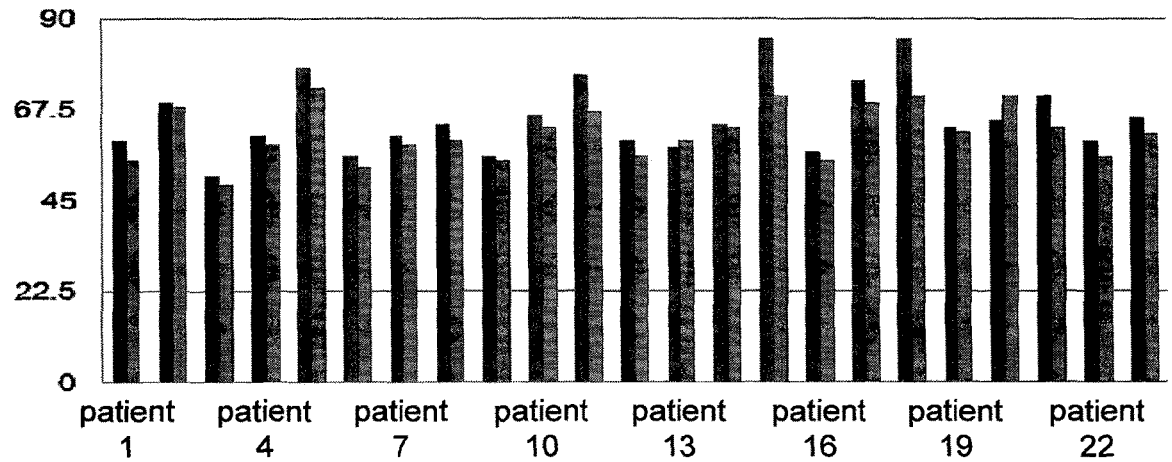
FIG. 8c presents heart-rates of the 22 subjects of FIG. 8a before and after the HRV improving stimulation sessions.

Results of treatments, using the methods disclosed herein, and an embodiment of system 100, are presented. FIGS. 8a-8c present results of HRV improving stimulation sessions performed on 22 subjects according to method 700. Each subject underwent one of two stimulation session variants. A first variant involved delivering neuro-stimulation simultaneously at three acupoint pairs: a first core acupoint pair comprising the left Pc6 acupoint and the right Lv3 acupoint, a second acupoint pair comprising the right Pc6 acupoint and the left Lv3 acupoint, and a third acupoint pair comprising the left St36 acupoint and the right St36 acupoint. The first acupoint pair and the second acupoint are each core acupoint pairs, as well as being reciprocal to one another. The second variant involved simultaneously neuro-stimulating five acupoint pairs: the three acupoint pairs of the first variant, as well as a fourth pair comprising the left Ht7 acupoint and the right Sp6 acupoint, and a fifth comprising the right Ht7 acupoint and the left Sp6 acupoint. The third acupoint pair and the fourth acupoint pair are each core acupoint pairs, as well as being reciprocal to one another.

In both the first variant and the second variant the neuro-stimulation was crosswise and comprised applying a respective bi-phasic symmetrical stimulation signal, such as stimulation signal 300, at each acupoint pair. The stimulation signals were applied simultaneously. Each of the stimulation signals comprised a series of square wave stimulation pulses, with a same stimulation pulse width, between 0.4-0.6 msec. Each of the stimulation signals had a same stimulation signal frequency, between 0.5-5 Hz. Respective stimulation pulses were applied simultaneously, i.e. the stimulation signals were in phase.

FIG. 8a displays a diagram comprising 24 column pairs. In each of the first 22 column pairs (i.e. the 22 leftmost column pairs), each pair of columns corresponds to a respective subject: a left column in a pair represents an SDNN of the respective subject immediately before the stimulation session and the right column in a pair represents the SDNN of the respective subject immediately after the stimulation session. The last two pairs of columns represent a mean SDNN (i.e. an average taken over a respective set of SDNNs of the subjects) and median SDNN (a median of the respective set of SDNNs of the subjects) before the stimulation session (the left column in a respective pair) and after the session (the right column in a respective pair). The results show a 41.77% increase in the mean SDNN after the stimulation session as compared to before the stimulation session. 17 out of 22 of the subjects, i.e. 77.2% of the subjects, exhibited an increase in SDNN following the session.

Similarly to FIG. 8a, FIG. 8b also displays a diagram comprising column pairs, the difference being that each column now represents a root mean square of successive differences (rMSSD) rather than SDNN. rMSSD is defined as a square root of an average taken over a set of squares of differences between adjacent NN intervals. The results show a 74.47% increase in a mean rMSSD of the subjects after the stimulation session as compared to before the stimulation session. 19 out of 22 of the subjects, i.e. 86.3% of the subjects, exhibited an increase in rMSSD following the session.

Similarly to FIG. 8a, FIG. 8c also displays a diagram comprising column pairs, the difference being that each column now represents a heart-rate rather than SDNN. The results show a 5.76% decrease in a mean heart rate of the subjects after the stimulation session as compared to before the stimulation session. 21 out of 22 of the subjects, i.e. 95.4% of the subjects, exhibited a decrease in heart-rate following the session.

Tables 1 and FIGS. 9a-9d presents results of treating various cardiac arrhythmias according to method 900, using an embodiment of system 100. Table 1 summarizes the results. 45 subjects with various, non-emergency, cardiac arrhythmias underwent a total of 488 electrical stimulation sessions as taught by method 900. An ECG measurement was conducted immediately before and immediately after each treatment (i.e. stimulation session), and ECG readings were compared for analysis. Each subject underwent a 25 minute session once a week over a period of 8 to 12 weeks.

nea on exertion, shortness of breath, pounding heart beat). One subject with CAF experienced cardioversion to normal sinus rhythm, a response never before recorded for this condition.

The results show outstanding efficacy in subjects with VPCs, with more than 80% experiencing complete remission with no episodes of VPC reported or seen on an ECG reading after completing a full treatment program (i.e. 8 to 12 sessions). One subject with persistent atrial tachycardia (3 weeks continuously), who was scheduled for hospital-based electrical shock cardioversion, experienced cardioversion after two sessions (2 days apart) and was able to avoid this procedure. The subject was monitored by her cardiologist throughout the treatment program.

One subject who was diagnosed by his cardiologist with frequent VPCs performed a 24 hour Holter monitoring exam before and after a treatment program of 8 stimulation sessions. Before the program an average of 443 VPCs were detected each hour with a total of 10,553 VPB over 24 hours (10.3% of total heart beats, which is considered severe). An ECG measurement before and after each session showed a reduction by half of VPB events, which remained stable from week to week. In a repeated Holter examination after completing the program, no arrhythmia was detected.

Figure 9A:
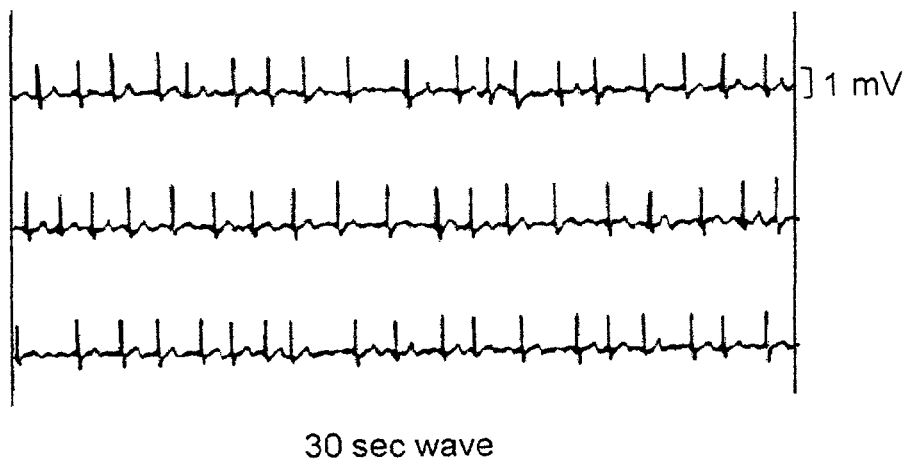
FIG. 9a presents results of an ECG reading of a subject with PAF before a neuro-stimulation session, as taught herein.
Figure 9B:
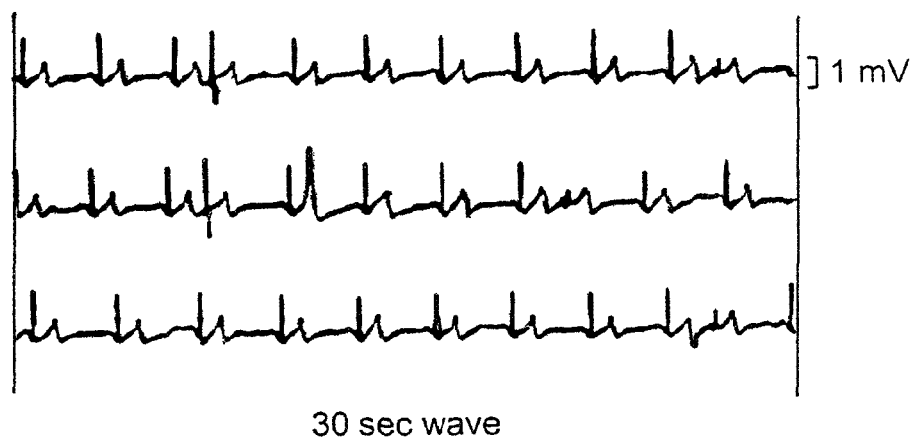
FIG. 9b presents results of an ECG reading of the subject of FIG. 9a after the neuro-stimulation session.

Examples of ECG readings before and after a stimulation session conducted with system 100 are presented in FIGS. 9a and 9b, and FIGS. 9c and 9d. FIGS. 9a and 9b present results of an exemplary session undergone by a subject with PAF during an 8 hour AF episode. FIG. 9a is an ECG reading of the subject from before the session and FIG. 9b is an ECG reading of the same subject one hour later, after the session. As compared to before the session, after the

TABLE 1

| Type of Arrhythmia | PAF | CAF | VPC | Atrial tachycardia | Atrial flutter | APC | SVT |
|---|---|---|---|---|---|---|---|
| Number of subjects | 17 | 5 | 16 | 1 | 3 | 1 | 2 |
| Subjects w/ >10% heart-rate reduction | 10 (during PAF) | 5 | 13 | 1 | 1 | 1 | 0 |
| Subjects w/ abnormal beats reduction | NA | NA | 13 out of 16 | 1 | 1 | 1 | 0 |
| Conversion to sinus rhythm during treatment program | 6 out of 12 | 1 (?) | NA | 1 | 0 | NA | 0 |
| Subjects w/ physical symptom reduction | >60% | >60% | >90% | 100% | 33% | 100% | NA |
| Reduction in number of episodes | 7 out of 17 | NA | >80% (13 complete remissions) | 100% | >33% (1 complete remission) | 100% | 1 with aggravation |

The results show clinical efficacy in the majority of the arrhythmic conditions treated. In some conditions, the effect was immediate, as observed by the comparison of ECG reading (i.e. signal) from before and after the session. In other conditions, the effect was cumulative and was observed from week to week.

In particular, cardioversion to normal sinus rhythm occurred in 50% of the subjects with PAF (6 out of 12). Cardioversion occurred within 6 to 25 minutes after starting to apply the neuro-stimulation. In addition, all 5 subjects with CAF experienced reduction of basal heart-rate, and 3 reported improvement in clinical symptoms (such as dyspsession heart-rate was lower (decreasing from 112 to 62), heart rhythm was more regular, and AF was converted to normal sinus rhythm as evidenced by the ECG P-waves that were missing in the ECG reading before the session, and which are present in the reading after the session. Some VPCs were present after the session but disappeared spontaneously after 30 minutes (ECG reading not shown).

Figure 9C:
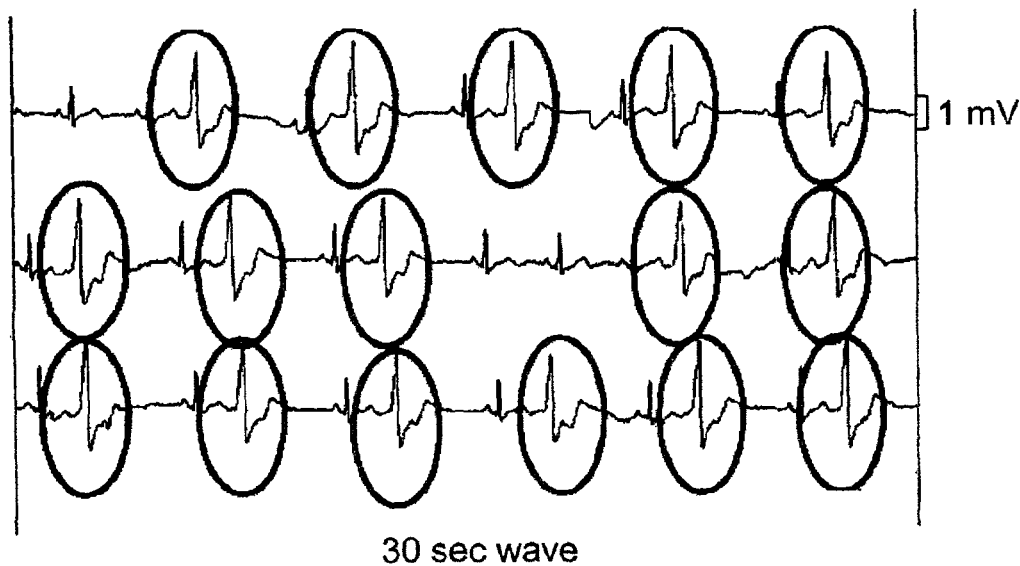
FIG. 9c presents results of an ECG reading of a subject with VPC before a neuro-stimulation session, as taught herein.
Figure 9D:
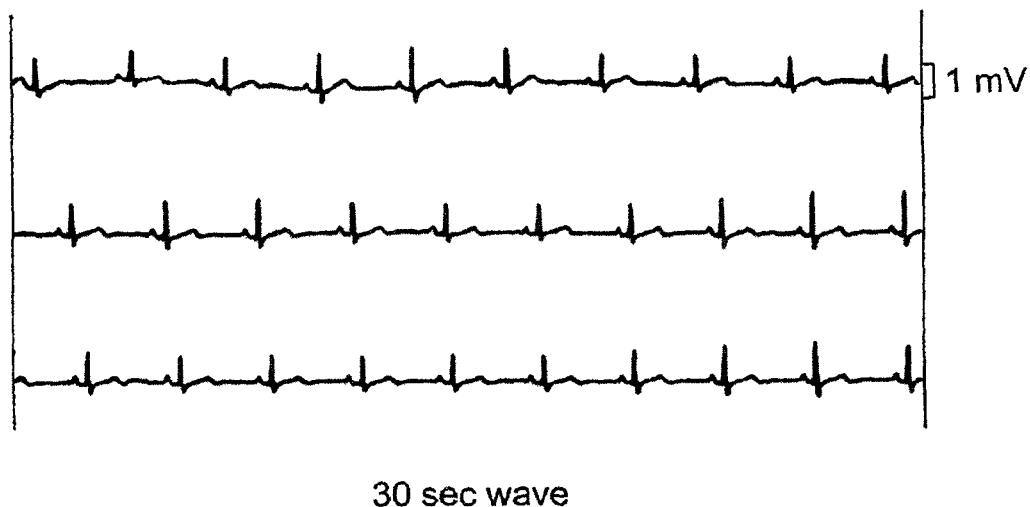
FIG. 9d presents results of an ECG reading of the subject of FIG. 9c after the neuro-stimulation session.

FIGS. 9c and 9d present results of an exemplary session undergone by a subject with frequent premature heart beats—VPCs (ventricular premature complexes). FIG. 9c is an ECG reading of the subject from before the session (VPCs are circled), and FIG. 9d is an ECG reading of the same subject 31 minutes after the session. As compared to before the session, after the session heart-rate was lower (decreasing from 71 to 58), and all VPC beats (32 per minute, representing more than 50% of all heart beats) were resolved.

A frequency of the electrical stimulation signals in all of the above examples was set between 0.5-5 Hz, with a milli-ampere bi-phasic symmetrical waveform and a pulse width of 0.4-0.6 milliseconds. Intensity was increased incrementally until all electrodes where reported by the patient as responsive. A sequential pair stimulation routine was used.

The above-mentioned cases and corresponding treatments are discussed solely by way of examples of effective treatment discovered by the inventor. Other electrode arrangements and sets of stimulation parameters may be useful for the above-mentioned conditions, as well as for other arrhythmic conditions, and are considered to be within the scope of the present invention.

Thus, according to an aspect of some embodiments, there is presented a system (100; 400) for increasing the HRV of a subject. The system comprises a control module (120; 420) and at least one neuro-stimulation unit (122; 452a), functionally associated with the control module and configured to generate an electrical neuro-stimulation comprising stimulation signals (300). The system further comprises at least two electrodes (136a and 136b; 436a1 and 436a2), configured to be removably attachable onto the skin of the subject. Each electrode is electrically connected to one of the at least one neuro-stimulation unit, and thereby configured to deliver the electrical neuro-stimulation signal to the skin. As seen in FIG. 1a, electrodes 136a and 136b are each connected to neuro-stimulation unit 122. As seen in FIG. 4a, electrodes 436a1 and 436a2 are each connected to neuro-stimulation unit 452a.

The control module is configured to obtain occurrence times of reference points associated with heart beats of the subject (e.g. occurrence times of R peaks 370 of ECG signal 356). The control module is further configured to controllably determine parameters of the stimulation signal generated by the neuro-stimulation unit. The stimulation parameters are determined such as to synchronize the stimulation signal with the occurrence times (as seen in FIGS. 3d and 3e and in FIG. 6a).

The system is configured to apply one of the stimulation signals via the first electrode proximately to an acupoint not associated with cardiovascular function, and thereby to increase the HRV of the subject.

According to some embodiments, the acupoint not associated with cardiovascular function is selected from the group consisting of left Sp6 acupoint, right Sp6 acupoint, left Ki6 acupoint, right Ki6 acupoint (274), left St36 acupoint (1732a), right St36 acupoint (1732b), left Lv14 acupoint, right Lv14 acupoint, Cv12 acupoint, left St32 acupoint, right St32 acupoint, left Lv3 acupoint (1722b), right Lv3 acupoint (1712), left Li4, and right Li4 acupoint.

According to some embodiments, the system is further configured to apply one of the stimulation signals via the second electrode proximately to an acupoint associated with cardiovascular function. According to some embodiments, the acupoint associated with cardiovascular function is selected from the group consisting of the left Ht7 acupoint, right Ht7 acupoint, left Pc6 acupoint (214), right Pc6 acupoint (1720a), left Gb34 acupoint, right Gb34 acupoint, left Ub14 acupoint, right Ub14 acupoint, left Ub15 acupoint, right Ub15 acupoint, left HUA T4 acupoint, right HUA T4 acupoint, left HUA T5 acupoint, right HUA T5 acupoint, and Cv17 acupoint.

For example, in FIG. 2a first electrode 136a is attached onto the skin proximately to Pc6 acupoint 214, which is associated with cardiovascular function, while second electrode 136b is attached onto the skin proximately to Ki6 acupoint 274, which is not or not known to be associated with cardiovasvular function.

According to some embodiments, the control module is further configured to receive a heart activity signal (e.g. ECG signal 356) indicative of temporal heart activity of the subject and to identify reference points in the heart activity signal (e.g. R peaks 370, 392, 394), thereby obtaining the occurrence times of the reference points associated with the heart beats of the subject. According to some embodiments, the heart activity signal is an ECG signal. According to some embodiments, the reference points are indicative of occurrence times of R peaks of heart beats of the subject.

According to some embodiments, the stimulation signal comprises pulses (360, 362, 364, 366, 380, 382, 612, 614, 622, 624) synchronized with the occurrence times of the reference points (as seen in FIGS. 3d and 3e, and in FIG. 6a). According to some embodiments, the pulses have a pulse width smaller than 1 msec and a maximum voltage intensity smaller than 60 V. According to some embodiments, the pulses are biphasic pulses (e.g. 310, 360, 362, 364, 366, 612, 614, 622, 624). According to some embodiments, each pulse is delayed relative to a preceding R peak by a time delay between about 100 msec and about 500 msec. In FIG. 3d stimulation sequences 350 and 352 are both delayed relative to respective R peaks 370. In FIG. 3d, each of stimulation sequences 350 and 352 is delayed relative to respective R peaks 370. In FIG. 3e, each of stimulation pulses 380 is delayed relative to a respective first peaks 392 of a respective R peak pair 390. Each of stimulation pulses 382 is delayed relative to a respective second R peak 394 of a respective R peak pair 390. In FIG. 6a, each of stimulation pulses 612, 614, 622, and 624 is delayed relative to a respective R peak 370.

According to some embodiments, the system comprises at least two electrode pairs (electrodes 136a and 136b and electrodes 136c and 136d; electrode pairs 436a, 436b, 436c, and 436d). According to some embodiments, the at least two electrodes are embedded on patches, the patches being configured to be removably attachable onto the skin. For example, electrodes 136a and 136b are embedded in/on patches 106a and 106b, respectively. According to some embodiments, each of the patches accommodates an electrode pair consisting of two electrodes. For example, electrode pairs 436a and 436b are embedded in/on patches 406a and 406b, respectively.

According to some embodiments, each of the patches has one of the at least one neuro-stimulation unit accommodated therein. For example, patches 406a and 406b accommodate stimulation units 458a and 458b, respectively. According to some embodiments, each of the patches further accommodates a wireless receiver functionally associated with said neuro-stimulation unit accommodated on said patch. According to some embodiments, the receiver is a transceiver (e.g. wireless transceivers 454a and 454b).

According to some embodiments, the at least one neuro-stimulation unit consists of a single neuro-stimulation unit and the electrodes on the patches are wired thereto. In FIG. 1a system 100 comprises on neuro-stimulation, neuro-stimulation unit 122, and electrodes 136a and 136b (embedded in/on patches 106a and 106b, respectively) are electrically connected to neuro-stimulation unit 122 via conduction cables 152a and 152b, respectively.

According to some embodiments, the patches further accommodate a sensor functionally associated with the control module and configured to measure at least one physiological parameter of the subject (e.g. sensors 162a and 162b on patches 106a and 106b, respectively; sensors 458a and 458b on patches 406a and 406b, respectively). According to some embodiments, the sensor is selected from the group consisting of an IR sensor for measuring heart-rate, an accelerometer for measuring heart-rate, an impedance meter for measuring skin electrical resistance, a surface EMG sensor for measuring muscle activity and degree of contraction, a blood-pressure sensor, and a thermometer for measuring skin temperature. According to some embodiments, the control module is configured to vary a maximum intensity and/or amplitude of stimulation signals according to a physiological parameter measured by the sensor.

According to an aspect of some embodiments, there is presented a method for increasing the HRV of a subject. The method comprises delivering electrical neuro-stimulation at at least one core acupoint pair (acupoints 214 and 274; acupoints 214 and 1712; acupoints 1722a and 1722b) by applying an electrical stimulation signal at the acupoints. The core acupoint pair comprises a first acupoint associated with cardiovascular function (214; 1772a) and a second acupoint not associated with cardiovascular function (274; 1712; 1722b).

According to some embodiments, the electrical neuro-stimulation is delivered by a first pair of electrodes (e.g. 104) applying a first electrical stimulation signal (310) at the acupoints. A first electrode (136a) of the pair is attached onto the skin of the subject proximately to the first acupoint (e.g. 214) and the second electrode (136b) of the pair is attached onto the skin of the subject proximately to the second acupoint (e.g. 274).

According to some embodiments, the electrical neuro-stimulation is delivered by two pairs of electrodes (e.g. electrode pairs 406a and 406b). A first electrode pair is attached onto the skin of the subject proximately to the first acupoint (e.g. 214), applying a first electrical stimulation signal at the first acupoint (e.g. 310a; 612). The second electrode pair is attached onto the skin of the subject proximately to the second acupoint (e.g. 1712), applying a second electrical stimulation signal at the second acupoint (e.g. 310b; 614).

According to some embodiments, the first signal applied at the first acupoint and the second signal applied at the second acupoint comprise repetitive pulses at an equal repetition rate, and the pulses of the first signal are substantially simultaneous with the pulses of the second signal (in FIG. 6a pulses 612 and 614 are substantially simultaneous, as are pulses 622 and 624).

According to some embodiments, the first signal applied at the first acupoint and the second signal applied at the second acupoint comprise repetitive pulses at an equal repetition rate, and the pulses of the first signal are partially simultaneous with the pulses of the second signal (e.g. pulses 612 and 614 in FIG. 6b and in FIG. 6c).

According to some embodiments, the first signal and the second signal comprise repetitive pulses at an equal repetition rate, and the pulses of the first signal do not overlap with the pulses of the second signal (pulses 310a and 310b in FIG. 3b).

According to some embodiments, the method of claim further comprises delivering electrical neuro-stimulation by a second pair of electrodes (180) applying a second electrical stimulation signal at a second core acupoint pair. A first electrode (136c) of the second pair is attached onto the skin of the subject proximately to a first acupoint of the second acupoint pair and the second electrode (136b) of the second pair is attached onto the skin of the subject proximately to a second acupoint of the second acupoint pair. For example, in FIG. 7 a first patch pair 1710a and 1710b, are attached over a first core acupoint pair (214 and 1712). A second patch pair 1720a and 1720b, are attached over a second core acupoint pair (1722a and 1722b). Patches 1710a and 1710b may be essentially similar to patches 106a and 106b, each comprising a single electrode such as electrode 136a and 136b, respectively. Similarly, patches 1720a and 1720b may be essentially similar to patches 106c and 106d, each comprising a single electrode such as electrode 136c and 136b, respectively.

According to some embodiments, the first signal applied at the first core acupoint pair (214 and 274; 214 and 1712) and the second signal applied at the second core acupoint pair (1722a and 1772b) comprise repetitive pulses, and the pulses of the first signal are simultaneous with the pulses of the second signal.

According to some embodiments, the first signal applied at the first core acupoint pair (214 and 274; 214 and 1712) and the second signal applied to the second core acupoint pair (1722a and 1772b) comprise repetitive pulses, and the pulses of the first signal (310a in FIG. 3c) are partially simultaneous with the pulses of the second signal (310b in FIG. 3c).

According to some embodiments, the first signal and the second signal comprise repetitive pulses, and the pulses of the first signal (310a in FIG. 3b) do not overlap with the pulses of the second signal (310b in FIG. 3b).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. No feature described in the context of an embodiment is to be considered an essential feature of that embodiment, unless explicitly specified as such.

Although steps of methods according to some embodiments may be described in a specific sequence, methods of the invention may comprise some or all of the described steps carried out in a different order. A method of the invention may comprise all of the steps described or only a few of the described steps. No particular step in a disclosed method is to be considered an essential step of that method, unless explicitly specified as such.

Although the invention is described in conjunction with specific embodiments thereof, it is evident that numerous alternatives, modifications and variations that are apparent to those skilled in the art may exist. Accordingly, the invention embraces all such alternatives, modifications and variations that fall within the scope of the appended claims. It is to be understood that the invention is not necessarily limited in its application to the details of construction and the arrangement of the components and/or methods set forth herein. Other embodiments may be practiced, and an embodiment may be carried out in various ways.

The phraseology and terminology employed herein are for descriptive purpose and should not be regarded as limiting. Citation or identification of any reference in this application shall not be construed as an admission that such reference is available as prior art to the invention. Section headings are used herein to ease understanding of the specification and should not be construed as necessarily limiting.

The invention claimed is:

1. A system comprising:
   a control module;
   at least one neuro-stimulation unit, functionally associated with said control module and configured to generate electrical neuro-stimulation comprising stimulation signals, and
   at least a first electrode and a second electrode, configured to be removably attachable onto skin of a subject, wherein each electrode is electrically connected to one of said at least one neuro-stimulation unit for delivering said stimulation signal to the skin;
   wherein said control module is configured to:
   receive a heart activity signal indicative of temporal heart activity of the subject and to identify reference points in the heart activity signal, thereby obtaining occurrence times of reference points associated with heart beats of the subject, wherein said reference points are indicative of occurrence times of R peaks of heart beats of the subject; and
   controllably determine parameters of the stimulation signal generated by said neuro-stimulation unit, including synchronizing the stimulation signal with said occurrence times, wherein said stimulation signal comprises pulses synchronized with said occurrence times of said reference points;
   the system being configured to, at least partially simultaneously:
   apply one of said stimulation signals via said first electrode proximately to an acupoint not associated with cardiovascular function, wherein the acupoint not associated with cardiovascular function is at least one of: left Ki6 acupoint, right Ki6 acupoint, left Lv14 acupoint, right Lv14 acupoint, left St32 acupoint, right St32 acupoint, left Lv3 acupoint, and right Lv3 acupoint; and
   apply one of said stimulation signals via said second electrode proximately to an acupoint associated with cardiovascular function, wherein the acupoint associated with cardiovascular function is at least one of: left Ht7 acupoint, right Ht7 acupoint, left Gb34 acupoint, right Gb34 acupoint, left Ub14 acupoint, right Ub14 acupoint, left Ub15 acupoint, right Ub15 acupoint, left HUA T4 acupoint, right HUA T4 acupoint, left HUA T5 acupoint, and right HUA T5 acupoint,
   thereby increasing heart-rate variability of the subject.

2. The system of claim 1, wherein the heart activity signal is an ECG signal.

3. The system of claim 1 wherein said pulses have a pulse width smaller than 1 millisecond and a maximum voltage intensity smaller than 60 volts.

4. The system of claim 1 wherein said pulses are biphasic pulses.

5. The system of claim 1 wherein each pulse is delayed relative to a preceding R peak by a time delay between about 100 milliseconds and about 500 milliseconds.

6. The system of claim 1, wherein said at least two electrodes are embedded on patches, the patches being configured to be removably attachable onto the skin, and
   wherein said patches further accommodate a sensor functionally associated with said control module and configured to measure at least one physiological parameter of the subject, and
   wherein said sensor is selected from the group consisting of an IR sensor for measuring heart-rate, an accelerometer for measuring heart-rate, an impedance meter for measuring skin electrical resistance, a surface EMG sensor for measuring muscle activity and degree of contraction, a blood-pressure sensor, and a thermometer for measuring skin temperature.

7. The system of claim 6 wherein said control module is configured to vary a maximum intensity of stimulation signals according to a physiological parameter measured by said sensor.

8. A method for at least one of (a) affecting a heart-rate variability (HRV) of a subject and (b) treating arrhythmia of a subject, the method comprising:
   using the system of claim 1, delivering electrical neuro-stimulation to at least one core acupoint pair by applying an electrical stimulation signal at the acupoints, the core acupoint pair comprising a first acupoint associated with cardiovascular function and a second acupoint not associated with cardiovascular function.

9. The method of claim 8 wherein the electrical neuro-stimulation is delivered by a first pair of electrodes applying a first electrical stimulation signal at the acupoints, wherein a first electrode of the first pair is attached to the skin of the subject proximal the first acupoint and the second electrode of the first pair is attached to the skin of the subject proximal the second acupoint.

10. The method of claim 9 further comprising delivering electrical neuro-stimulation by a second pair of electrodes applying a second electrical stimulation signal at a second core acupoint pair, wherein a first electrode of the second pair is attached to the skin of the subject proximal a first acupoint of the second acupoint pair and the second electrode of the second pair is attached to the skin of the subject proximal a second acupoint of the second acupoint pair.

11. The method of claim 10 wherein the first signal applied to the first core acupoint pair and the second signal applied to the second core acupoint pair comprise repetitive pulses at an equal repetition rate, and the pulses of the first signal are simultaneous with the pulses of the second signal.

12. The method of claim 10 wherein the first signal applied to the first core acupoint pair and the second signal applied to the second core acupoint pair comprise repetitive pulses at an equal repetition rate, and the pulses of the first signal are partially simultaneous with the pulses of the second signal.

13. The method of claim 10 wherein the first signal and the second signal comprise repetitive pulses at an equal repetition rate, and the pulses of the first signal do not overlap with the pulses of the second signal.

14. The method of claim 8 wherein the signal applied to the first acupoint and the signal applied to the second acupoint comprise repetitive pulses at an equal repetition rate, and the pulses of the signal applied to the first acupoint are substantially simultaneous with the pulses of the signal applied to the second acupoint.

15. The method of claim 8 wherein the signal applied to the first acupoint and the signal applied to the second acupoint comprise repetitive pulses at an equal repetition rate, and the pulses of the signal applied to the first acupoint are partially simultaneous with the pulses of the signal applied to the second acupoint.

16. The method of claim 8 wherein the acupoint not associated with cardiovascular function is selected from the group consisting of: left Ki6 acupoint, right Ki6 acupoint, left Lv14 acupoint, right Lv14 acupoint, left St32 acupoint, right St32 acupoint, left Lv3 acupoint, and right Lv3 acupoint.

17. The method of claim 8 wherein the acupoint associated with cardiovascular function is selected from the group consisting of: left Ht7 acupoint, right Ht7 acupoint, left Pc6 acupoint, right Pc6 acupoint, left Gb34 acupoint, right Gb34 acupoint, left Ub14 acupoint, right Ub14 acupoint, left Ub15 acupoint, right Ub15 acupoint, left HUA T4 acupoint, right HUA T4 acupoint, left HUA T5 acupoint, and right HUA T5 acupoint.

18. The method of claim 8 further comprising:
receiving a heart activity signal indicative of temporal heart activity of the subject;
identifying reference points in the heart activity signal, thereby obtaining occurrence times of reference points associated with heart beats of the subject;
synchronizing pulses of the electrical stimulation signal with the occurrence times of the reference points.

19. The method of claim 18 wherein said pulses have a pulse width lower than 1 millisecond and a maximum voltage intensity lower than 60 volts.

20. The method of claim 18 wherein said pulses are biphasic pulses.

21. The method of claim 18, wherein each of said pulses is delayed relative to a preceding R peak by a time delay between about 100 milliseconds and about 500 milliseconds.

\* \* \* \* \*